US006433251B1

(12) United States Patent
Wagner et al.

(10) Patent No.: US 6,433,251 B1
(45) Date of Patent: Aug. 13, 2002

(54) PROMOTER REGULATING CIRCADIAN CLOCK FUNCTION AND PHOTOPERIODISM

(75) Inventors: D. Ry Wagner, Eugene, OR (US); Karen A. Hicks, Gambier, OH (US); Michelle Z. Spence, Olympia, WA (US); Henriette Foss; Xing Liang Liu, both of Eugene, OR (US); Michael F. Covington, San Diego, CA (US)

(73) Assignee: The State of Oregon acting by and through the State Board of Higher Education on behalf of the University of Oregon, Eugene, OR (US)

( * ) Notice: Subject to any disclaimer, the term of this patent is extended or adjusted under 35 U.S.C. 154(b) by 0 days.

(21) Appl. No.: 09/513,057

(22) Filed: Feb. 24, 2000

Related U.S. Application Data

(63) Continuation-in-part of application No. PCT/US99/18747, filed on Aug. 17, 1999.
(60) Provisional application No. 60/096,802, filed on Aug. 17, 1998.

(51) Int. Cl.$^7$ .............................. A01H 5/00; C12N 5/04; C12N 5/10; C12N 15/82; C12N 15/83; C12N 15/84; C12N 15/88; C12N 15/29
(52) U.S. Cl. ..................... 800/287; 536/23.6; 536/24.1; 435/468; 435/469; 435/470; 435/440; 435/418; 435/419; 435/411; 435/412; 435/414; 435/415; 435/422; 435/427; 800/278; 800/272; 800/293; 800/294; 800/298; 800/306; 800/312; 800/313; 800/314; 800/316; 800/317.1; 800/317.3; 800/317.4; 800/317; 800/320; 800/320.1
(58) Field of Search ............................... 536/23.1, 23.6, 536/24.1; 435/468, 470, 440, 418, 411, 412, 414, 415, 419, 422, 427, 469; 800/278, 287, 292, 293, 298, 306, 312, 313, 314, 316, 317.13, 317.2, 317.5, 319, 320, 320.1, 320.2, 320.3, 323, 294, 317.4

(56) References Cited

U.S. PATENT DOCUMENTS

| | | | |
|---|---|---|---|
| 4,990,607 A | 2/1991 | Katagiri et al. | |
| 5,811,536 A | 9/1998 | Yanofsky | |
| 6,002,069 A | 12/1999 | Yanofsky | |

FOREIGN PATENT DOCUMENTS

| | | |
|---|---|---|
| WO | WO 00/09658 | 2/2000 |

OTHER PUBLICATIONS

Donald et al, "Mutation of either G box or I box sequences profoundly affects expression from the Arabidopsis rbcS–1A promoter", 1990 The EMBO Journal vol. 9, No. 6 pp. 1717–1726.*

Chen et al, "Minimal regions in the Arabidopsis Pistillata promoter responsive to the Apetala3/pistillata feedback control do not contain a CArG box", 2000, Sex Plant Reprod. vol. pp. 85–94.*

Tymms et al, "A novel epithelial–expressed ETS gene, ELF3: human and murine cDNA sequences, murine genomic organization, human mapping to 1q32.2 and expression in tissues and cancer", 1997, Oncogene vol. 15 pp. 2449–2462.*

Rounsley et al, 1997, GenBank Accession No. B28787.*

Hicks et al., "Conditional Circadian Dysfunction of the Arabidopsis early–flowering 3 Mutant," *Science,* 274:790–792, Nov. 1, 1996.

Puzio et al., Nematode Responsive Protein, EMBL Accession No. Y11994, Jun. 20, 1997.

Wang and Tobin, "Constitutive Expression of the Circadian Clock Associated 1 (CAA1) Gene Disrupts Circadian Rhythms and Suppresses Its Own Expression," *Cell,* 93:1207–1217, Jun. 25, 1998.

Schaffer et al., "The late elongated hypocotyl Mutation of Arabidopsis Disrupts Circadian Rhythms and the Photoperiodic Control of Flowering," *Cell,* 93:1219–1229, Jun. 26, 1998.

Puzio et al., "Isolation of a gene from Arabidopsis thaliana related to nematode feeding structures," *Gene,* 239:163–175, 1999.

Zagotta et al., "Early–flowering Mutants of *Arabidopsis thaliana,*" *Aust. J. Plant Physiol.,* 19:411–418, 1992.

Weigel et al., "LEAFY Controls Floral Meristem Identity in Arabidopsis," *Cell,* 69:843–859, May 29, 1992.

Foden–Vencil, "Oregon research team studies genetic manipulation of plants," *Oregonian* Science section, Nov. 5, 1992.

"UO Molecular Biologist Studying Genes that Make Plants Flower," *Advance Science & Technology Institute,* University of Oregon, p. 5, 1994.

Newman et al., 21244 CD4–14 *Arabidopsis thaliana* cDNA clone F5H5T3, GenBank Accession #N96569, Jun. 5, 1998.

Hicks et al., "Arabidopsis early–flowering mutants reveal multiple levels of regulation in the vegetative–to–floral transition," *Cell Dev. Biol.* 7:409–418, 1996.

Zagotta et al., "The Arabidopsis ELF3 gene regulates vegetative photomorphogenesis and the photoperiodic induction of floweirng," *Plant J.,* 10(4):691–702, 1996.

Puzio et al., "A New Nematode Responsible Gene in Arabidopsis Thaliana," Database SPTREML–11, O04419, Mar. 21, 1997.

Puzio et al., Database Genebank, Accession number O04419, Jul. 1, 1997.

Shannon and Meeks–Wagner, "A Mutation in the Arabidopsis TFL1 Gene Affects Inflorescence Meristem Development," *The Plant Cell* 3:877–892, 1991.

* cited by examiner

Primary Examiner—David T. Fox
Assistant Examiner—Anne Kubelik
(74) Attorney, Agent, or Firm—Klarquist Sparkman, LLP

(57) ABSTRACT

Nucleic acid molecules that encode a plant promoter involved in photoperiodism and circadian rhythms are disclosed. These molecules may be introduced into plants in order to alter the photoperiodic and/or circadian clock-based gene expression of the plants.

12 Claims, 6 Drawing Sheets

FIG. 1 (Part 1)

FIG. 1 (Part 2)

FIG. 1 (Part 3)

FIGURE 2

```
BLOCK I:
AtELF3         13  PMFPRLHVND  ADKGG-PRAP  PRNKMALYEQ  LSIPSQRF     49
AtEEC          15  PLFPRVHVND  TGRGG-LSQQ  FDGFTMSLVS  SKRPNLPS     49
cardamineELF3  13  PMFPRLHVND  ADEGG-PRAP  PRNKMALYEQ  LSIPSERF     49
tomatoELF3     13  PMFPRLNVND  TEKGG-PRAP  PRNKMAIYEQ  LSIPSQRY     49
riceELF3       22  PLFPRLHVND  AAKGGGPRAP  PRNKMALYEQ  FTVPSHRF     59

BLOCK II:
AtELF3        317  SPDDVVGILG  QKRFWRARKA  IANQQRVFAV  QLFELHRLIK  VQKLIAASP  365
AtEEC         238  SSYDIARVIG  EKRFWKMRTY  MINQQKIFAG  QVFELHRLIM  VQKMVAKSP  285
cELF3         291  SPDDVVGAMG  QKRFWRARKA  ITNQQRVFAV  QLFELHRLIK  VQRLIAASP  339
tELF3         341  SPDDIVGIIG  LKRFWKARRA  IVNQQRVFAV  QVFELHRLIK  VQRLIAGSP  389
rELF3         394  SPDKIVGAIG  TKHFWKARRA  IMNQQRVFAV  QVFELHRKLVK VQKLIAASP  442
maizeELF3       ?  SPDDVVSAIG  PKHFWKARRA  IVNQQRVFAV  QVFELHRLIK  VQKLIAASP    ?

BLOCK III:
AtELF3        462  PPPSGNHQQW  LIPVHSPSEG  LLYKP       469
AtEEC         358  PPP-GN--QW  LVPVITDSDG  LVYKP       379
cELF3         441  PPPSGN-QQW  LIPVMSPSEG  LIYKP       464
tELF3         485  QQPSG-H-QW  LIPVHSPSEG  LVYKP       508
rELF3         544  -QPPQN--QW  LVPVHSPLEG  LVYKP       565
mELF3           ?  -------QW   LIPVMSPSEG  LVYKP         ?

BLOCK IV:
AtELF3        660  RVIKVVPHRA  KLASENAARI  FQSIQEER    691
AtEEC         505  RAIKAVPHNS  TSASESAARI  FRFIQEER    536
cELF3         577  RVIKVVPHRA  KLASEN----  --------    577
tELF3         677  RVIKVVPHNA  RSATESVARI  FQSIQQER    704
rELF3         729  NVIKVVPHNS  RTASESAARI  FRSIQMER    756
mELF3           ?  RVIRVVPHTA  RTASESAARI  FRSIQMER      ?
```

FIG. 3

Table 1. *Arabidopsis* seedlings overexpressing ELF3 have a reduced sensitivity to red light in hypocotyl elongation and flower late in LD. Mean hypocotyl length in millimeter and flowering time ± SE are indicated. Number of plants measured for each character and genotype is indicated in parenthesis

| Genotype | Hypocotyl Length in millimeter | Flowering Time As Number of Leaves at 1cm Bolt | | Flowering Time As Days to 1cm Bolt | |
|---|---|---|---|---|---|
| | | LD | SD | LD | SD |
| COL-0 | 5.69 ± 0.55 (21) | 10.8 ± 1.36 (20) | 64.60 ± 5.10 (10) | 29.00 ± 2.02 (20) | 102.4 ± 6.41 (10) |
| ELF3-OX | 2.96 ± 0.52 (27) | 42.5 ± 4.42 (16) | 57.03 ± 1.37 (47) | 60.56 ± 7.53 (16) | 96.96 ± 0.92 (47) |
| elf3-1 | 12.40 ± 0.94 (27) | 5.15 ± 0.73 (20) | 9.65 ± 2.95 (17) | 20.75 ± 1.26 (20) | 47.06 ± 6.59 (17) |
| phyB-9 | 14.69 ± 0.86 (20) | 7.17 ± 1.34 (18) | NA | 25.83 ± 1.98 (18) | NA |
| phyB/ELF3-OX | 10.09 ± 0.70 (19) | 44.07 ± 5.21 (27) | NA | 64.37 ± 9.58 (27) | NA |

FIG. 4

Features of the predicted 695 amino acid ELF3 protein

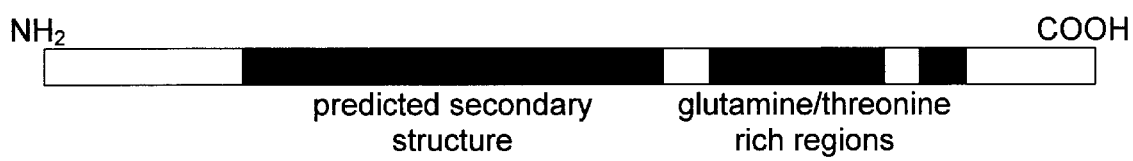

predicted secondary structure    glutamine/threonine rich regions

**Molecular basis of the *elf 3* mutations**

| | |
|---|---|
| elf3-1 | C to T change in exon 3 (stop) |
| elf3-2 | ~1.5 kb C-terminal deletion |
| elf3-3 | G to T change in exon 2 (stop) |
| elf3-4 | 11 bp deletion in exon 1 (stop) |
| elf3-5 | C to T change in exon 1 (stop) |
| elf3-6 | AG to AA change in the exon 4 splice acceptor site |
| elf3-7 | G to A change in the exon 1 splice donor site* |
| | *makes ~ 20% full length wild type *ELF*3 mRNA |
| elf3-8 | unknown |
| elf3-9 | unknown | ps
PROMOTER REGULATING CIRCADIAN CLOCK FUNCTION AND PHOTOPERIODISM

CROSS REFERENCE TO RELATED CASES

This is a continuation-in-part of International Application No. PCT/US99/18747, filed Aug. 17, 1999, which claims the benefit of U.S. Provisional Application No. 60/096,802, filed Aug. 17, 1998. Both of these applications are incorporated herein in their entirety.

FIELD OF THE INVENTION

This invention relates to genes that regulate circadian clock functions and photoperiodism in plants, and relates in particular to the ELF3 gene. Aspects of the invention include the purified ELF3 gene product (ELF3 protein), as well as nucleic acid molecules encoding this gene product. Nucleic acid vectors, transgenic cells, and transgenic plants having modified ELF3 activity are also provided.

BACKGROUND OF THE INVENTION

Shoot development in flowering plants is a continuous process ultimately controlled by the activity of the shoot apical meristem. Apical meristem activity during normal plant development is sequential and progressive, and can be summarized as a series of overlapping phases: vegetative→inflorescence→floral (V→I→F). Over the past 50 years many models have been proposed for the control of the vegetative-to-floral transition. These models range from simple single pathway models to complex multiple pathway models, and are largely based on physiological studies (for review, see Bernier, 1988). Modem techniques provide researchers with genetic and molecular methods that can be used to further investigate the control of V→I→F transitions.

One such modern technique now routinely practiced by plant molecular biologists is the production of transgenic plants carrying a heterologous gene sequence. Methods for incorporating an isolated gene sequence into an expression cassette, producing plant transformation vectors, and transforming many types of plants are well known. Examples of the production of transgenic plants having modified characteristics as a result of the introduction of a heterologous transgene include: U.S. Pat. No. 5,268,526 (modification of phytochrome expression in transgenic plants); U.S. Pat. No. 5,719,046 (production of herbicide resistant plants by introduction of bacterial dihydropteroate synthase gene); U.S. Pat. No. 5,231,020 (modification of flavenoids in plants); U.S. Pat. No. 5,583,021 (production of virus resistant plants); and U.S. Pat. Nos. 5,767,372 and 5,500,365 (production of insect resistant plants by introducing *Bacillus thuringiensis* genes).

Light quality, photoperiod, and temperature often act as important, and for some species essential, environmental cues for the initiation of flowering. However, there is very little information on the molecular mechanisms that directly regulate the developmental pathway from reception of the inductive light signal(s) to the onset of flowering and the initiation of floral meristems. The analysis of floral transition mutants in pea (*Pisum sativum*) (see Murfet, 1985) and Arabidopsis (see Koornneef et al., 1991) has demonstrated that at least part of the genetic hierarchy controlling flowering onset is responsive to the number of hours of light perceived by a plant within a 24 hour light/dark cycle. The monitoring of the length of the light period is referred to as the photoperiodic response. Photoperiodic responses have long been thought to be tied to one or more biological clocks that regulate many physiological and developmental processes on the basis of an endogenous circadian rhythm.

Many important physiological and developmental plant processes are influenced by circadian rhythms. These include the induction of gene transcription, leaf movement, stomatal opening, and the photoperiodic control of flowering. While the relationship of these plant processes to the circadian rhythm has long been recognized, the genetic analysis of circadian rhythms in plants has only recently begun. Most of the genetic analysis of circadian regulation has been performed with Drosophila and *Neurospora crassa*, where mutational studies have led to the isolation of the per and frq genes, respectively (Hall, 1990; Dunlap, 1993). These genes are thought to encode components of the circadian oscillator, in part because, while null alleles cause arrhythmic responses, alleles of these genes exist that produce either long or short period responses. Transcriptional production of per and frq mRNA cycles on a twenty-four hour period, and both genes regulate their own expression (Edery et al., 1994; Aronson et al., 1994).

Arabidopsis is a quantitative long-day (LD) plant—wild-type plants will initiate flowering more quickly when grown under LD light conditions than when grown under short-day (SD) light conditions. In order to identify genes required for floral initiation and development, populations of *Arabidopsis thaliana* ecotype Columbia grown in SD conditions have been screened for early-flowering mutants. Isolated mutants were then examined for additional shoot development anomalies, and those with discreet shoot phenotypes related to meristem function or light perception were considered for further analysis. Such mutants may identify genes that are part of functionally redundant pathways that operate, to varying degrees, as "fail-safe" mechanisms for ensuring shoot growth and reproductive development. Examples of such functionally redundant pathways have been described in studies of Drosophila (e.g., Hülskamp et al., 1990) and *C. elegans* (e.g., Lambie and Kimble, 1991). The key genes identified by these Arabidopsis screens were the TERMINAL FLOWER 1 (TFL1) gene and the EARLY-FLOWERING 3 (ELF3) gene (Shannon and Meeks-Wagner, 1991; Zagotta et al., 1992).

The early-flowering (elf3) mutant of Arabidopsis is insensitive to photoperiod with regard to floral initiation. Plants homozygous for a mutation in the ELF3 locus flower at the same time in LD and SD growth conditions, whereas floral initiation of wild-type plants is promoted by LD growth conditions (Zagotta et al., 1992; Zagotta et al., 1996). In LD conditions, the flowering time of the elf3-1 heterozygote is intermediate between wild-type and the homozygous mutant. In addition to being photoperiod-insensitive, all elf3 mutants display the long hypocotyl phenotype characteristic of plants defective in light reception or the transduction of light signals (Zagotta et al., 1992; Zagotta et al, 1996). The majority of long hypocotyl mutants that have been identified are defective in red light-mediated inhibition of hypocotyl elongation. In contrast, elf3 mutants are primarily defective in blue light-dependent inhibition of hypocotyl elongation, although they are also partially deficient in red light-dependent inhibition of hypocotyl elongation (Zagotta et al., 1996).

The availability of the ELF3 gene would facilitate the production of transgenic plants having altered circadian clock function and programmed photoperiodic responses. It is to such a gene that the present invention is directed.

SUMMARY OF THE INVENTION

The invention provides an isolated ELF3 gene from Arabidopsis that is shown to complement the elf3 photoperiod-insensitive flowering and elongated hypocotyl defects when introduced into elf3 mutant plants.

One aspect of this invention is a purified protein having ELF3 protein biological activity. The prototypical Arabidopsis ELF3 protein has the amino acid sequence shown in SEQ ID NO: 2. Variants of this protein that differ from SEQ ID NO: 2 by one or more conservative amino acid substitutions are also provided, as are homologs of the ELF3 protein. Such homologs typically share at least 60% sequence identity with the sequence shown in SEQ ID NO: 2. Nucleic acid molecules encoding these proteins are also part of this invention. Such nucleic acid molecules include those having the nucleotide sequences set forth in SEQ ID NO: 1, SEQ ID NO: 3, and SEQ ID NO:4.

Recombinant nucleic acid molecules in which a promoter sequence is operably linked to any of these ELF3 protein-encoding nucleic acid sequences are further aspects of this invention. The invention also provides cells transformed with such a recombinant nucleic acid molecule and transgenic plants comprising the recombinant nucleic acid molecule. Such transgenic plants may be, for instance, Arabidopsis, pepper, tomato, tobacco, broccoli, cauliflower, cabbage, canola, bean, soybean, rice, corn, wheat, barley, citrus, cotton, cassava and walnut, trees such as poplar, oak, maple, pine, spruce, and other conifers, and ornamental plants (e.g., petunias, orchids, carnations, roses, impatiens, pansies, lilies, snapdragons, geraniums, and so forth).

A further aspect of this invention is an isolated nucleic acid molecule or oligonucleotide comprising 15, 20, 30, 50, or 100 contiguous nucleotides of the sequence shown in SEQ ID NOs: 1, 3, or 4. Such nucleic acid molecules or oligonucleotides may be operably linked to a promoter sequence, and may be in the sense or antisense orientation in relation to such a promoter. The invention also includes cells and plants transformed with such recombinant nucleic acid molecules, with or without an attached promoter.

Further embodiments of this invention include isolated nucleic acid molecules that hybridize under specified hybridization conditions to the nucleic acid sequence set forth in SEQ ID NO: 1, and that encode a protein having ELF3 protein biological activity. Closely related ELF3 gene homologs may be detected by hybridization under stringent conditions, whereas less closely related homologs may be detected by hybridization at low stringency. Appropriate wash conditions for stringent hybridization may be 55° C., 0.2×SSC and 0.1% SDS for 1 hour. Appropriate wash conditions for low stringency hybridization may be 50° C., 2×SSC, 0.1% for 3 hours. Such a hybridizing isolated nucleic acid molecule may be operably linked to a promoter for expression in plants. Cells transformed with such a recombinant nucleic acid molecule, and transgenic plants that comprise such a molecule, are also provided.

The invention also provides the 5' regulatory region of the ELF3 gene. This regulatory region, or parts thereof, may be used to obtain ELF3-like circadian-rhythm expression of particular genes. For example, the ELF3 5' regulatory region may be operably linked to an open reading frame of a gene of interest, and the resulting recombinant construct may be introduced into a plant by transformation. One embodiment of an ELF3 regulatory region is about nucleotides 1 through about 1900 of the 5' upstream region shown in SEQ ID NO: 5.

BRIEF DESCRIPTION OF THE DRAWINGS

Figure 1:
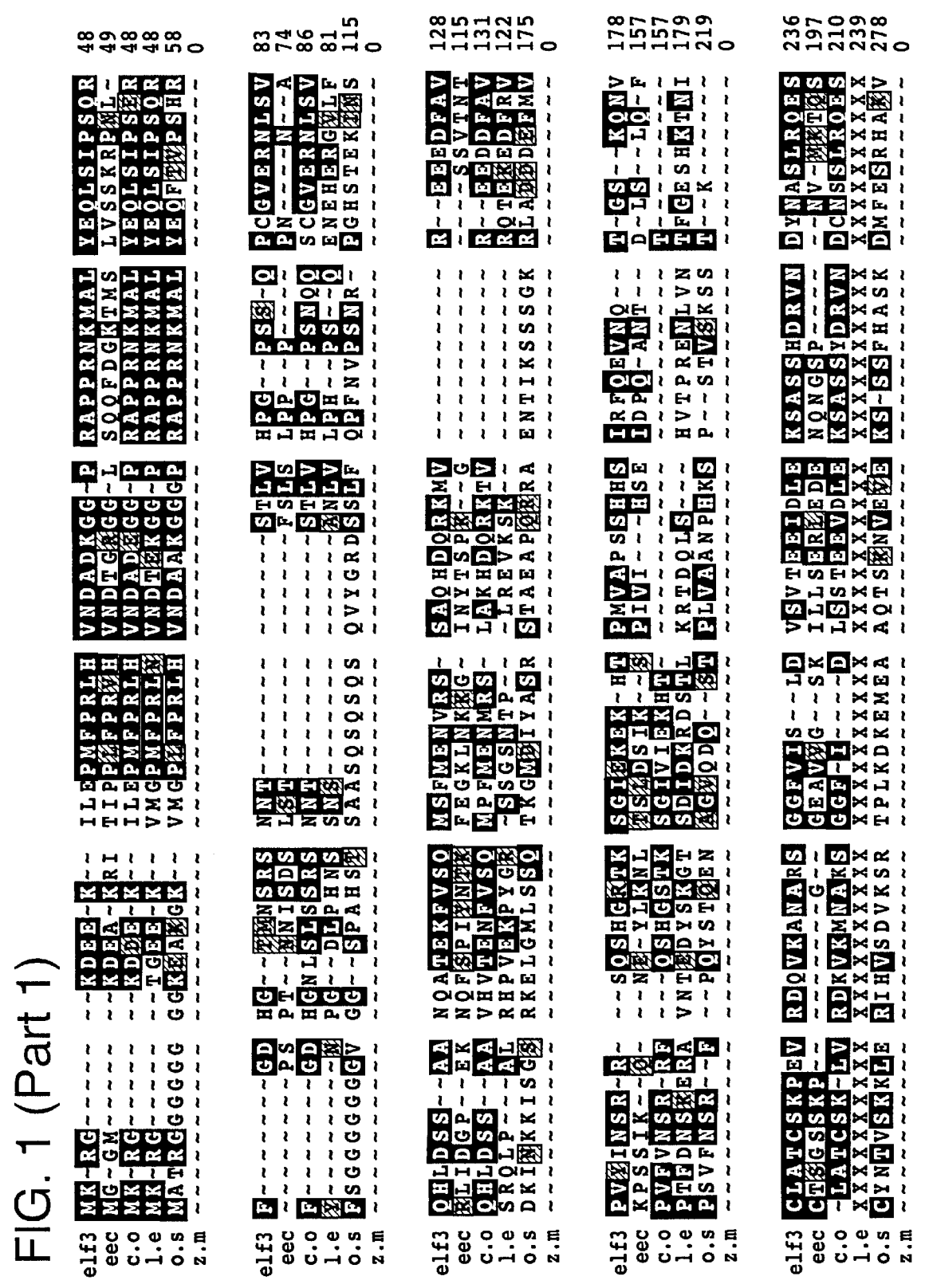
Figure 1:
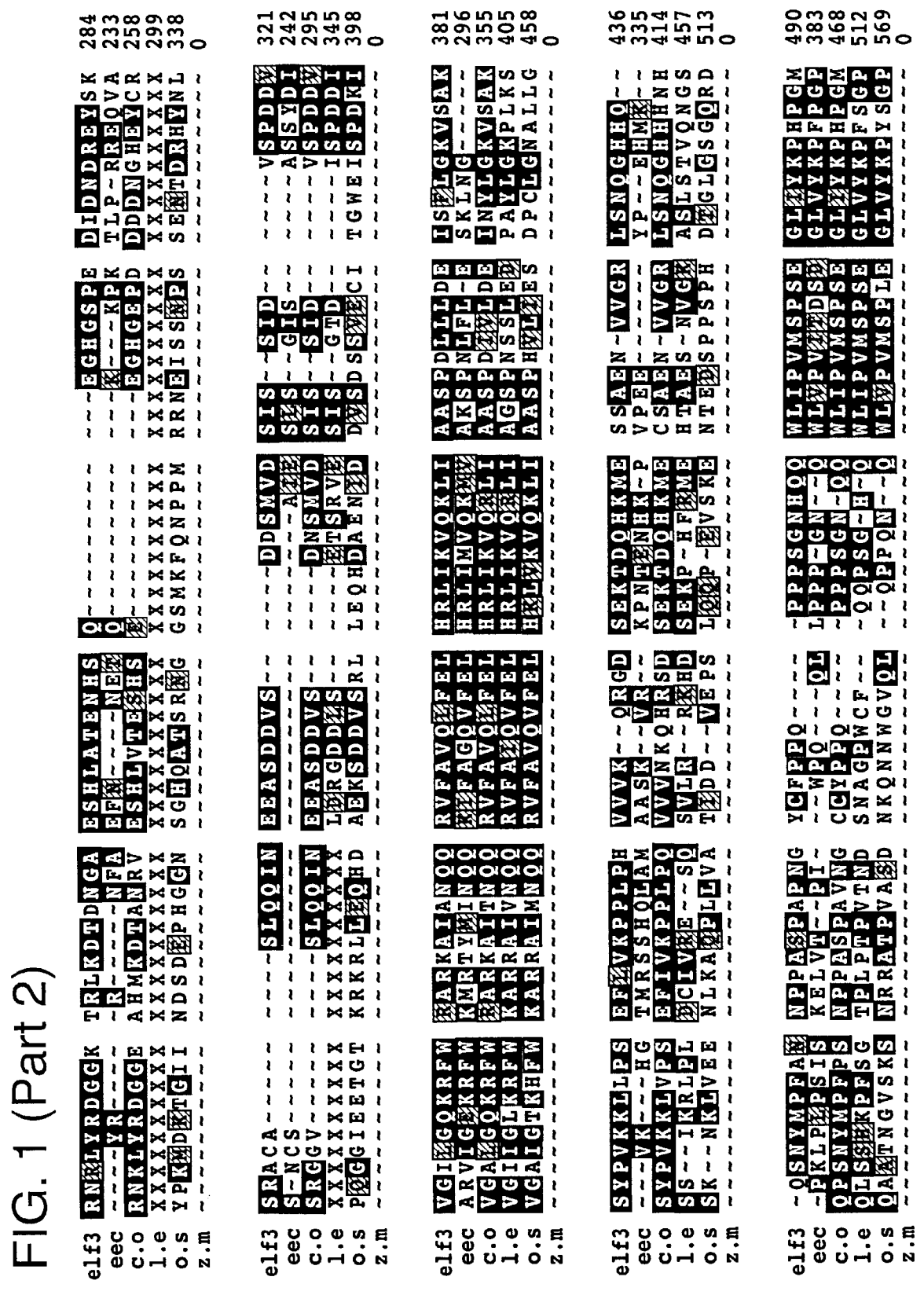
Figure 1:
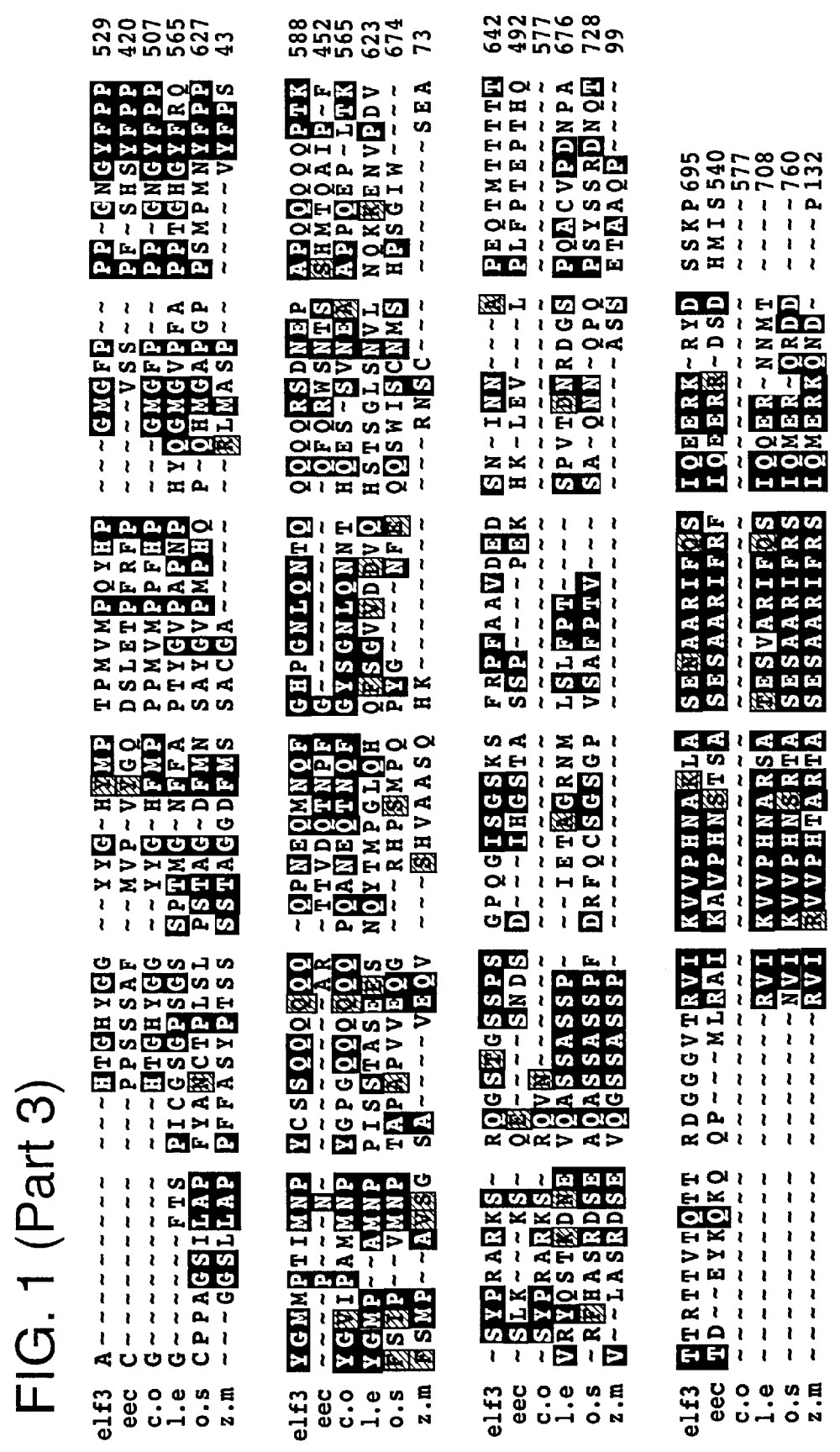

FIG. 1. Sequence Comparison of ELF3 Homologs

Multiple-sequence alignment of ELF3 and several putative ELF3 homologs from *Arabidopsis thaliana* (Essence of ELF3 Consensus, EEC) and other plant species (*Cardamine oligosperma*, tomato, rice, and maize). Protein designations are given on the left in the same order. Amino acid residues are numbered on the right. Residues shaded in black indicate identity of at least three ELF3/ELF3-related sequences in the alignment; light-shaded residues indicate similarity to consensus. Nucleotide sequences from *C. oligosperma* (a member of the family Brassicaceae) were obtained by sequencing polymerase chain reaction products using degenerate oligos to the Arabidopsis ELF3 gene and genomic DNA or cDNA prepared from *C. oligosperma* seedlings. Sequences were aligned and analyzed using CLUSTAL W (J. D. Thompson, D. G. Higgins, T. Gibson, *Nucleic Acids Res.* 22, 4673–80, 1994) and PrettyBox (Genetics Computer Group, Inc., Madison, Wis.).

FIG. 2. Sequence Comparison of ELF3 Homologs Showing Consensus Boxes

Multiple-sequence alignment shows four highly conserved regions within ELF3 and putative ELF3 homologs from *Arabidopsis thaliana* (Essence of ELF3 Consensus, EEC) and other plant species (*Cardamine oligosperma*, tomato, rice, and maize). Protein designations are given on the left in the same order. Amino acid residues are numbered on both the right and left. Residues shaded in black indicate identity of at least three ELF3/ELF3-related sequences in the alignment; light-shaded residues indicate similarity to consensus. Sequences were aligned and analyzed using CLUSTAL W (J. D. Thompson, D. G. Higgins, T. Gibson, *Nucleic Acids Res.* 22, 4673–80, 1994) and PrettyBox (Genetics Computer Group, Inc., Madison, Wis.).

GenBank accession numbers for ELF3 and putative ELF3 homologs are as follows: AtELF3 (*A. thaliana* genomic DNA: AC004747, published Dec. 17, 1999), AtEEC (*A. thaliana* genomic DNA: AB023045, published Nov. 20, 1999), cELF3 (yet to be submitted), tELF3 [*Lycopersicon esculentum* Expressed Sequence Tags (ESTs) from Clemson University Genomics Institute: AW093790 (Oct. 18, 1999), AI894513 (Jul. 27, 1999), AI488927 (Jun. 29, 1999), AI486934 (Jun. 29, 1999), AI894398 (Jul. 27, 1999)], rELF3 (*Oryza sativa* genomic DNA: AP000399, published Dec. 3, 1999), mELF3 (*Zes mays* EST from Stanford University Genome Center: AI637184, published Apr. 26, 1999).

FIG. 3 is a Table showing growth and flowering characteristics of Arabidopsis seedlings over-expressing ELF3 (ELF3-OX), seedlings that are mutant in ELF3 (elf3-1).

FIG. 4 shows the features of the predicted 695 amino acid ELF3 protein, and the molecular basis of the several elf3 mutations.

SEQUENCE LISTING

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NO: 1 shows the cDNA and amino acid sequence of Arabidopsis ELF3.

SEQ ID NO: 2 shows the amino acid sequence of Arabidopsis ELF3 protein.

SEQ ID NO: 3 shows the genomic sequence of Arabidopsis ELF3. The sequence comprises the following regions:

| Nucleotides | Feature |
|---|---|
| 1–142 | promoter region |
| 143–424 | exon 1 (5' UTR) |
| 425–644 | exon 1 continued (initiating ATG at 425) |
| 645–1006 | intron 1 |
| 1007–1803 | exon 2 |
| 1804–2983 | intron 2 |
| 2984–3037 | exon 3 |
| 3038–3127 | intron 3 |
| 3128–4142 | exon 4 |
| 4143–4145 | stop codon |
| 4146–4221 | 3' UTR and 3' regulatory region |

SEQ ID NO: 4 shows the DNA and corresponding amino acid sequence of the Arabidopsis ELF3 ORF.

SEQ ID NO: 5 shows the 4071 base pair Arabidopsis ELF3 5' regulatory region.

SEQ ID NO: 6–11 show primers that can be used to amplify certain portions of the Arabidopsis ELF3 sequence.

SEQ ID NO: 12 shows the cDNA and corresponding amino acid sequence of the *Cardamine oligosperma* ELF3 ortholog, cELF3. This sequence can also be determined by applying well known computer analyses to the genomic sequence shown in SEQ ID NO: 14 (also referred to as COELF3~1) to determine where the introns and exons are.

SEQ ID NO: 13 (also referred to as COELF3~2) shows the amino acid sequence of the *Cardamine oligosperma* ELF3 ortholog, cELF3.

SEQ ID NO: 14 (also referred to as COELF3~1) shows the genomic sequence of the *Cardamine oligosperma* ELF3 ortholog, cELF3.

SEQ ID NO: 15 shows a partial DNA sequence (also referred to as PEAELF~2) of the pea ELF 3 ortholog.

SEQ ID NO: 16 (also referred to as PEAELF~1) shows the amino acid sequence of the partial pea ELF 3 ortholog.

SEQ ID NO: 17 (also referred to as BROCCA~2) shows the amino acid sequence of the broccoli/cauliflower EEC protein.

SEQ ID NO: 18 shows a partial DNA (also referred to as GMELF3~2) sequence of the *Glycine max* (soybean) ELF3 coding region.

SEQ ID NO: 19 (also referred to as GMELF3~1) shows the amino acid sequence of the partial*Glycine max* (soybean) ELF3 protein.

SEQ ID NO: 20 shows the DNA (also referred to as BROCCA~1) a sequence of the

SEQ ID NO: 20 shows the DNA (also referred to as BROCCA~1) a sequence of the *Lycopersicon esculentum* (tomato) ELF3 (N-terminus #2) coding region.

SEQ ID NO: 21 shows the DNA (also referred to as LEAFFO~1) sequence of the *Lycopersicon esculentum* (tomato) ELF3 (N-terminus #1) coding region.

SEQ ID NO: 22 shows the DNA (also referred to as LE5B39~1) sequence of the *Lycopersicon esculentum* (tomato) coding region.

SEQ ID NO: 23 (also referred to as LEELF3~3) shows the amino acid sequence of the *Lycopersicon esculentum* (tomato) ELF3 (C-terminus) coding region.

SEQ ID NO: 24 (also referred to as LEELF~2) shows a partial amino acid sequence of the *Lycopersicon esculentum* (tomato) protein.

SEQ ID NO: 25 (also referred to as LEELF3~1) shows the amino acid sequence of the *Lycopersicon esculentum* (tomato) ELF3 (N-terminus #2) protein.

SEQ ID NO: 26 shows the DNA (also referred to as OSELF3~2) sequence of the *Oryza sativa* (rice) ELF3 genomic region.

SEQ ID NO: 27 (also referred to as OSELF3~1) shows the amino acid sequence of the *Oryza sativa* (rice) ELF3 protein.

SEQ ID NO: 28 shows a partial DNA (also referred to as ZM8CC4~1) sequence of the *Zes mays* (maize) ELF3 coding region.

SEQ ID NO: 29 (also referred to as ZMELF3~2) shows the amino acid sequence of the partial *Zes mays* (maize) ELF3 protein.

SEQ ID NO: 30 shows a partial DNA (also referred to as ZMELF3~4) sequence of the *Zes mays* (maize) ELF3 #2 coding region.

SEQ ID NO: 31 (also referred to as ZMELF3~3) shows the amino acid sequence of the partial *Zes mays* (maize) ELF3 #2 coding region.

SEQ ID NO: 32 shows the DNA (also known as ATEECG~1) of the *Arabidopsis thaliana* EEC genomic region.

SEQ ID NO: 33 (also known as ATEECP~1) shows the amino acid sequence of the *Arabidopsis thaliana* EEC protein.

SEQ ID NO: 34 shows the DNA (also known as ATELF3~1) sequence of the *Arabidopsis thaliana* ELF3 genomic region.

SEQ ID NO: 35 (also known as ATELF3~2) shows the amino acid sequence of the *Arabidopsis thaliana* ELF3 protein.

DETAILED DESCRIPTION OF THE INVENTION

I. Definitions

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following definitions of terms are provided:

ELF3 gene/ELF3 cDNA: Nucleic acid molecules that encode an ELF3 protein. Nucleic acid molecules that encode the Arabidopsis ELF3 protein are provided in SEQ ID NO: 3 (Arabidopsis ELF3 gene), SFQ ID NO: 1 (Arabidopsis ELF3 cDNA) and SEQ ID NO:4 (Arabidopsis ELF3 open reading frame). The invention includes not only the nucleic acid molecules provided in SEQ ID NOS: 1, 3 and 4, but also homologs and orthologs of these sequences, other nucleic acid molecules that encode ELF3 proteins, and probes and primers that are derived from these sequences.

elf3 mutant: The early-flowering (elf3) mutant of Arabidopsis is insensitive to photoperiod with regard to floral initiation (Zagotta et al., 1992; Zagotta et al., 1996). In addition to being photoperiod-insensitive, all Arabidopsis efl3 mutants display the long-hypocotyl phenotype characteristic of plants defective in light reception or the transduction of light signals (Zagotta et al., 1992; Zagotta et al., 1996). Elf3 mutants are primarily defective in blue light-dependent inhibition of hypocotyl elongation, although elf3 mutants are also partially deficient in red light-dependent inhibition of hypocotyl elongation (Zagotta et al., 1996).

ELF3 protein: A protein having ELF3 protein biological activity and sharing amino acid sequence identity with the amino acid sequence of the prototypical ELF3 protein shown in SEQ ID NO: 2 (the Arabidopsis ELF3 protein). ELF3 proteins that are more distantly related to the prototypical ELF3 protein will share at least 60% amino acid sequence identity with the sequence shown in SEQ ID NO: 2, as determined by the methods described below. More closely related ELF3 proteins may share at least 70%, 75% or 80% sequence identity with the Arabidopsis ELF3 protein. ELF3 proteins that are most closely related to the Arabidopsis protein will have ELF3 protein biological activity and share at least 85%, 90% or 95% sequence identity with the Arabidopsis protein.

ELF3 protein biological activity: The ability of a protein to complement an elf3 mutant. The ability of a protein to complement an elf3 mutant may be readily determined by introducing the gene encoding the protein into an elf3 mutant plant using standard methods. If the encoded protein has ELF3 protein biological activity, this will be manifested as a proportion of the transgenic progeny plants having a wild-type phenotype for those characteristics linked to the elf3 mutant (e.g., photoperiod-insensitive flowering and elongated hypocotyl).

ELF3 promoter: The region of nucleic acid sequence upstream (5') of the ELF3 coding sequence that is responsible for spatial and temporal regulation of ELF3 transcription. ELF3 transcription is circadian regulated, but with an RNA maximum that is "later" in the 24-hour period than that of other known circadian genes, e.g., CAB, CCR2, CCA1 and LHY (Wang and Tobin, 1998; Schaffer et al., 1998). ELF3-like circadian rhythm or cyclic transcriptional regulation refers to this type of a relatively delayed transcription maximum. Because ELF3 transcription reaches a maximal level relatively late in the 24-hour period, the ELF3 promoter will allow for altering the setting of the circadian clock. For instance, if another circadian-regulated gene (e.g., chlorophyll a/b binding protein) is expressed from the ELF3 promoter, the circadian set on this protein will be delayed to match that of ELF3. In addition, the ELF3 promoter may be used to provide altered expression of other genes that are under control of the circadian clock, if clock components and/or regulators such as CCA1 and LHY are driven by the ELF3 promoter instead of their own promoters or a constitutive promoter, for instance the 35S promoter.

The ELF3 promoter region is contained within the 4071 kb 5' regulatory region sequence shown in SEQ ID NO: 5, but one of ordinary skill in the art will appreciate that expression may be controlled by using less than this entire 5' upstream region, e.g., nucleotides 500–4071, 1000–4071, 1500–4071, 2000–4071, 2500–4071, 3000–4071, 3500–4071 or 4000–4071. One embodiment of an ELF3 promoter is about nucleotides 1 through about 1900 of the 5' upstream region shown in SEQ ID NO: 5.

Sequences as short as 50 or 100 nucleotides from within the 5' regulatory region may also be employed. The degree to which such a sequence provides for ELF3-like circadian cyclic transcriptional regulation, when included in an expression vector, can be ascertained by the methods described herein. Thus, the term "biologically active ELF3 promoter" refers to a 5' regulatory region of an ELF3 gene, or a part or a variant of such a region, that, when operably linked to the 5' end of an ORF and introduced into a plant, results in ELF3-like (i e., relatively late) circadian cyclic transcript expression of the protein encoded by the ORF.

Essence of ELF3 Consensus (EEC): One or more highly conserved regions of amino acid sequence within an ELF3 protein or ELF3 protein homolog. EECs are depicted in FIGS. 1 and 2.

Oligonucleotide: A linear polynucleotide sequence of up to about 100 nucleotide bases in length.

Probes and primers: Nucleic acid probes and primers can be readily prepared based on the nucleic acid molecules provided in this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acid molecules, typically DNA oligonucleotides 15 nucleotides or more in length. Primers can be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (1989), Ausubel et al. (1987), and Innis et al. (1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, for example, a primer comprising 20 consecutive nucleotides of the Arabidopsis ELF3 cDNA or gene will anneal to a target sequence such as an ELF3 gene homolog from tomato contained within a tomato genomic DNA library with a higher specificity than a corresponding primer of only 15 nucleotides. Thus, in order to obtain greater specificity, probes and primers can be selected that comprise 20, 25, 30, 35, 40, 50 or more consecutive nucleotides of the Arabidopsis ELF3 cDNA or gene sequences.

The invention thus includes isolated nucleic acid molecules that comprise specified lengths of the disclosed ELF3 cDNA or gene sequences. Such molecules may comprise at least 20, 25, 30, 35, 40, 50 or 100 consecutive nucleotides of these sequences and may be obtained from any region of the disclosed sequences. By way of example, the Arabidopsis ELF3 cDNA, ORF and gene sequences may be apportioned into halves or quarters based on sequence length, and the isolated nucleic acid molecules may be derived from the first or second halves of the molecules, or any of the four quarters. The Arabidopsis ELF3 cDNA, shown in SEQ ID NO: 1, can be used to illustrate this. The Arabidopsis ELF3 cDNA is 2518 nucleotides in length and so may be hypothetically divided into about halves (nucleotides 1–1259 and 1260–2518) or about quarters (nucleotides 1–629, 630–1259, 1260–1889 and 1890–2518). Nucleic acid molecules may be selected that comprise at least 20, 25, 30, 35, 40, 50 or 100 consecutive nucleotides of any of these or other portions of the Arabidopsis ELF3 cDNA. Thus, representative nucleic acid molecules might comprise at least 25 consecutive nucleotides of the region comprising nucleotides 1–1259 of the disclosed Arabidopsis cDNA, or of the regions comprising nucleotides 1–1135 or 2502–2518 of the cDNA.

Sequence identity: The similarity between two nucleic acid sequences, or two amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs of the Arabidopsis ELF3 protein will possess a relatively high degree of sequence identity when aligned using standard methods. Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad Sci. USA* 85: 2444, 1988; Higgins & Sharp *Gene,* 73: 237–244, 1988; Higgins & Sharp *CABIOS* 5: 151–153, 1989; Corpet et al. *Nuc. Acids Res.* 16, 10881–90, 1988; Huang et al. *Computer Appls. in the Biosciences* 8, 155–65, 1992; and Pearson et al. *Meth. Mol. Bio.* 24, 307–31, 1994. Altschul et al. (*J. Mol. Biol.* 215:403–410, 1990), presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx.

Homologs of the disclosed Arabidopsis ELF3 protein typically possess at least 60% sequence identity counted over full length alignment with the amino acid sequence of Arabidopsis ELF3 using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, at least 75%, at least 80%, at least 90%, at least 91%, at least 92%, at least 93%, at least 94% or at least 95% sequence identity. When less than the entire sequence is being compared for sequence identity, homologs will typically possess at least 75% sequence identity over short windows of 10–20 amino acids, and may possess sequence identities of at least 85% or at least 90% or 95% or more depending on their similarity to the reference sequence. Methods for determining sequence identity over such short windows are described at http://www.ncbi.nlm.nih.gov/BLAST/blast_FAQs.html. One of ordinary skill in the art will appreciate that these sequence identity ranges are provided for guidance only; it is entirely possible that strongly significant homologs could be obtained that fall outside of the ranges provided. The present invention provides not only the peptide homologs that are described above, but also nucleic acid molecules that encode such homologs. ELF3 homologs will typically also have ELF3 protein biological activity.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (1989) and Tijssen (1993). Nucleic acid molecules that hybridize under stringent conditions to the Arabidopsis ELF3 sequences will typically hybridize to a probe based on either the entire Arabidopsis ELF3 cDNA or selected portions of the cDNA under wash conditions of 0.2×SSC, 0.1% SDS at 55° C. for 1 hour. A more detailed discussion of hybridization conditions, including low stringency conditions, is presented below.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Ortholog: Two nucleotide or amino acid sequences are orthologs of each other if they share a common ancestral sequence and diverged when a species carrying that ancestral sequence split into two species. Orthologous sequences are also homologous sequences.

Specific binding agent: An agent that binds substantially only to a defined target. Thus an ELF3 protein specific binding agent binds substantially only the ELF3 protein. As used herein, the term "ELF3 protein specific binding agent" includes anti-ELF3 protein antibodies and other agents that bind substantially only to the ELF3 protein.

Anti-ELF3 protein antibodies may be produced using standard procedures described in a number of texts, including Harlow and Lane (1988). The determination that a particular agent binds substantially only to the ELF3 protein may readily be made by using or adapting routine procedures. One suitable in vitro assay makes use of the Western blotting procedure (described in many standard texts, including Harlow and Lane (1988)). Western blotting may be used to determine that a given ELF3 protein binding agent, such as an anti-ELF3 protein monoclonal antibody, binds substantially only to the ELF3 protein.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules.

Purified: The term purified does not require absolute purity; rather, it is intended as a relative term. Thus, for example, a purified ELF3 protein preparation is one in which the ELF3 protein is more enriched than the protein is in its natural environment within a cell. Generally, a preparation of ELF3 protein is purified such that ELF3 represents at least 5% of the total protein content of the preparation. For particular applications, higher purity may be desired, such that preparations in which ELF3 represents at least 25%, 50% or at least 90% of the total protein content may be employed.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

cDNA (complementary DNA): A piece of DNA lacking internal, non-coding segments (introns) and regulatory sequences that determine transcription. cDNA is synthesized in the laboratory by reverse transcription from messenger RNA extracted from cells.

ORF (open reading frame): A series of nucleotide triplets (codons) coding for amino acids without any internal termination codons. These sequences are usually translatable into a peptide.

Transgenic plant: As used herein, this term refers to a plant that contains recombinant genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually).

II. ELF3 Protein and Nucleic Acid Sequences

This invention provides ELF3 proteins and ELF3 nucleic acid molecules, including cDNA and gene sequences. The prototypical ELF3 sequences are the Arabidopsis sequences, and the invention provides for the use of these sequences to produce transgenic plants, such as corn and rice plants, having increased or decreased levels of ELF3 protein.

a. Arabidopsis ELF3

The Arabidopsis ELF3 genomic sequence is shown in SEQ ID NO: 3. The sequence comprises three introns and four exons, and encodes a protein that is 696 amino acids in length (SEQ ID NO: 2 shows the amino acid sequence of the ELF3 protein). The Arabidopsis ELF3 protein shares no significant homology to any known published proteins with assigned function. However, one published Arabidopsis EST (GenBank #N96569; Newman et al., 1994) overlaps nucleotides 853–2088 of the Arabidopsis ELF3 open reading frame (ORF) (SEQ ID NO: 4) (nucleotides 1136–2501 of the Arabidopsis ELF3 cDNA, SEQ ID NO: 1).

GenBank accession numbers for ELF3 and putative ELF3 homologs identified as such by this research group are as follows: AtELF3 (*A. thaliana* genomic DNA: AC004747, published Dec. 17, 1999), AtEEC (*A. thaliana* genomic DNA: AB023045, published Nov. 20, 1999), cELF3 (yet to be submitted), tELF3 [*Lycopersicon escutentum* Expressed Sequence Tags (ESTs) from Clemson University Genomics Institute: AW093790 (Oct. 18, 1999), AI894513 (Jul. 27, 1999), AI488927 (Jun. 29, 1999), AI486934 (Jun. 29, 1999), AI894398 (Jul. 27, 1999)], rELF3 (*Oryza sativa* genomic DNA: AP000399, published Dec. 3, 1999), and mELF3 (*Zea mays* EST from Stanford University Genome Center: AI637184, published Apr. 26, 1999).

The cDNA corresponding to the ELF3 gene is shown in SEQ ID NO: 1, and the ELF3 ORF is shown in SEQ ID NO: 4. As described below, the Arabidopsis ELF3 protein has ELF3 biological activity, i e., it complements the defective characteristics of photoperiod-insensitive flowering and elongated hypocotyl in elf3 mutant plants when the ELF3 gene sequence is introduced into these plants and the ELF3 protein is thereby expressed. In addition, ELF3 proteins contain one or more ESSENCE of ELF3 CONSENSUS (EEC) regions (see FIG. 2).

With the provision herein of the Arabidopsis ELF3 cDNA and gene sequences, the polymerase chain reaction (PCR) may now be utilized as a preferred method for producing nucleic acid sequences encoding the Arabidopsis ELF3 protein. For example, PCR amplification of the Arabidopsis ELF3 cDNA sequence may be accomplished either by direct PCR from a plant cDNA library or by reverse-transcription PCR (RT-PCR) using RNA extracted from plant cells as a template. Methods and conditions for both direct PCR and RT-PCR are known in the art and are described in Innis et al. (1990). Any plant cDNA library would be useful for direct PCR. The ELF3 gene sequences can be isolated from other libraries, for instance the IGF Arabidopsis BAC library (Mozo et al. 1998)

The selection of PCR primers will be made according to the portions of the ELF3 cDNA (or gene) that are to be amplified. Primers may be chosen to amplify small segments of the cDNA, the open reading frame, the entire cDNA molecule or the entire gene sequence. Variations in amplification conditions may be required to accommodate primers of differing lengths; such considerations are well known in the art and are discussed in Innis et al. (1990), Sambrook et al. (1989), and Ausubel et al. (1992). By way of example only, the Arabidopsis ELF3 cDNA molecule as shown in SEQ ID NO: 1 (excluding the poly A tail) may be amplified using the following combination of primers:

primer 1: 5' TGAAAACTCACTTTGGTTTTGTT
TG 3'     (SEQ ID NO: 6)

primer 2: 5' AAGACAAATTAACACATATAAAT
GA 3'     (SEQ ID NO: 7)

The open reading frame portion of the cDNA (SEQ ID NO: 4) may be amplified using the following primer pair:

primer 3: 5' ATGAATAGAGGGAAAGATGAGGA
G 3'     (SEQ ID NO: 8)

primer 4: 5' TTAAGGCTTAGAGGAGTCATAGC
GT 3'     (SEQ ID NO: 9)

These primers are illustrative only; one of ordinary skill in the art will appreciate that many different primers may be derived from the provided cDNA and gene sequences in order to amplify particular regions of these molecules. Resequencing of PCR products obtained by these amplification procedures is recommended; this will facilitate confirmation of the amplified sequence and will also provide information on natural variation in this sequence in different ecotypes and plant populations. Oligonucleotides derived from the Arabidopsis ELF3 sequence may be used in such sequencing methods.

Oligonucleotides that are derived from the Arabidopsis ELF3 cDNA or gene sequences are encompassed within the scope of the present invention. Preferably, such oligonucleotide primers will comprise a sequence of at least 15–20 consecutive nucleotides of the Arabidopsis ELF3 cDNA or gene sequences. To enhance amplification specificity, oligonucleotide primers comprising at least 25, 30, 35, 40, 45 or 50 consecutive nucleotides of these sequences may also be used.

b. ELF3 Genes in Other Plant Species

Orthologs of the ELF3 gene are present in a number of plant species including Chlamydomonas, Douglas fir, corn, rice, poplar, tobacco, Cardamine, and tomato (see Examples 4 and 5, below). With the provision herein of the prototypical ELF3 protein from Arabidopsis and cDNA and gene sequences that encode this protein, cloning of cDNAs and genes that encode ELF3 protein orthologs in other plant species is now enabled. Standard methods, including those described herein, can be used. As described above, orthologs of the disclosed Arabidopsis ELF3 protein have ELF3 protein biological activity and typically possess at least 60% sequence identity counted over the full length alignment with the amino acid sequence of Arabidopsis ELF3 using the NCBI Blast 2.0, gapped blastp set to default parameters. Proteins with even greater similarity to the Arabidopsis sequence will show greater percentage identities when assessed by this method, such as at least 70%, at least 75%, at least 80%, at least 90%, at least 91%, at least 92%, at least 93%, at least 94% or at least 95% or more sequence identity.

Both conventional hybridization and PCR amplification procedures may be utilized to clone sequences encoding ELF3 protein orthologs. Common to these techniques is the hybridization of probes or primers derived from the Arabidopsis ELF3 cDNA or gene sequence to a target nucleotide preparation. This target may be, in the case of conventional hybridization approaches, a cDNA or genomic library or, in the case of PCR amplification, a cDNA or genomic library, or an mRNA preparation.

Direct PCR amplification may be performed on cDNA or genomic libraries prepared from the plant species in question, or RT-PCR may be performed using mRNA extracted from the plant cells using standard methods. PCR primers will comprise at least 15 consecutive nucleotides of the Arabidopsis ELF3 cDNA or gene. One of ordinary skill in the art will appreciate that sequence differences between the Arabidopsis ELF3 cDNA or gene and the target nucleic acid to be amplified may result in lower amplification efficiencies. To compensate for this difference, longer PCR primers or lower annealing temperatures may be used during the amplification cycle. Where lower annealing temperatures are used, sequential rounds of amplification using nested primer pairs may be necessary to enhance amplification specificity.

For conventional hybridization techniques, the hybridization probe is preferably conjugated with a detectable label such as a radioactive label, and the probe is preferably of at least 20 nucleotides in length. As is well known in the art, increasing the length of hybridization probes tends to give enhanced specificity. The labeled probe derived from the Arabidopsis cDNA or gene sequence may be hybridized to a plant cDNA or genomic library and the hybridization signal detected using means known in the art. The hybridizing colony or plaque (depending on the type of library used) is then purified and the cloned sequence contained in that colony or plaque isolated and characterized.

Orthologs of the Arabidopsis ELF3 may alternatively be obtained by immunoscreening an expression library. With the provision herein of the disclosed Arabidopsis ELF3 nucleic acid sequences, the protein may be expressed in and purified from a heterologous expression system (e.g., *E. coli*) and used to raise antibodies (monoclonal or polyclonal) specific for the Arabidopsis ELF3 protein. Antibodies may also be raised against synthetic peptides derived from the Arabidopsis ELF3 amino acid sequence presented herein. Methods of raising antibodies are well known in the art and are described in Harlow and Lane (1988). Such antibodies can be used to screen an expression cDNA library produced from the plant from which it is desired to clone the ELF3 ortholog, using routine methods. The selected cDNAs can be confirmed by sequencing.

c. ELF3 Sequence Variants

With the provision of the Arabidopsis ELF3 protein and ELF3 cDNA and gene sequences herein, the creation of variants of these sequences is now enabled.

Variant ELF3 proteins include proteins that differ in amino acid sequence from the Arabidopsis ELF3 sequence disclosed but which retain ELF3 protein biological activity. Such proteins may be produced by manipulating the nucleotide sequence of the Arabidopsis ELF3 cDNA or gene using standard procedures, including for instance site-directed mutagenesis or PCR. The simplest modifications involve the substitution of one or more amino acids for amino acids having similar biochemical properties. These so-called conservative substitutions are likely to have minimal impact on the activity of the resultant protein. Table 1 shows amino acids that may be substituted for an original amino acid in a protein, and which are regarded as conservative substitutions.

TABLE 1

| Original Residue | Conservative Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

More substantial changes in protein functions or other features may be obtained by selecting amino acid substitutions that are less conservative than those listed in Table 1. Such changes include changing residues that differ more significantly in their effect on maintaining polypeptide backbone structure (e.g., sheet or helical conformation) near the substitution, charge or hydrophobicity of the molecule at the target site, or bulk of a specific side chain. The following substitutions are generally expected to produce the greatest changes in protein properties: (a) a hydrophilic residue (e.g., seryl or threonyl) is substituted for (or by) a hydrophobic residue (e.g., leucyl, isoleucyl, phenylalanyl, valyl or alanyl); (b) a cysteine or proline is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain (e.g., phenylalanine)

is substituted for (or by) one lacking a side chain (e.g., glycine). The effects of these amino acid substitutions, deletions, or additions may be assessed in ELF3 protein derivatives by analyzing the ability of a gene encoding the derivative protein to complement the photoperiod-insensitive flowering and elongated hypocotyl defects in an elf3 mutant. Alternatively, the effect may be examined by studying circadian influenced CAB-luc transcription and/or leaf movement as discussed in Example 2, below.

Variant ELF3 cDNA or genes may be produced by standard DNA mutagenesis techniques, for example, M13 primer mutagenesis. Details of these techniques are provided in Sambrook et al. (1989), Ch. 15. By the use of such techniques, variants may be created which differ in minor ways from the Arabidopsis ELF3 cDNA or gene sequences disclosed, yet which still encode a protein having ELF3 protein biological activity. DNA molecules and nucleotide sequences that are derivatives of those specifically disclosed herein and that differ from those disclosed by the deletion, addition, or substitution of nucleotides while still encoding a protein that has ELF3 protein biological activity are comprehended by this invention. In their most simple form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence such that, while the nucleotide sequence is substantially altered, it nevertheless encodes a protein having an amino acid sequence substantially similar to the disclosed Arabidopsis ELF3 protein sequence. For example, the 23rd amino acid residue of the Arabidopsis ELF3 protein is alanine. This alanine residue is encoded for by the nucleotide codon triplet GCA. Because of the degeneracy of the genetic code, three other nucleotide codon triplets—GCT, GCC and GCG—also code for alanine. Thus, the nucleotide sequence of the Arabidopsis ELF3 ORF could be changed at this position to any of these three alternative codons without affecting the amino acid composition or other characteristics of the encoded protein. Based upon the degeneracy of the genetic code, variant DNA molecules may be derived from the cDNA and gene sequences disclosed herein using standard DNA mutagenesis techniques as described above, or by synthesis of DNA sequences. Thus, this invention also encompasses nucleic acid sequences that encode an ELF3 protein, but which vary from the disclosed nucleic acid sequences by virtue of the degeneracy of the genetic code.

Variants of the ELF3 protein may also be defined in terms of their sequence identity with the prototype ELF3 protein shown in SEQ ID NO: 2. As described above, ELF3 proteins have ELF3 biological activity and share at least 60% sequence identity with the Arabidopsis ELF3 protein. Nucleic acid sequences that encode such proteins may readily be determined simply by applying the genetic code to the amino acid sequence of an ELF3 protein, and such nucleic acid molecules may readily be produced by assembling oligonucleotides corresponding to portions of the sequence.

Nucleic acid molecules that are derived from the Arabidopsis ELF3 cDNA and gene sequences disclosed include molecules that hybridize under stringent conditions to the disclosed prototypical ELF3 nucleic acid molecules, or fragments thereof. Stringent conditions are hybridization at 55° C. in 6×SSC, 5×Denhardt's solution, 0.1% SDS and 100 μg sheared salmon testes DNA, followed by 15–30 minute sequential washes at 55° C. in 2×SSC, 0.1% SDS, followed by 1×SSC, 0.1% SDS and finally 0.2×SSC, 0.1% SDS.

Low stringency hybridization conditions (to detect less closely related homologs) are performed as described above but at 50° C. (both hybridization and wash conditions); however, depending on the strength of the detected signal, the wash steps may be terminated after the first 2×SSC, 0.1% SDS wash.

The Arabidopsis ELF3 gene or cDNA, and orthologs of these sequences from other plants, may be incorporated into transformation vectors and introduced into plants to produce plants with an altered photoperiodic or circadian rhythm phenotype, as described below.

III. Introducing ELF3 into Plants

Once a nucleic acid molecule (e.g, cDNA or gene) encoding a protein involved in the determination of a particular plant characteristic has been isolated, standard techniques may be used to express the cDNA in transgenic plants in order to modify that particular plant characteristic. The basic approach is to clone, for instance, the cDNA into a transformation vector, such that it is operably linked to control sequences (e.g., a promoter) that direct expression of the cDNA in plant cells. The transformation vector is then introduced into plant cells by one of a number of techniques (e.g., electroporation) and progeny plants containing the introduced cDNA are selected. Preferably all or part of the transformation vector will stably integrate into the genome of the plant cell. That part of the transformation vector that integrates into the plant cell and that contains the introduced cDNA and associated sequences for controlling expression (the introduced "transgene") may be referred to as the recombinant expression cassette.

Selection of progeny plants containing the introduced transgene may be based upon the detection of an altered phenotype. Such a phenotype may result directly from the cDNA cloned into the transformation vector or may be manifested as enhanced resistance to a chemical agent (such as an antibiotic) as a result of the inclusion of a dominant selectable marker gene incorporated into the transformation vector.

Successful examples of the modification of plant characteristics by transformation with cloned cDNA sequences are replete in the technical and scientific literature. Selected examples, which serve to illustrate the knowledge in this field of technology, include:

U.S. Pat. No. 5,451,514 (modification of lignin synthesis using antisense RNA and co-suppression);

U.S. Pat. No. 5,750,385 (modification of plant light-, seed- and fruit-specific gene expression using sense and antisense transformation constructs);

U.S. Pat. No. 5,583,021 (modification of virus resistance by expression of plus-sense untranslatable RNA);

U.S. Pat. No. 5,589,615 (production of transgenic plants with increased nutritional value via the expression of modified 2S storage albumins);

U.S. Pat. No. 5,268,526 (modification of phytochrome expression in transgenic plants);

U.S. Pat. No. 5,741,684 (production of plants resistant to herbicides or antibiotics through the use of anti-sense expression);

U.S. Pat. No. 5,773,692 (modification of the levels of chlorophyll by transformation of plants with anti-sense messages corresponding to chlorophyll a/b binding protein);

WO 96/13582 (modification of seed VLCFA composition using over expression, co-suppression and antisense RNA in conjunction with the Arabidopsis FAE1 gene)

These examples include descriptions of transformation vector selection, transformation techniques and the assembly of constructs designed to over-express the introduced nucleic acid, as well as techniques for sense suppression and antisense expression. In light of the foregoing and the provision herein of the Arabidopsis ELF3 cDNA and gene sequences, one of ordinary skill in the art will be able to introduce these nucleic acid molecules, or orthologous, homologous or derivative forms of these molecules, into plants in order to produce plants having altered ELF3 activity. Manipulating the expression of ELF3 in plants will be useful to confer altered circadian clock and/or photoperiodism function. Alteration of the ELF3 protein levels in plants could be used to re-set or customize the circadian clock, for instance in order to alter the plant developmental patterns or photoperiodic responses (e.g., the timing of floral development).

a. Plant Types

The presence of a circadian cycle appears to be universal, occurring not only in all plants thus far examined, but also in insects, including Drosophila (Hall, 1990) and microbes such as *Neurospora crassa* (Dunlap, 1993). At the molecular level, ELF3 homologs have been found in a variety of plant species (see Example 4, below). Thus, expression of the ELF3 protein may be modified in a wide range of higher plants to confer altered circadian clock and/or photoperiodism function, including monocotyledonous and dicotyledenous plants. These include, but are not limited to, Arabidopsis, Cardamine, cotton, tobacco, maize, wheat, rice, barley, soybean, beans in general, rape/canola, alfalfa, flax, sunflower, safflower, brassica, cotton, flax, peanut, clover; vegetables such as lettuce, tomato, cucurbits, cassava, potato, carrot, radish, pea, lentils, cabbage, cauliflower, broccoli, Brussels sprouts, peppers; tree fruits such as citrus, apples, pears, peaches, apricots, walnuts; other trees including poplar, oak, maple, pine, spruce and other conifers; and flowers or other ornamental plants such as carnations, roses, petunias, orchids, impatiens, pansies, lilies, snapdragons, geraniums, and so forth.

b. Vector Construction, Choice of Promoters

A number of recombinant vectors suitable for stable transformation of plant cells or for the establishment of transgenic plants have been described including those described in Pouwels et al., (1987), Weissbach and Weissbach, (1989), and Gelvin et al., (1990). Typically, plant transformation vectors include one or more cloned plant genes (or cDNAs) under the transcriptional control of 5' and 3' regulatory sequences, and at least one dominant selectable marker. Such plant transformation vectors typically also contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Examples of constitutive plant promoters that may be useful for expressing an ELF3 nucleic acid molecule include: the cauliflower mosaic virus (CaMV) 35S promoter, which confers constitutive, high-level expression in most plant tissues (see, e.g., Odel et al., 1985, Dekeyser et al., 1990, Terada and Shimamoto, 1990; Benfey and Chua. 1990); the nopaline synthase promoter (An et al., 1988); and the octopine synthase promoter (Fromm et al., 1989).

A variety of plant gene promoters are regulated in response to environmental, hormonal, chemical, and/or developmental signals, and can be used for expression of the cDNA in plant cells. Such promoters include, for instance, those regulated by: (a) heat (Callis et al., 1988; Ainley, et al. 1993; Gilmartin et al. 1992); (b) light (e.g., the pea rbcS-3A promoter, Kuhlemeier et al., 1989, and the maize rbcS promoter, Schaffner and Sheen, 1991); (c) hormones, such as abscisic acid (Marcotte et al., 1989); (d) wounding (e.g., wun1, Siebertz et al., 1989); and (e) chemicals such as methyl jasminate or salicylic acid (see also Gatz et al., 1997).

Alternatively, tissue specific (root, leaf, flower, or seed, for example) promoters (Carpenter et al. 1992, Denis et al. 1993, Opperman et al. 1993, Stockhause et al. 1997; Roshal et al., 1987; Schernthaner et al., 1988; and Bustos et al., 1989) can be fused to the coding sequence to obtained protein expression in specific organs.

Promoters responsive to the circadian cycle can also be used in plant gene expression vectors. Such promoters include the native ELF3 promoter as described herein, and the promoter from the chlorophyll a/b binding protein (Millar et al. 1992).

Plant transformation vectors may also include RNA processing signals, for example, introns, which may be positioned upstream or downstream of the ORF sequence in the transgene. In addition, the expression vectors may include further regulatory sequences from the 3'-untranslated region of plant genes, e.g., a 3' terminator region to increase mRNA stability of the mRNA, such as the PI-II terminator region of potato or the Agrobacterium octopine or nopaline synthase 3' terminator regions. The 3' region of the ELF3 gene can also be used.

Finally, as noted above, plant transformation vectors may include dominant selectable marker genes to allow for the ready selection of transformants. Such genes include those encoding antibiotic resistance genes (e.g., resistance to hygromycin, kanamycin, bleomycin, G418, streptomycin or spectinomycin) and herbicide resistance genes (e.g., phosphinothricin acetyltransferase).

c. Arrangement of ELF3 Sequence in the Vector

The particular arrangement of the ELF3 sequence in the transformation vector will be selected according to the type of expression of the sequence that is desired.

Where enhanced ELF3 protein activity is desired in the plant, an ELF3 ORF may be operably linked to a constitutive high-level promoter such as the CaMV 35S promoter. As noted below, modification of ELF3 synthesis may also be achieved by introducing into a plant a transformation vector containing a variant form of an ELF3 cDNA or gene.

In contrast, a reduction of ELF3 activity in the transgenic plant may be obtained by introducing into plants an antisense construct based on an ELF3 cDNA or gene sequence. For antisense suppression, an ELF3 cDNA or gene is arranged in reverse orientation relative to the promoter sequence in the transformation vector. The introduced sequence need not be a full length ELF3 cDNA or gene, and need not be exactly homologous to the native ELF3 cDNA or gene found in the plant type to be transformed. Generally, however, where the introduced sequence is of shorter length, a higher degree of homology to the native ELF3 sequence will be needed for effective antisense suppression. The introduced antisense sequence in the vector generally will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous ELF3 gene in the plant cell. Although the exact mechanism by which antisense RNA molecules interfere with gene expression has not been elucidated, it is believed that antisense RNA molecules bind to the endogenous mRNA molecules and thereby inhibit translation of the endogenous mRNA. The production and use of anti-sense constructs are disclosed, for instance, in U.S. Pat. No. 5,773,692 (using constructs encoding anti-sense RNA for chlorophyll a/b binding protein to reduce plant chlorophyll content), and U.S. Pat. No. 5,741,684 (regulating the fertility of pollen in various plants through the use of anti-sense RNA to genes involved in pollen development or function).

Suppression of endogenous ELF3 gene expression can also be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haseloff. Inclusion of ribozyme sequences within antisense RNAs may be used to confer RNA cleaving activity on the antisense RNA, such that endogenous mRNA molecules that bind to the antisense RNA are cleaved, leading to an enhanced antisense inhibition of endogenous gene expression.

Constructs in which an ELF3 cDNA or gene (or variants thereof) are over-expressed may also be used to obtain co-suppression of the endogenous ELF3 gene in the manner described in U.S. Pat. No. 5,231,021 to Jorgensen. Such co-suppression (also termed sense suppression) does not require that the entire ELF3 cDNA or gene be introduced into the plant cells, nor does it require that the introduced sequence be exactly identical to the endogenous ELF3 gene. However, as with antisense suppression, the suppressive efficiency will be enhanced as (1) the introduced sequence is lengthened and (2) the sequence similarity between the introduced sequence and the endogenous ELF3 gene is increased.

Constructs expressing an untranslatable form of an ELF3 mRNA may also be used to suppress the expression of endogenous ELF3 activity. Methods for producing such constructs are described in U.S. Pat. No. 5,583,021 to Dougherty et al. Preferably, such constructs are made by introducing a premature stop codon into an ELF3 ORF.

Finally, dominant negative mutant forms of the disclosed sequences may be used to block endogenous ELF3 activity. Such mutants require the production of mutated forms of the ELF3 protein that interact with the same molecules as ELF3 but do not have ELF3 activity.

d. Transformation and Regeneration Techniques

Transformation and regeneration of both monocotyledonous and dicotyledonous plant cells is now routine, and the most appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; microinjection of plant cells; micro-projectile bombardment of plant cells; vacuum infiltration; and *Agrobacterium tumefaciens* (AT) mediated transformation. Typical procedures for transforming and regenerating plants are described in the patent documents listed at the beginning of this section. ps
e. Selection of Transformed Plants Following transformation and regeneration of plants with the transformation vector, transformed plants are usually selected using a dominant selectable marker incorporated into the transformation vector. Typically, such a marker will confer antibiotic resistance on the seedlings of transformed plants, and selection of transformants can be accomplished by exposing the seedlings to appropriate concentrations of the antibiotic.

After transformed plants are selected and grown to maturity, they can be assayed using the methods described herein to determine whether the circadian cycle or photoperiodism of the transformed plant has been altered as a result of the introduced transgene.

IV. Production of Recombinant ELF3 Protein in Heterologous Expression Systems

Many different expression systems are available for expressing cloned nucleic acid molecules. Examples of prokaryotic and eukaryotic expression systems that are routinely used in laboratories are described in Chapters 16–17 of Sambrook et al. (1989). Such systems may be used to express ELF3 at high levels to facilitate purification of the protein. The purified ELF3 protein may be used for a variety of purposes. For example, the purified recombinant enzyme may be used as an immunogen to raise anti-ELF3 antibodies. Such antibodies are useful as both research reagents (such as in the study of circadian clock and photoperiodism mechanisms in plants) as well as diagnostically to determine expression levels of the protein in plants that are being developed for agricultural or other use. Thus, the antibodies may be used to quantify the level of ELF3 protein both in non-transgenic plant varieties and in transgenic varieties that are designed to over-express or under-express the ELF3 protein. Such quantification may be performed using standard immunoassay techniques, such as ELISA and in situ immunofluorescence and others described in Harlow & Lane (1988).

By way of example only, high level expression of the ELF3 protein may be achieved by cloning and expressing the ELF3 cDNA in yeast cells using the pYES2 yeast expression vector (INVITROGEN, Carlsbad, Calif.). Alternatively, a genetic construct may be produced to direct secretion of the recombinant ELF3 protein from yeast cells into the growth medium. This approach will facilitate the purification of the ELF3 protein, if this is necessary. Secretion of the recombinant protein from the yeast cells may be achieved by placing a yeast signal sequence adjacent to the ELF3 coding region. A number of yeast signal sequences have been characterized, including the signal sequence for yeast invertase. This sequence has been successfully used to direct the secretion of heterologous proteins from yeast cells, including such proteins as human interferon (Chang et al., 1986), human lactoferrin (Liang and Richardson, 1993) and prochymosin (Smith et al., 1985).

Alternatively, the enzyme may be expressed at high level in prokaryotic expression systems, such as *E. coli*, as described in Sambrook et al. (1989). Commercially available prokaryotic expression systems include the pBAD expression system and the ThioFusion expression system (INVITROGEN, Carlsbad, Calif.).

V. ELF3 Promoter

The 5' regulatory region of the ELF3 gene is also provided herein (SEQ ID NO: 5). This regulatory region confers ELF3-like circadian rhythm-based expression on open reading frames to which it is operably linked. Approximately 4 kb of the ELF3 5' regulatory region is provided in SEQ ID NO: 5. While this entire ca. 4 kb regulatory sequence may be employed, one of ordinary skill in the art will appreciate that less than this entire sequence may be sufficient to confer ELF3-like circadian rhythm expression. For example, sequences comprising nucleotides 1–4071 of SEQ ID NO: 5 or shorter sequences such as those spanning nucleotides 500–4071, 1000–4071, 1500–4071, 2000–4071, 2500–4071, 3000–4071, 3500–4071 and 4000–4071 may be employed. One embodiment of an ELF3 promoter is about nucleotides 1 through about 1900 of the 5' upstream region shown in SEQ ID NO: 5. Other particular embodiments include about nucleotides 50–1900, 150–1900, 250–1900, 350–1900, 450–1900, 550–1900 and so forth.

Sequences as short as 50 or 100 nucleotides from within the 5' regulatory region of ELF3 may also be employed. The determination of whether a particular sub-region of the disclosed sequence operates to confer effective ELF3-like circadian rhythm expression in a particular system (taking into account the plant species into which the construct is being introduced, the level of expression required, etc.) will be performed using known methods. These include, for instance, operably linking the promoter sub-region to a marker gene (e.g. GUS or luciferase), introducing such constructs into plants, and determining the level of expression of the marker gene.

The present invention therefore facilitates the production, by standard molecular biology techniques, of nucleic acid molecules comprising this promoter sequence operably linked to a nucleic acid sequence, such as an open reading frame. Suitable open reading frames include open reading frames encoding any protein for which ELF3-like circadian rhythm expression is desired.

EXAMPLES

Example 1
Cloning Arabidopsis ELF3

The ELF3 gene was isolated by map-based positional cloning. Molecular markers tightly linked to the ELF3 gene were identified by random fragment length polymorphism (RFLP) analysis, and a high resolution genetic map of the locus was constructed. The region containing the ELF3 gene was narrowed down to 30 kb contained on a single bacterial artificial chromosome (BAC). This BAC was sequenced, and cDNAs with homology to sequences within the BAC were isolated from a variety of cDNA libraries. The ELF3 sequence was further localized by complementation experiments to a 10 kb subcloned fragment contained within the BAC. Identification of the appropriate gene within the subcloned fragment was confirmed through isolation and sequencing of elf3 alleles from various Arabidopsis elf3 mutants.

The isolated ELF3 gene (SEQ ID NO: 3) has no significant sequence similarity to other DNA or protein sequences with assigned function. However, a published EST (GenBank #N96569; Newman et al., 1994) overlaps nucleotide 1235–2501 of the corresponding cDNA (SEQ ID NO: 1). ELF3 has four exons, and is transcribed as an mRNA of about 2.4 kb in Arabidopsis seedlings and in mature leaves. The putative protein (SEQ ID NO: 2) encoded by the ELF3 ORF (SEQ ID NO: 4) is 695 amino acids in length and has a predicted molecular weight of approximately 80 KDa.

Research by this group has recently identified several putative ELF3 orthologs from other plant species, including *Cardamine oligosperma,* tomato, rice, and maize (see Examples 4 and 5, below). GenBank accession numbers for ELF3 and putative ELF3 homologs identified as such by this research group are as follows: AtELF3 (*A. thaliana* genomic DNA: AC004747, published Dec. 17, 1999), AtEEC (*A. thaliana* genomic DNA: AB023045, published Nov. 20, 1999), cELF3 (yet to be submitted), tELF3 [*Lycopersicon esculentum* Expressed Sequence Tags (ESTs) from Clemson University Genomics Institute: AW093790 (Oct. 18, 1999), AI894513 (Jul. 27, 1999), AI488927 (Jun. 29, 1999), AI486934 (Jun. 29, 1999), AI894398 (Jul. 27, 1999)], rELF3 (*Oryza sativa* genomic DNA: AP000399, published Dec. 3, 1999), and mELF3 (*Zea mays* EST from Stanford University Genome Center: AI637184, published Apr. 26, 1999).

Example 2
Analysis of ELF3 Phenotype

Sensitive assays for monitoring circadian rhythm responses in Arabidopsis have been developed (Millar and Kay, 1991; Millar et al., 1992). One assay system is based on the observation that the transcription of the chlorophyll a/b binding protein gene, CAB2, cycles on a 24-hour period. Transcription from the CAB2 promoter increases prior to subjective dawn, peaks in late morning, and falls to a low level late in the day (Millar and Kay, 1991). Cycling of CAB mRNA continues under constant light conditions. In order to follow expression in vivo, the CAB2 promoter has been fused to the gene encoding firefly luciferase (luc), and this fusion has been transformed in wild-type Arabidopsis (Millar et al., 1992). Transcriptional expression from the CAB2-luc fusion construct is monitored by imaging single transgenic seedlings using a low-light video camera and a photon-counting image processor; the results from imaging the CAB2-luc fusion is comparable to the transcriptional expression of the endogenous CAB2 gene. With this system, over one hundred individual seedlings can be imaged every 30 minutes, thus allowing the collection of thousands of data points in less than one week. This very powerful system has recently been used to characterize several known photomorphogenic Arabidopsis mutants (Millar et al., 1995a) and to isolate a short-period mutant of Arabidopsis (Millar et al., 1995b). Elf3 mutants examined using this system are defective in circadian regulated CAB2 transcription (Hicks et al., 1996).

An automatic video imaging system can also be used to monitor a second circadian regulated process, leaf movement (Millar and Kay, 1991). Plant leaves turn down (open) during the day and turn up (closed) during the night in a circadian fashion. Arabidopsis seedlings display this circadian leaf movement in constant light, and this can be assayed and quantified using a relatively inexpensive video and computer system (Millar and Kay, 1991). The analysis of leaf movements provides an independent circadian regulated process with which to evaluate potential circadian rhythm mutants (see, for instance, Schaffer et al. 1998, using leaf movement to analyze circadian cycle disruption in late elongated hypocotyl (lhy) mutants in Arabidopsis). Elf3 mutants are also defective in circadian regulated leaf movements.

These assays may be used to assess the effect that modifying ELF3 protein expression level (e.g., through introduction of ELF3 antisense or sense constructs into plants) has on plant phenotype.

Example 3
Introducing ELF3 Sequences into Plants
Plasmid Construction

Arabidopsis ELF3 cDNA (SEQ ID NO: 1) and full-length genomic (SEQ ID NO: 3) sequences were used in the construction of over-expression and antisense vectors. These sequences were operably linked to the CaMV 35S (constitutive) promoter, in both the sense and antisense orientations, and cloned using standard molecular biology techniques into pSJL4 (Jones et al. 1992).

The over-expression and antisense expression cassettes were removed from the above vectors and inserted into pMON505 for Agrobacterium-mediated plant transformation.

Plant Transformation

Wild-type and elf3 mutant Arabidopsis plants (ecotype Columbia) were transformed using standard in planta Agrobacterium-mediated techniques (Chang et al. 1994, Katavic et al. 1994). Transformed seeds were selected on kanamycin, and Kan$^R$ seedlings transferred to soil and grown for further analysis.

Over-expression of ELF3 protein in elf3 mutant plants comprising the ELF3 genomic gene sequence as the transgene resulted in full complementation of the elf3 mutant phenotype in some transformed plants. In some instances, over-expression of ELF3 protein from cDNA-based transgenes in wild-type plants produced elf3 mutant-like plants or plants having intermediate phenotype; this is probably the result of co-suppression. Antisense expression of the full-length ELF3 cDNA in wild-type plants produced some transformants with an elf3 mutant-like phenotype.

Example 4
ELF3 Orthologs

As noted above, orthologs of ELF3 exist in a number of plant species including corn, tomato and tobacco. The existence of these sequences may be demonstrated by hybridization techniques, such as Southern blotting. Hybridization was performed using a probe based on the entire ELF3 cDNA sequence (SEQ ID NO: 1). This probe was hybridized to genomic DNA from Arabidopsis, Chlamydomonas, Douglas fir, corn, rice, poplar, tobacco, and tomato. High stringency hybridization was performed at 55° C. in 6×SSC, 5×Denhardt's solution, 0.1% SDS and 100 μg sheared salmon testes DNA, followed by 15–30 minute sequential washes at 55° C. in 2×SSC, 0.1% SDS, followed by 1×SSC, 0.1% SDS and finally 0.2×SSC, 0.1% SDS. A single, clean hybridizing band was observed on the Southern blot in Arabidopsis, rice, and tobacco genomic DNA preparations.

Lower stringency hybridization conditions were used to detect less closely related ELF3 homologs. Such hybridization was performed at 50° C. for 24 hours in the hybridization solution described above, followed by washing in 2×SSC, 0.1% SDS at 50° C. for 3 hours, with five sequential changes of wash solution. Hybridization of full length cDNA probe under low stringency hybridization conditions detected ELF3 homologs (indicated by one or more bands on the Southern) in Arabidopsis, Chlamydomonas, Douglas fir, corn, rice, poplar, tobacco, and tomato and other plant species.

Once an ELF3-hybridizing band is detected in a plant species, standard techniques such as screening cDNA or genomic libraries from the plant with the ELF3 probe may be used. Alternatively, ELF3 homologs may be isolated by screening an expression library from the plant in question using a ELF3 protein specific binding agent, such as an anti-ELF3 antibody produced as described above. Such homologs may be introduced into plants using the methods described above in order to produce altered circadian rhythm and/or photoperiodic phenotypes.

It is also possible to use primers complementary to the Arabidopsis ELF3 sequence to amplify orthologous nucleic acid sequences. For example, an ELF3 ortholog has been isolated in this manner from a Cardamine genomic DNA preparation, using the following PCR amplification primers:

primer 5: 5' ATGAAGAGAGGGAAAGATGAG
G 3' (SEQ ID NO:10)

primer 6: 5' GCCACCATCTCGGTATAACC 3' (SEQ ID NO: 11).

Degenerate mixtures of oligonucleotides may also be used to amplify orthologous nucleic acid sequences. The construction of degenerate oligonucleotides is well known to one of ordinary skill in the art.

Nucleotide sequences from C. oligosperma (a member of the family Brassicaceae) were obtained by sequencing polymerase chain reaction products using degenerate oligonucleotides to the Arabidopsis ELF3 gene and genomic DNA or cDNA prepared from C. oligosperma seedlings using standard techniques. The sequence of the amplified Cardamine ELF3 ortholog (cELF3) is shown in SEQ ID NO: 12.

Example 5
Consensus Sequences Within the ELF3 Protein and Homologs Thereof

Computerized, searchable databases were searched for sequences having significant homology the Arabidopsis ELF3 cDNA and genomic nucleotide sequences depicted herein, and the Cardamine ELF3 ortholog nucleotide sequence (SEQ ID NO: 12).

This search yielded several putative ELF3 homologs. GenBank accession numbers for ELF3 and the putative ELF3 homologs identified as such by this research group are as follows: AtELF3 (*A. thaliana* genomic DNA: AC004747), AtEEC (*A. thaliana* genomic DNA: AB023045), cELF3 (yet to be submitted), tELF3 (*Lycopersicon esculentum* Expressed Sequence Tags (ESTs) from Clemson University Genomics Institute: AW093790, AI894513, AI488927, AI486934, AI894398), rELF3 (*Oryza sativa* genomic DNA: AP000399), mELF3 (*Zes mays* EST from Stanford University Genome Center: AI637184).

Multiple sequence alignment of the ELF3 proteins (FIGS. 1 and 2) shows four highly conserved regions within ELF3 and putative ELF3 homologs from *Arabidopsis thaliana* (Essence of ELF3 Consensus, EEC) and other plant species (*Cardamine oligosperma*, tomato, rice, and maize) (FIG. 2). Sequences were aligned and analyzed using CLUSTAL W (Thompson et al., *Nucleic Acids Res.* 22, 4673–80, 1994) and PrettyBox (Genetics Computer Group, Inc.). Protein designations are given on the left. Amino acid residues are numbered on both the left and right. Residues shaded in black indicate identity of at least three ELF3/ELF3-related sequences in the alignment; light-shaded residues indicate similarity to consensus.

The foregoing examples are provided by way of illustration only. One of skill in the art will appreciate that numerous variations on the biological molecules and methods described above may be employed to make and use the ELF3 gene, corresponding protein, and promoter region. We claim all such subject matter that falls within the scope and spirit of the following claims.

REFERENCES

Ainley et al. (1993) *Plant Mol. Biol.* 22:13–23.
Altschul et al. (1990). *J. Mol. Biol.*, 215, 403–10
Altschul et al. (1994). *Nature Genet.*, 6, 119–29.
An et al. (1988) *Plant Physiol.* 88:547.
Aronson et al. (1994) *Science* 263:1578–1584.
Ausubel et al. (1987) In *Current Protocols in Molecular Biology*, Greene Publishing Associates and Wiley-Intersciences.
Benfey and Chua (1990) *Science* 250:959–966.
Bernier (1988) *Ann. Rev. Plant Phys. and Plant Mol. Bio.* 39:175–219.
Bustos et al. (1989) *Plant Cell* 1:839.
Callis et al. (1988) *Plant Physiol.* 88:965.
Carpenter et al. (1992) *The Plant Cell* 4:557–571.
Chang et al. (1994) *Plant J.* 5:551–558.
Chang et al. (1986) *Mol. And Cell. Biol.* 6:1812–1819.

Corpet et al. (1988). *Nucleic Acids Research* 16, 10881–90.
Dekeyser et al. (1990) *Plant Cell* 2:591.
Denis et al. (1993) *Plant Physiol.* 101:1295–1304.
Dunlap (1993) *Annu. Rev. Physiol* 55:683.
Edery et al. (1994) *Science* 263:237–240.
Fromm et al. (1989) *Plant Cell* 1:977.
Gatz et al. (1997) *Ann. Rev. Plant Physiol Plant Mol. Biol.* 48:89–108.
Gelvin et al. (1990) *Plant Molecular Biology Manual*, Kluwer Academic Publishers.
Gilmartin et al. (1992) *The Plant Cell* 4:839–949.
Hall (1990) *Ann. Rev. Genet.* 24:659.
Harlow & Lane (1988) *Antibodies, A Laboratory Manual*, Cold Spring Harbor Laboratory, New York.
Hicks et al. (1996) *Science* 274(5288):790–792.
Higgins and Sharp (1988). *Gene*, 73: 237–244.
Higgins and Sharp (1989). *CABIOS* 5: 151–153.
Huang et al. (1992). *Computer Applications in the Biosciences* 8,155–65.
Hülskamp et al. (1990) *Nature* 346:577–580.
Innis et al. (eds.) (1990) *PCR Protocols, A Guide to Methods and Applications*, Academic Press, Inc., San Diego, Calif.
Jones et al. (1992) *Transgenic Res.* 1:285–297.
Katavic et al. (1994) *Mol. Gen. Genet.* 245:363–370.
Koornneef et al. (1991) *Mol. Gen. Genet.* 229:57–66.
Kuhlemeier et al. (1989) *Plant Cell* 1: 471.
Lambie and Kimble (1991) *Development* 112:231–240.
Liang & Richardson (1993) *J. Agric. Food Chem.* 41:1800–1807.
Marcotte et al. (1989) *Plant Cell* 1:969.
Millar et al. (1995a) *Science* 267(5201):1163–1166.
Millar et al. (1995b) *Science* 267(5201): 1161–1163.
Millar et al. (1992) *Plant Cell* 4:1075–1087.
Millar and Kay (1991) *Plant Cell* 3:541–550.
Mozo et al. (1998) *Mo. Gen. Genet.* 258(5):562–570.
Murfet (1985) *Pisum sativum.* In *Handbook of Flowering Plants Vol. IV*, ed. A. H. Halevy. (CRC Press: Boca Raton, Fla.), pp. 97–126.
Needleman and Wunsch (1970). *J. Mol. Biol.* 48: 443.
Newman et al. (1994) *Plant Physiol.* 106(4):1241–1255.
Odel et al. (1985) *Nature* 313:810.
Opperman et al. (1993) *Science* 263:221–223.
Pearson and Lipman (1988). *Proc. Natl. Acad Sci. USA* 85: 2444.
Pearson et al. (1994). *Methods in Molecular Biology* 24, 307–31.
Pouwels et al. (1987) *Cloning Vectors: A Laboratory Manual*, 1985, supp.
Roshal et al. (1987) *EMBO J.* 6:1155.
Sambrook et al. (1989) *In Molecular Cloning: A Laboratory Manual*, Cold Spring Harbor, New York.
Schaffer et al. (1998) *Cell* 93:1219–1229.
Schaffner & Sheen (1991) *Plant Cell* 3:997.
Schemthaner et al. (1988) *EMBO J.* 7:1249.
Shannon and Meeks-Wagner (1991) *Plant Cell* 3:877–892.
Siebertz et al. (1989) *Plant Cell* 1:961.
Smith et al. (1985) *Science* 229:1219–1224.
Smith and Waterman (1981). *Adv. Appl. Math.* 2: 482.
Stockhause et al. (997) *The Plant Cell* 9:479–489.
Terada & Shimamoto (1990) *Mol. Gen. Genet.* 220:389.
Tijssen (1993). *Laboratory Techniques in Biochemistry and Molecular Biology—Hybridization with Nucleic Acid Probes* Part I, Chapter 2 "Overview of principles of hybridization and the strategy of nucleic acid probe assays", Elsevier, N.Y.
Wang & Tobin (1998) *Cell* 93:1207–1217.
Weissbach & Weissbach (1989) *Methods for Plant Molecular Biology*, Academic Press.
Zagotta et al. (1992) *Aust. J. Plant Physiol.* 19:411–418.
Zagotta et al. (1996) *Plant J.* 10(4):691–702.

---

We claim:

1. A recombinant nucleic acid molecule comprising a promoter operably linked to an open reading fame, wherein the promoter is an Arabidopsis EARLY-FLOWERING 3 (ELF3) promoter.

2. The nucleic acid molecule of claim 1 wherein the promoter comprises a sequence selected from the group consisting of:

(a) SEQ ID NO: 5; and
(b) nucleotides 2000–4071 of SEQ ID NO: 5.

3. The nucleic acid molecule of claim 1 wherein the promoter comprises the sequence shown in SEQ ID NO: 5.

4. The nucleic acid molecule of claim 1 wherein the promoter comprises the sequence shown in nucleotides 2000–4071 of SEQ ID NO: 5.

5. The nucleic acid molecule of claim 1, wherein the open-reading frame comprises a nucleotide sequence that encodes a protein for which ELF3-like circadian rhythm-based expression is desired.

6. The nucleic acid molecule of claim 1, wherein the open-reading frame comprises a nucleotide sequence of a marker gene.

7. The nucleic acid molecule of claim 6, wherein the marker gene comprises an antibiotic resistance gene, an herbicide resistance gene, a beta-glucuronidase gene, or a luciferase gene.

8. A cell transformed with the recombinant nucleic acid molecule of claim 1.

9. The cell of claim 8, wherein the cell is a plant cell and the plant cell is from a plant selected from the group consisting of Arabidopsis, Cardamine, pepper, tomato, carrot, tobacco, broccoli, cauliflower, cabbage, canola, beans soybean, rice, corn, wheat, barley, flax, citrus, cotton, cassava, walnut, a conifer, and an ornamental plant.

10. The cell of claim 8, wherein the cell is transformed using electroporation, lipofection, particle gun acceleration, viral transfection, Agrobacterium-mediated transformation, or a combination thereof.

11. A transgenic plant comprising the recombinant nucleic acid molecule of claim 1.

12. The transgenic plant of claim 11, wherein the plant is selected from the group consisting of Arabidopsis, Cardamine, pepper, tomato, carrot, tobacco, broccoli, cauliflower, cabbage, canola, bean, soybean, rice, corn, wheat, barley, flax, citrus, cotton, cassava, walnut, a conifer, and an ornamental plant.

* * * * *

UNITED STATES PATENT AND TRADEMARK OFFICE
CERTIFICATE OF CORRECTION

| | |
|---|---|
| PATENT NO. | : 6,433,251 B1 |
| APPLICATION NO. | : 09/513057 |
| DATED | : August 13, 2002 |
| INVENTOR(S) | : Wagner et al. |

It is certified that error appears in the above-identified patent and that said Letters Patent is hereby corrected as shown below:

On the Title Page item [56], second Col. line 42,

Under OTHER PUBLICATIONS:

"Zagotta et al., 'The Arabidopsis ELF3 gene regulates vegetative photomorphogenesis and the photoperiodic induction of floweirng,'..." should read --Zagotta et al., 'The Arabidopsis ELF3 gene regulates vegetative photomorphogenesis and the photoperiodic induction of flowering,'...--

In the Specification

Column 3, line 47, "50°C.," should read --50°C,--.

Column 4, line 43, "*Zes*" should read --*Zea*--.

Column 5, lines 47-48, "SEQ ID NO: 20 shows the DNA (also referred to as BROCCA~1) a sequence of the" should be deleted.

Column 5, line 50, "BROCCA~1) a sequence of the *Lycopersicon*..." should read --BROCCA~1) sequence of the *Lycopersicon*...--.

Column 6, lines 8, 11, 14, and 18, "*Zes*" should read --*Zea*--.

Column 6, line 52, "SFQ ID NO: 1" should read --SEQ ID NO: 1--.

Column 12, line 2, "escutentum" should read --esculentum--.

Column 15, line 34, "encoded for by the" should read -- encode by the--.

Column 19, line 62, "...of this section. ps" should read --... of this section.--.

Column 24, line 29, "*Zes*" should read --*Zea*--.

Column 26, line 19, "Schemthaner" should read --Schernthaner--.

UNITED STATES PATENT AND TRADEMARK OFFICE
CERTIFICATE OF CORRECTION

PATENT NO. : 6,433,251 B1
APPLICATION NO. : 09/513057
DATED : August 13, 2002
INVENTOR(S) : Wagner et al.

It is certified that error appears in the above-identified patent and that said Letters Patent is hereby corrected as shown below:

In the Claims:

Column 113, line 64, Claim 1, "fame" should read --frame--.

Column 116, line 3, Claim 9, "beans soybean" should read --bean, soybean--.

Signed and Sealed this

Ninth Day of January, 2007

JON W. DUDAS
*Director of the United States Patent and Trademark Office*

UNITED STATES PATENT AND TRADEMARK OFFICE
CERTIFICATE OF CORRECTION

PATENT NO.       : 6,433,251 B1
APPLICATION NO.  : 09/513057
DATED            : August 13, 2002
INVENTOR(S)      : Wagner et al.

It is certified that error appears in the above-identified patent and that said Letters Patent is hereby corrected as shown below:

On the Title Page item [56], second Col. line 42,

Under OTHER PUBLICATIONS:

"Zagotta et al., 'The Arabidopsis ELF3 gene regulates vegetative photomorphogenesis and the photoperiodic induction of floweirng,'..." should read --Zagotta et al., 'The Arabidopsis ELF3 gene regulates vegetative photomorphogenesis and the photoperiodic induction of flowering,'...--

In the Specification

Column 3, line 47, "50°C.," should read --50°C,--.

Column 4, line 43, "*Zes*" should read --*Zea*--.

Column 5, lines 47-48, "SEQ ID NO: 20 shows the DNA (also referred to as BROCCA~1) a sequence of the" should be deleted.

Column 5, line 50, "BROCCA~1) a sequence of the *Lycopersicon*..." should read --BROCCA~1) sequence of the *Lycopersicon*...--.

Column 6, lines 8, 11, 14, and 18, "*Zes*" should read --*Zea*--.

Column 6, line 52, "SFQ ID NO: 1" should read --SEQ ID NO: 1--.

Column 12, line 2, "escutentum" should read --esculentum--.

Column 15, line 34, "encoded for by the" should read -- encoded by the--.

Column 19, line 62, "...of this section. ps" should read --... of this section.--.

Column 24, line 29, "*Zes*" should read --*Zea*--.

Column 26, line 19, "Schemthaner" should read --Schernthaner--.

UNITED STATES PATENT AND TRADEMARK OFFICE
CERTIFICATE OF CORRECTION

PATENT NO. : 6,433,251 B1
APPLICATION NO. : 09/513057
DATED : August 13, 2002
INVENTOR(S) : Wagner et al.

It is certified that error appears in the above-identified patent and that said Letters Patent is hereby corrected as shown below:

In the Claims:

Column 113, line 64, Claim 1, "fame" should read --frame--.

Column 116, line 3, Claim 9, "beans soybean" should read --bean, soybean--.

This certificate supersedes Certificate of Correction issued January 9, 2007.

Signed and Sealed this

Twenty-seventh Day of November, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,433,251 B1 | Page 1 of 1 |
| APPLICATION NO. | : 09/513057 | |
| DATED | : August 13, 2002 | |
| INVENTOR(S) | : Wagner et al. | |

It is certified that error appears in the above-identified patent and that said Letters Patent is hereby corrected as shown below:

In the Specification, insert at Column 1, line 12:

--ACKNOWLEDGMENT OF GOVERNMENT SUPPORT

This invention was made with government support under Grant No. MCB9507218 awarded by the National Science Foundation. The government has certain rights in the invention.--

Signed and Sealed this

Eighth Day of November, 2011

David J. Kappos
*Director of the United States Patent and Trademark Office*

SEQUENCE LISTING

```
<160> NUMBER OF SEQ ID NOS: 35

<210> SEQ ID NO 1
<211> LENGTH: 2518
<212> TYPE: DNA
<213> ORGANISM: Arabidopsis thaliana
<220> FEATURE:
<221> NAME/KEY: CDS
<222> LOCATION: (284)..(2371)
<223> OTHER INFORMATION:

<400> SEQUENCE: 1
tgaaaactca ctttggtttt gtttgattcc tctttagtct gttttcgat  ttcgttttct      60 ctgattggtt tggtggtgag atctctatcg tagtttgtcc tttgggttaa gatatttcat     120
ttgattggtg ggtttgtttt attgaagctt attgttgtga aagttggagt ctttctcagt     180
ttttaggttg aattattaag agaaagggaa gatttttggt gtgaagttag gttatttggg     240
gtttgagaag tttgcaagtg aaaaaggttg tgaattgtga gtg atg aag aga ggg      295
                                                Met Lys Arg Gly
                                                  1 aaa gat gag gag aag ata ttg gaa cct atg ttt cct cgg ctt cat gtg      343
Lys Asp Glu Glu Lys Ile Leu Glu Pro Met Phe Pro Arg Leu His Val
  5                  10                  15                  20 aat gat gca gat aaa gga ggg cct aga gct cct cct aga aac aag atg      391
Asn Asp Ala Asp Lys Gly Gly Pro Arg Ala Pro Pro Arg Asn Lys Met
```

|  |  |  |  |  |  |  |  |  |  |  |  |  |  |  |  |
|---|---|---|---|---|---|---|---|---|---|---|---|---|---|---|---|
|  |  |  |  | 25 |  |  |  | 30 |  |  |  | 35 |  |  |  |
| gct | ctt | tat | gag | cag | ctt | agt | att | cct | tct | cag | agg | ttt | ggt | gat | cat | 439 |
| Ala | Leu | Tyr | Glu | Gln | Leu | Ser | Ile | Pro | Ser | Gln | Arg | Phe | Gly | Asp | His |  |
|  |  |  | 40 |  |  |  |  | 45 |  |  |  |  | 50 |  |  |  |
| gga | acg | atg | aat | tct | cgt | agt | aac | aac | aca | agc | act | ttg | gtt | cat | cct | 487 |
| Gly | Thr | Met | Asn | Ser | Arg | Ser | Asn | Asn | Thr | Ser | Thr | Leu | Val | His | Pro |  |
|  |  | 55 |  |  |  |  | 60 |  |  |  |  | 65 |  |  |  |  |
| gga | cca | tct | agt | cag | cct | tgt | ggt | gtg | gaa | aga | aac | tta | tct | gtc | cag | 535 |
| Gly | Pro | Ser | Ser | Gln | Pro | Cys | Gly | Val | Glu | Arg | Asn | Leu | Ser | Val | Gln |  |
|  | 70 |  |  |  |  | 75 |  |  |  |  | 80 |  |  |  |  |  |
| cat | ctt | gat | tct | tca | gcc | gca | aac | caa | gca | act | gag | aag | ttt | gtc | tcc | 583 |
| His | Leu | Asp | Ser | Ser | Ala | Ala | Asn | Gln | Ala | Thr | Glu | Lys | Phe | Val | Ser |  |
| 85 |  |  |  |  | 90 |  |  |  |  | 95 |  |  |  |  | 100 |  |
| caa | atg | tcc | ttc | atg | gaa | aat | gtg | aga | tct | tcg | gca | cag | cat | gat | cag | 631 |
| Gln | Met | Ser | Phe | Met | Glu | Asn | Val | Arg | Ser | Ser | Ala | Gln | His | Asp | Gln |  |
|  |  |  |  | 105 |  |  |  |  | 110 |  |  |  |  | 115 |  |  |
| agg | aaa | atg | gtg | aga | gag | gaa | gaa | gat | ttt | gca | gtt | cca | gta | tat | att | 679 |
| Arg | Lys | Met | Val | Arg | Glu | Glu | Glu | Asp | Phe | Ala | Val | Pro | Val | Tyr | Ile |  |
|  |  |  | 120 |  |  |  |  | 125 |  |  |  |  | 130 |  |  |  |
| aac | tca | aga | aga | tct | cag | tct | cat | ggc | aga | acc | aag | agt | ggt | att | gag | 727 |
| Asn | Ser | Arg | Arg | Ser | Gln | Ser | His | Gly | Arg | Thr | Lys | Ser | Gly | Ile | Glu |  |
|  |  | 135 |  |  |  |  | 140 |  |  |  |  | 145 |  |  |  |  |
| aag | gaa | aaa | cac | acc | cca | atg | gtg | gca | cct | agc | tct | cat | cac | tcc | att | 775 |
| Lys | Glu | Lys | His | Thr | Pro | Met | Val | Ala | Pro | Ser | Ser | His | His | Ser | Ile |  |
|  | 150 |  |  |  |  | 155 |  |  |  |  | 160 |  |  |  |  |  |
| cga | ttt | caa | gaa | gtg | aat | cag | aca | ggc | tca | aag | caa | aac | gta | tgt | ttg | 823 |
| Arg | Phe | Gln | Glu | Val | Asn | Gln | Thr | Gly | Ser | Lys | Gln | Asn | Val | Cys | Leu |  |
| 165 |  |  |  |  | 170 |  |  |  |  | 175 |  |  |  |  | 180 |  |
| gct | act | tgt | tca | aaa | cct | gaa | gtt | agg | gat | cag | gtc | aag | gcg | aat | gca | 871 |
| Ala | Thr | Cys | Ser | Lys | Pro | Glu | Val | Arg | Asp | Gln | Val | Lys | Ala | Asn | Ala |  |
|  |  |  |  | 185 |  |  |  |  | 190 |  |  |  |  | 195 |  |  |
| agg | tca | ggt | ggc | ttt | gta | atc | tct | tta | gat | gta | tca | gtc | aca | gag | gag | 919 |
| Arg | Ser | Gly | Gly | Phe | Val | Ile | Ser | Leu | Asp | Val | Ser | Val | Thr | Glu | Glu |  |
|  |  |  | 200 |  |  |  |  | 205 |  |  |  |  | 210 |  |  |  |
| att | gat | ctc | gaa | aaa | tca | gca | tca | agt | cat | gat | aga | gta | aat | gat | tat | 967 |
| Ile | Asp | Leu | Glu | Lys | Ser | Ala | Ser | Ser | His | Asp | Arg | Val | Asn | Asp | Tyr |  |
|  |  | 215 |  |  |  |  | 220 |  |  |  |  | 225 |  |  |  |  |
| aat | gct | tcc | ttg | aga | caa | gag | tct | aga | aat | cgg | tta | tac | cga | gat | ggt | 1015 |
| Asn | Ala | Ser | Leu | Arg | Gln | Glu | Ser | Arg | Asn | Arg | Leu | Tyr | Arg | Asp | Gly |  |
|  | 230 |  |  |  |  | 235 |  |  |  |  | 240 |  |  |  |  |  |
| ggc | aaa | act | cgt | ctg | aag | gac | act | gat | aat | gga | gct | gaa | tct | cac | ttg | 1063 |
| Gly | Lys | Thr | Arg | Leu | Lys | Asp | Thr | Asp | Asn | Gly | Ala | Glu | Ser | His | Leu |  |
| 245 |  |  |  |  | 250 |  |  |  |  | 255 |  |  |  |  | 260 |  |
| gca | acg | gaa | aat | cat | tca | caa | gag | ggt | cat | ggc | agt | cct | gaa | gac | att | 1111 |
| Ala | Thr | Glu | Asn | His | Ser | Gln | Glu | Gly | His | Gly | Ser | Pro | Glu | Asp | Ile |  |
|  |  |  |  | 265 |  |  |  |  | 270 |  |  |  |  | 275 |  |  |
| gat | aat | gat | cgt | gaa | tac | agc | aaa | agc | aga | gca | tgc | gcc | tct | ctg | cag | 1159 |
| Asp | Asn | Asp | Arg | Glu | Tyr | Ser | Lys | Ser | Arg | Ala | Cys | Ala | Ser | Leu | Gln |  |
|  |  |  | 280 |  |  |  |  | 285 |  |  |  |  | 290 |  |  |  |
| cag | ata | aat | gaa | gag | gca | agt | gat | gac | gtt | tct | gat | gat | tcg | atg | gtg | 1207 |
| Gln | Ile | Asn | Glu | Glu | Ala | Ser | Asp | Asp | Val | Ser | Asp | Asp | Ser | Met | Val |  |
|  |  | 295 |  |  |  |  | 300 |  |  |  |  | 305 |  |  |  |  |
| gat | tct | ata | tcc | agc | ata | gat | gtc | tct | ccc | gat | gat | gtt | gtg | ggt | ata | 1255 |
| Asp | Ser | Ile | Ser | Ser | Ile | Asp | Val | Ser | Pro | Asp | Asp | Val | Val | Gly | Ile |  |
|  | 310 |  |  |  |  | 315 |  |  |  |  | 320 |  |  |  |  |  |
| tta | ggt | caa | aaa | cgt | ttc | tgg | aga | gca | agg | aaa | gcc | att | gcc | aat | caa | 1303 |
| Leu | Gly | Gln | Lys | Arg | Phe | Trp | Arg | Ala | Arg | Lys | Ala | Ile | Ala | Asn | Gln |  |
| 325 |  |  |  |  | 330 |  |  |  |  | 335 |  |  |  |  | 340 |  |
| caa | aga | gta | ttt | gct | gtt | caa | cta | ttt | gag | ttg | cac | aga | ctg | att | aag | 1351 |

```
                Gln Arg Val Phe Ala Val Gln Leu Phe Glu Leu His Arg Leu Ile Lys
                                345                 350                 355 gtt caa aaa ctt att gct gca tca ccg gat ctc ttg ctc gat gag atc              1399
Val Gln Lys Leu Ile Ala Ala Ser Pro Asp Leu Leu Leu Asp Glu Ile
            360                 365                 370 agt ttt ctt gga aaa gtt tct gct aaa agc tat cca gtg aag aag ctc              1447
Ser Phe Leu Gly Lys Val Ser Ala Lys Ser Tyr Pro Val Lys Lys Leu
        375                 380                 385 ctt cca tca gaa ttt ctg gta aag cct cct cta cca cat gtt gtc gtc              1495
Leu Pro Ser Glu Phe Leu Val Lys Pro Pro Leu Pro His Val Val Val
    390                 395                 400 aaa caa agg ggt gac tcg gag aag act gac caa cat aaa atg gaa agc              1543
Lys Gln Arg Gly Asp Ser Glu Lys Thr Asp Gln His Lys Met Glu Ser
405                 410                 415                 420 tca gct gag aac gta gtt ggg agg ttg tca aat caa ggt cat cat caa              1591
Ser Ala Glu Asn Val Val Gly Arg Leu Ser Asn Gln Gly His His Gln
                425                 430                 435 caa tcc aac tac atg cct ttt gca aac aac cca ccg gct tca ccg gct              1639
Gln Ser Asn Tyr Met Pro Phe Ala Asn Asn Pro Pro Ala Ser Pro Ala
            440                 445                 450 cca aat gga tat tgc ttt cct cct cag cct cct cct tca gga aat cat              1687
Pro Asn Gly Tyr Cys Phe Pro Pro Gln Pro Pro Pro Ser Gly Asn His
        455                 460                 465 cag caa tgg ttg atc cct gta atg tct ccc tcg gaa gga ctg ata tac              1735
Gln Gln Trp Leu Ile Pro Val Met Ser Pro Ser Glu Gly Leu Ile Tyr
    470                 475                 480 aag cct cac cca ggt atg gca cac acg ggg cat tat gga gga tat tat              1783
Lys Pro His Pro Gly Met Ala His Thr Gly His Tyr Gly Gly Tyr Tyr
485                 490                 495                 500 ggt cat tat atg cct aca cca atg gta atg cct caa tat cac ccc ggc              1831
Gly His Tyr Met Pro Thr Pro Met Val Met Pro Gln Tyr His Pro Gly
                505                 510                 515 atg gga ttc cca cct cct ggt aat ggc tac ttc cct cca tat gga atg              1879
Met Gly Phe Pro Pro Pro Gly Asn Gly Tyr Phe Pro Pro Tyr Gly Met
            520                 525                 530 atg ccc acc ata atg aac cca tat tgt tca agc caa caa caa caa caa              1927
Met Pro Thr Ile Met Asn Pro Tyr Cys Ser Ser Gln Gln Gln Gln Gln
        535                 540                 545 caa caa ccc aat gag caa atg aac cag ttt gga cat cct gga aat ctt              1975
Gln Gln Pro Asn Glu Gln Met Asn Gln Phe Gly His Pro Gly Asn Leu
    550                 555                 560 cag aac acc caa caa caa caa cag aga tct gat aat gaa cct gct cca              2023
Gln Asn Thr Gln Gln Gln Gln Gln Arg Ser Asp Asn Glu Pro Ala Pro
565                 570                 575                 580 cag caa cag caa cag cca aca aag tct tat ccg cga gca aga aag agc              2071
Gln Gln Gln Gln Gln Pro Thr Lys Ser Tyr Pro Arg Ala Arg Lys Ser
                585                 590                 595 agg caa ggg agc aca gga agc agt cca agt ggg cca cag gga atc tct              2119
Arg Gln Gly Ser Thr Gly Ser Ser Pro Ser Gly Pro Gln Gly Ile Ser
            600                 605                 610 ggt agc aag tcc ttt cgg cca ttc gca gcc gtt gat gag gac agc aac              2167
Gly Ser Lys Ser Phe Arg Pro Phe Ala Ala Val Asp Glu Asp Ser Asn
        615                 620                 625 atc aac aat gca cct gag caa acg atg aca aca acc aca acg aca              2215
Ile Asn Asn Ala Pro Glu Gln Thr Met Thr Thr Thr Thr Thr Thr
    630                 635                 640 aga aca act gtt act cag aca aca aga gat ggg gga gga gtg acg aga              2263
Arg Thr Thr Val Thr Gln Thr Thr Arg Asp Gly Gly Gly Val Thr Arg
645                 650                 655                 660
```

```
gtg ata aag gtg gta cct cac aac gca aag ctc gcg agt gag aat gct    2311
Val Ile Lys Val Val Pro His Asn Ala Lys Leu Ala Ser Glu Asn Ala
            665                 670                 675 gcc aga att ttc cag tca ata caa gaa gaa cgt aaa cgc tat gac tcc    2359
Ala Arg Ile Phe Gln Ser Ile Gln Glu Glu Arg Lys Arg Tyr Asp Ser
            680                 685                 690 tct aag cct taa tcctctctat gcgtattgta cttgatatgt attttacaaa        2411
Ser Lys Pro
        695 attagaaaaa ttgtgataga tgttatcctc aatatatgta ccatgtaaac gtattatggt  2471 gtaagcctca tttatatgtg ttaatttgtc ttaaaaaaaa aaaaaaa                2518

<210> SEQ ID NO 2
<211> LENGTH: 695
<212> TYPE: PRT
<213> ORGANISM: Arabidopsis thaliana

<400> SEQUENCE: 2

Met Lys Arg Gly Lys Asp Glu Glu Lys Ile Leu Glu Pro Met Phe Pro
1               5                   10                  15

Arg Leu His Val Asn Asp Ala Asp Lys Gly Gly Pro Arg Ala Pro Pro
                20                  25                  30

Arg Asn Lys Met Ala Leu Tyr Glu Gln Leu Ser Ile Pro Ser Gln Arg
            35                  40                  45

Phe Gly Asp His Gly Thr Met Asn Ser Arg Ser Asn Asn Thr Ser Thr
        50                  55                  60

Leu Val His Pro Gly Pro Ser Ser Gln Pro Cys Gly Val Glu Arg Asn
65                  70                  75                  80

Leu Ser Val Gln His Leu Asp Ser Ser Ala Ala Asn Gln Ala Thr Glu
                85                  90                  95

Lys Phe Val Ser Gln Met Ser Phe Met Glu Asn Val Arg Ser Ser Ala
            100                 105                 110

Gln His Asp Gln Arg Lys Met Val Arg Glu Glu Asp Phe Ala Val
        115                 120                 125

Pro Val Tyr Ile Asn Ser Arg Arg Ser Gln Ser His Gly Arg Thr Lys
    130                 135                 140

Ser Gly Ile Glu Lys Glu Lys His Thr Pro Met Val Ala Pro Ser Ser
145                 150                 155                 160

His His Ser Ile Arg Phe Gln Glu Val Asn Gln Thr Gly Ser Lys Gln
                165                 170                 175

Asn Val Cys Leu Ala Thr Cys Ser Lys Pro Glu Val Arg Asp Gln Val
            180                 185                 190

Lys Ala Asn Ala Arg Ser Gly Gly Phe Val Ile Ser Leu Asp Val Ser
        195                 200                 205

Val Thr Glu Glu Ile Asp Leu Lys Ser Ala Ser Ser His Asp Arg
    210                 215                 220

Val Asn Asp Tyr Asn Ala Ser Leu Arg Gln Glu Ser Arg Asn Arg Leu
225                 230                 235                 240

Tyr Arg Asp Gly Gly Lys Thr Arg Leu Lys Asp Thr Asp Asn Gly Ala
                245                 250                 255

Glu Ser His Leu Ala Thr Glu Asn His Ser Gln Glu Gly His Gly Ser
            260                 265                 270

Pro Glu Asp Ile Asp Asn Asp Arg Glu Tyr Ser Lys Ser Arg Ala Cys
        275                 280                 285

Ala Ser Leu Gln Gln Ile Asn Glu Glu Ala Ser Asp Asp Val Ser Asp
```

-continued

```
                290                 295                 300
Asp Ser Met Val Asp Ser Ile Ser Ser Ile Asp Val Ser Pro Asp Asp
305                 310                 315                 320

Val Val Gly Ile Leu Gly Gln Lys Arg Phe Trp Arg Ala Arg Lys Ala
                325                 330                 335

Ile Ala Asn Gln Gln Arg Val Phe Ala Val Gln Leu Phe Glu Leu His
                340                 345                 350

Arg Leu Ile Lys Val Gln Lys Leu Ile Ala Ala Ser Pro Asp Leu Leu
                355                 360                 365

Leu Asp Glu Ile Ser Phe Leu Gly Lys Val Ser Ala Lys Ser Tyr Pro
370                 375                 380

Val Lys Lys Leu Leu Pro Ser Glu Phe Leu Val Lys Pro Pro Leu Pro
385                 390                 395                 400

His Val Val Lys Gln Arg Gly Asp Ser Glu Lys Thr Asp Gln His
                405                 410                 415

Lys Met Glu Ser Ser Ala Glu Asn Val Val Gly Arg Leu Ser Asn Gln
                420                 425                 430

Gly His His Gln Gln Ser Asn Tyr Met Pro Phe Ala Asn Asn Pro Pro
                435                 440                 445

Ala Ser Pro Ala Pro Asn Gly Tyr Cys Phe Pro Pro Gln Pro Pro
450                 455                 460

Ser Gly Asn His Gln Gln Trp Leu Ile Pro Val Met Ser Pro Ser Glu
465                 470                 475                 480

Gly Leu Ile Tyr Lys Pro His Pro Gly Met Ala His Thr Gly His Tyr
                485                 490                 495

Gly Gly Tyr Tyr Gly His Tyr Met Pro Thr Pro Met Val Met Pro Gln
                500                 505                 510

Tyr His Pro Gly Met Gly Phe Pro Pro Gly Asn Gly Tyr Phe Pro
                515                 520                 525

Pro Tyr Gly Met Met Pro Thr Ile Met Asn Pro Tyr Cys Ser Ser Gln
530                 535                 540

Gln Gln Gln Gln Gln Pro Asn Glu Gln Met Asn Gln Phe Gly His
545                 550                 555                 560

Pro Gly Asn Leu Gln Asn Thr Gln Gln Gln Gln Arg Ser Asp Asn
                565                 570                 575

Glu Pro Ala Pro Gln Gln Gln Gln Pro Thr Lys Ser Tyr Pro Arg
                580                 585                 590

Ala Arg Lys Ser Arg Gln Gly Ser Thr Gly Ser Ser Pro Ser Gly Pro
                595                 600                 605

Gln Gly Ile Ser Gly Ser Lys Ser Phe Arg Pro Phe Ala Ala Val Asp
                610                 615                 620

Glu Asp Ser Asn Ile Asn Asn Ala Pro Glu Gln Thr Met Thr Thr Thr
625                 630                 635                 640

Thr Thr Thr Thr Arg Thr Thr Val Thr Gln Thr Thr Arg Asp Gly Gly
                645                 650                 655

Gly Val Thr Arg Val Ile Lys Val Val Pro His Asn Ala Lys Leu Ala
                660                 665                 670

Ser Glu Asn Ala Ala Arg Ile Phe Gln Ser Ile Gln Glu Glu Arg Lys
                675                 680                 685

Arg Tyr Asp Ser Ser Lys Pro
690                 695
```

<210> SEQ ID NO 3

-continued

```
<211> LENGTH: 4221
<212> TYPE: DNA
<213> ORGANISM: Arabidopsis thaliana
<220> FEATURE:
<221> NAME/KEY: promoter
<222> LOCATION: (1)..(142)
<223> OTHER INFORMATION:
<221> NAME/KEY: 5'UTR
<222> LOCATION: (143)..(425)
<223> OTHER INFORMATION:
<221> NAME/KEY: exon
<222> LOCATION: (426)..(644)
<223> OTHER INFORMATION:
<221> NAME/KEY: exon
<222> LOCATION: (1007)..(1803)
<223> OTHER INFORMATION:
<221> NAME/KEY: exon
<222> LOCATION: (2984)..(3037)
<223> OTHER INFORMATION:
<221> NAME/KEY: exon
<222> LOCATION: (3128)..(4142)
<223> OTHER INFORMATION:
<221> NAME/KEY: Intron
<222> LOCATION: (645)..(1006)
<223> OTHER INFORMATION:
<221> NAME/KEY: Intron
<222> LOCATION: (1804)..(2983)
<223> OTHER INFORMATION:
<221> NAME/KEY: Intron
<222> LOCATION: (3038)..(3127)
<223> OTHER INFORMATION:
<221> NAME/KEY: 3'UTR
<222> LOCATION: (4146)..(4221)
<223> OTHER INFORMATION:

<400> SEQUENCE: 3
tatctttggg ggctccactt ttcctatctc tttttgcccc tttcctctct ctgttcacaa      60
gtcatcttct tccttcctct gaatcttgtt ccttttgct ctctctactt gattcaccca     120
ctctgtttct cgattagtac gttgaaaact cactttggtt ttgtttgatt cctctttagt    180
ctgtttttcg atttcgtttt tctgattgg tttggtggtg agatctctat cgtagtttgt     240
cctttgggtt aagatatttc atttgattgg tgggtttgtt ttattgaagc ttattgttgt    300
gaaagttgga gtctttctca gttttaggt tgaattatta agagaaaggg aagattttg      360 gtgtgaagtt aggttatttg gggtttgaga agtttgcaag tgaaaaaggt tgtgaattgt    420 gagtg atg aag aga ggg aaa gat gag gag aag ata ttg gaa cct atg ttt    470
      Met Lys Arg Gly Lys Asp Glu Glu Lys Ile Leu Glu Pro Met Phe
      1               5                  10                  15 cct cgg ctt cat gtg aat gat gca gat aaa gga ggg cct aga gct cct     518
Pro Arg Leu His Val Asn Asp Ala Asp Lys Gly Gly Pro Arg Ala Pro
         20                  25                  30 cct aga aac aag atg gct ctt tat gag cag ctt agt att cct tct cag    566
Pro Arg Asn Lys Met Ala Leu Tyr Glu Gln Leu Ser Ile Pro Ser Gln
     35                  40                  45 agg ttt ggt gat cat gga acg atg aat tct cgt agt aac aac aca agc    614
Arg Phe Gly Asp His Gly Thr Met Asn Ser Arg Ser Asn Asn Thr Ser
 50                  55                  60 act ttg gtt cat cct gga cca tct agt cag gtattgtttt gattttgatc       664
Thr Leu Val His Pro Gly Pro Ser Ser Gln
 65                  70 attgtatagg ctcttgatgt tattagttgt atgagtttgg atgttatata gcctgaaaga    724
gaaagtagga cattggttga tctatgtttc aattgttatc agatcatagt atcttctttt    784
tgcttatgga ttgagctttt aggattgaat tctcctgtat atatgagagt cttgtagaca    844
caagtttatc taagtgtggt ttatttctta aaactaacat tcttgttgtg cctgattctt    904
```

```
                                                                              -continued
tttatgttct gaagttcgat gaaagtttct tgtgattgcc ctgagcattc agactattgc                964
aaggacatga gaaataatcc tttttttaccc tcttcaatgc ag cct tgt ggt gtg               1018
                                                  Pro Cys Gly Val
                                                  75 gaa aga aac tta tct gtc cag cat ctt gat tct tca gcc gca aac caa               1066
Glu Arg Asn Leu Ser Val Gln His Leu Asp Ser Ser Ala Ala Asn Gln
        80              85                  90 gca act gag aag ttt gtc tcc caa atg tcc ttc atg gaa aat gtg aga               1114
Ala Thr Glu Lys Phe Val Ser Gln Met Ser Phe Met Glu Asn Val Arg
 95                 100                 105 tct tcg gca cag cat gat cag agg aaa atg gtg aga gag gaa gaa gat               1162
Ser Ser Ala Gln His Asp Gln Arg Lys Met Val Arg Glu Glu Glu Asp
110             115                 120                 125 ttt gca gtt cca gta tat att aac tca aga aga tct cag tct cat ggc               1210
Phe Ala Val Pro Val Tyr Ile Asn Ser Arg Arg Ser Gln Ser His Gly
                130                 135                 140 aga acc aag agt ggt att gag aag gaa aaa cac acc cca atg gtg gca               1258
Arg Thr Lys Ser Gly Ile Glu Lys Glu Lys His Thr Pro Met Val Ala
            145                 150                 155 cct agc tct cat cac tcc att cga ttt caa gaa gtg aat cag aca ggc               1306
Pro Ser Ser His His Ser Ile Arg Phe Gln Glu Val Asn Gln Thr Gly
            160                 165                 170 tca aag caa aac gta tgt ttg gct act tgt tca aaa cct gaa gtt agg               1354
Ser Lys Gln Asn Val Cys Leu Ala Thr Cys Ser Lys Pro Glu Val Arg
175                 180                 185 gat cag gtc aag gcg aat gca agg tca ggt ggc ttt gta atc tct tta               1402
Asp Gln Val Lys Ala Asn Ala Arg Ser Gly Gly Phe Val Ile Ser Leu
190             195                 200                 205 gat gta tca gtc aca gag gag att gat ctc gaa aaa tca gca tca agt               1450
Asp Val Ser Val Thr Glu Glu Ile Asp Leu Glu Lys Ser Ala Ser Ser
                210                 215                 220 cat gat aga gta aat gat tat aat gct tcc ttg aga caa gag tct aga               1498
His Asp Arg Val Asn Asp Tyr Asn Ala Ser Leu Arg Gln Glu Ser Arg
            225                 230                 235 aat cgg tta tac cga gat ggt ggc aaa act cgt ctg aag gac act gat               1546
Asn Arg Leu Tyr Arg Asp Gly Gly Lys Thr Arg Leu Lys Asp Thr Asp
        240                 245                 250 aat gga gct gaa tct cac ttg gca acg gaa aat cat tca caa gag ggt               1594
Asn Gly Ala Glu Ser His Leu Ala Thr Glu Asn His Ser Gln Glu Gly
    255                 260                 265 cat ggc agt cct gaa gac att gat aat gat cgt gaa tac agc aaa agc               1642
His Gly Ser Pro Glu Asp Ile Asp Asn Asp Arg Glu Tyr Ser Lys Ser
270                 275                 280                 285 aga gca tgc gcc tct ctg cag cag ata aat gaa gag gca agt gat gac               1690
Arg Ala Cys Ala Ser Leu Gln Gln Ile Asn Glu Glu Ala Ser Asp Asp
                290                 295                 300 gtt tct gat gat tcg atg gtg gat tct ata tcc agc ata gat gtc tct               1738
Val Ser Asp Asp Ser Met Val Asp Ser Ile Ser Ser Ile Asp Val Ser
            305                 310                 315 ccc gat gat gtt gtg ggt ata tta ggt caa aaa cgt ttc tgg aga gca               1786
Pro Asp Asp Val Val Gly Ile Leu Gly Gln Lys Arg Phe Trp Arg Ala
        320                 325                 330 agg aaa gcc att gcc aa gtaagttcac tagaaattta cagtttggtt                       1833
Arg Lys Ala Ile Ala Asn
            335 atttattctc cgctctttct atttatctcc ttctttgata ccaacatttt ttgcttgaaa             1893 gaagttaata tttaagcatt gttccgtagt cttactgaag cttttttcctc tgttgttttt            1953 tgctatttc attgaggact gtggtagggc atatttcact atcaccaaat ttcaaatttc              2013
```

```
tagaacactc tccttcatat ttttttttcat gattaatgct gcaattgatt gctgatatac  2073
atatatgact ataactcagt ttcatattct gtctcatttt gggagaaaga gatttcaggt  2133
ttatgcttga gaagtgatgg ttctatagtt gagaggcccc tgattcatct aaaatggtcc  2193
tattatgtgt ttagttgtag agtcctcggt agaatattaa cgcgtttaac acgttggatc  2253
atgttatagc agggagggac attctctgtt gacctatatt gtgcaaggtg cccgccgatg  2313
gctttattac tataccttct ttgcatctgg ttgttggaac atgtccctgt ctcggtttgg  2373
tattgctttt attctgcact gtcgtcttgg gcattttccc tacttgtcat tcaagggggtt 2433
gaaccaggta gggaaatgtt tttccgagga ccccaggatc taaattttag ttaaccatac  2493
gtaaagttag ttttgagtct tatgacgatg cagaattata gtttcttctt actactgctt  2553
aagaggatcc ttagtgtggt tgtgaactac agagttttta tgattgtagg cttcatgact  2613
taactttttaa ggttcaatgt actctaatcc atatggtaag gtatcggatt cacgaccaat  2673
gcaaataata agattttttat ttcttgcttc ttgttaaata tctgacatct cattttgcag  2733
aggataagct gcgctgtaag ctagatttca ataagcccgt cctttgcatt gttatctatg  2793
ctttaatatg tcattggacc cattgatttg gttttcttct atcttttttg attggctatg  2853
tattcttgtt tcttttttcc tatctcattt cgatcgtatt gttccattag ctgttcaacc  2913
taaactatgt ctctctttgt tgaactttg atggataatc ttcttaatgt gactctgttt   2973
ctcattacag t caa caa aga gta ttt gct gtt caa cta ttt gag ttg cac  3023
              Gln Gln Arg Val Phe Ala Val Gln Leu Phe Glu Leu His
              340             345             350
aga ctg att aag gt aaagtcattc agaaacttct catatgtttc catgagtatt   3077
Arg Leu Ile Lys Val
            355
tgtttcttct cgagctgaaa caaacctctt caactgtgta ataatcaggt t caa aaa  3134
                                                        Gln Lys
ctt att gct gca tca ccg gat ctc ttg ctc gat gag atc agt ttt ctt  3182
Leu Ile Ala Ala Ser Pro Asp Leu Leu Leu Asp Glu Ile Ser Phe Leu
360             365             370             375
gga aaa gtt tct gct aaa agc tat cca gtg aag aag ctc ctt cca tca  3230
Gly Lys Val Ser Ala Lys Ser Tyr Pro Val Lys Lys Leu Leu Pro Ser
            380             385             390
gaa ttt ctg gta aag cct cct cta cca cat gtt gtc gtc aaa caa agg  3278
Glu Phe Leu Val Lys Pro Pro Leu Pro His Val Val Val Lys Gln Arg
        395             400             405
ggt gac tcg gag aag act gac caa cat aaa atg gaa agc tca gct gag  3326
Gly Asp Ser Glu Lys Thr Asp Gln His Lys Met Glu Ser Ser Ala Glu
        410             415             420
aac gta gtt ggg agg ttg tca aat caa ggt cat cat caa caa tcc aac  3374
Asn Val Val Gly Arg Leu Ser Asn Gln Gly His His Gln Gln Ser Asn
    425             430             435
tac atg cct ttt gca aac aac cca ccg gct tca ccg gct cca aat gga  3422
Tyr Met Pro Phe Ala Asn Asn Pro Pro Ala Ser Pro Ala Pro Asn Gly
440             445             450             455
tat tgc ttt cct cct cag cct cct cct tca gga aat cat cag caa tgg  3470
Tyr Cys Phe Pro Pro Gln Pro Pro Pro Ser Gly Asn His Gln Gln Trp
            460             465             470
ttg atc cct gta atg tct ccc tcg gaa gga ctg ata tac aag cct cac  3518
Leu Ile Pro Val Met Ser Pro Ser Glu Gly Leu Ile Tyr Lys Pro His
        475             480             485
cca ggt atg gca cac acg ggg cat tat gga gga tat tat ggt cat tat  3566
Pro Gly Met Ala His Thr Gly His Tyr Gly Gly Tyr Tyr Gly His Tyr
        490             495             500
```

```
atg cct aca cca atg gta atg cct caa tat cac ccc ggc atg gga ttc    3614
Met Pro Thr Pro Met Val Met Pro Gln Tyr His Pro Gly Met Gly Phe
    505                 510                 515 cca cct cct ggt aat ggc tac ttc cct cca tat gga atg atg ccc acc    3662
Pro Pro Pro Gly Asn Gly Tyr Phe Pro Pro Tyr Gly Met Met Pro Thr
520                 525                 530                 535 ata atg aac cca tat tgt tca agc caa caa caa caa caa caa ccc        3710
Ile Met Asn Pro Tyr Cys Ser Ser Gln Gln Gln Gln Gln Gln Pro
                540                 545                 550 aat gag caa atg aac cag ttt gga cat cct gga aat ctt cag aac acc    3758
Asn Glu Gln Met Asn Gln Phe Gly His Pro Gly Asn Leu Gln Asn Thr
    555                 560                 565 caa caa caa caa cag aga tct gat aat gaa cct gct cca cag caa cag    3806
Gln Gln Gln Gln Gln Arg Ser Asp Asn Glu Pro Ala Pro Gln Gln Gln
570                 575                 580 caa cag cca aca aag tct tat ccg cga gca aga aag agc agg caa ggg    3854
Gln Gln Pro Thr Lys Ser Tyr Pro Arg Ala Arg Lys Ser Arg Gln Gly
585                 590                 595 agc aca gga agc agt cca agt ggg cca cag gga atc tct ggt agc aag    3902
Ser Thr Gly Ser Ser Pro Ser Gly Pro Gln Gly Ile Ser Gly Ser Lys
600                 605                 610                 615 tcc ttt cgg cca ttc gca gcc gtt gat gag gac agc aac atc aac aat    3950
Ser Phe Arg Pro Phe Ala Ala Val Asp Glu Asp Ser Asn Ile Asn Asn
                620                 625                 630 gca cct gag caa acg atg aca aca acc aca acg aca aga aca act        3998
Ala Pro Glu Gln Thr Met Thr Thr Thr Thr Thr Thr Arg Thr Thr
    635                 640                 645 gtt act cag aca aca aga gat ggg gga gga gtg acg aga gtg ata aag    4046
Val Thr Gln Thr Thr Arg Asp Gly Gly Gly Val Thr Arg Val Ile Lys
650                 655                 660 gtg gta cct cac aac gca aag ctc gcg agt gag aat gct gcc aga att    4094
Val Val Pro His Asn Ala Lys Leu Ala Ser Glu Asn Ala Ala Arg Ile
665                 670                 675 ttc cag tca ata caa gaa gaa cgt aaa cgc tat gac tcc tct aag cct    4142
Phe Gln Ser Ile Gln Glu Glu Arg Lys Arg Tyr Asp Ser Ser Lys Pro
680                 685                 690                 695 taatcctctc tatgcgtatt gtacttgata tgtattttac aaaattagaa aaattgtgat  4202
agatgttatc ctcaatata                                               4221

<210> SEQ ID NO 4
<211> LENGTH: 2088
<212> TYPE: DNA
<213> ORGANISM: Arabidopsis thaliana

<400> SEQUENCE: 4
atgaagagag ggaaagatga ggagaagata ttggaaccta tgtttcctcg gcttcatgtg    60
aatgatgcag ataaaggagg gcctagagct cctcctagaa caagatggc tctttatgag    120 cagcttagta ttccttctca gaggtttggt gatcatggaa cgatgaattc tcgtagtaac   180
aacacaagca ctttggttca tcctggacca tctagtcagc cttgtggtgt ggaaagaaac   240
ttatctgtcc agcatcttga ttcttcagcc gcaaaccaag caactgagaa gtttgtctcc   300
caaatgtcct tcatggaaaa tgtgagatct tcggcacagc atgatcagag gaaaatggtg   360
agagaggaag aagattttgc agttccagta tatattaact caagaagatc tcagtctcat   420
ggcagaacca agagtggtat tgagaaggaa aaacacaccc caatggtggc acctagctct   480
catcactcca ttcgatttca agaagtgaat cagacaggct caaagcaaaa cgtatgtttg   540
```

-continued

```
gctacttgtt caaaacctga agttagggat caggtcaagg cgaatgcaag gtcaggtggc      600
tttgtaatct ctttagatgt atcagtcaca gaggagattg atctcgaaaa atcagcatca      660
agtcatgata gagtaaatga ttataatgct tccttgagac aagagtctag aaatcggtta      720
taccgagatg gtggcaaaac tcgtctgaag gacactgata atggagctga atctcacttg      780
gcaacggaaa atcattcaca agagggtcat ggcagtcctg aagacattga taatgatcgt      840
gaatacagca aaagcagagc atgcgcctct ctgcagcaga taaatgaaga ggcaagtgat      900
gacgtttctg atgattcgat ggtggattct atatccagca tagatgtctc tcccgatgat      960
gttgtgggta tattaggtca aaaacgtttc tggagagcaa ggaaagccat tgccaatcaa     1020
caaagagtat ttgctgttca actatttgag ttgcacagac tgattaaggt tcaaaaactt     1080
attgctgcat caccggatct cttgctcgat gagatcagtt ttcttggaaa agtttctgct     1140
aaaagctatc cagtgaagaa gctccttcca tcagaatttc tggtaaagcc tcctctacca     1200
catgttgtcg tcaaacaaag gggtgactcg agaagactg accaacataa aatggaaagc     1260
tcagctgaga acgtagttgg gaggttgtca aatcaaggtc atcatcaaca atccaactac     1320
atgccttttg caaacaaccc accggcttca ccggctccaa atggatattg ctttcctcct     1380
cagcctcctc cttcaggaaa tcatcagcaa tggttgatcc ctgtaatgtc tccctcggaa     1440
ggactgatat acaagcctca cccaggtatg gcacacacgg ggcattatgg aggatattat     1500
ggtcattata tgcctacacc aatggtaatg cctcaatatc accccggcat gggattccca     1560
cctcctggta atggctactt ccctccatat ggaatgatgc ccaccataat gaacccatat     1620
tgttcaagcc aacaacaaca acaacaacaa cccaatgagc aaatgaacca gtttggacat     1680
cctggaaatc ttcagaacac ccaacaacaa caacagagat ctgataatga acctgctcca     1740
cagcaacagc aacagccaac aaagtcttat ccgcgagcaa gaaagagcag gcaagggagc     1800
acaggaagca gtccaagtgg gccacaggga atctctggta gcaagtcctt tcggccattc     1860
gcagccgttg atgaggacag caacatcaac aatgcacctg agcaaacgat gacaacaacc     1920
acaacgacga caagaacaac tgttactcag acaacaagag atggggagg agtgacgaga     1980 gtgataaagg tggtacctca caacgcaaag ctcgcgagtg agaatgctgc cagaattttc     2040
cagtcaatac aagaagaacg taaacgctat gactcctcta agccttaa                 2088
```

<210> SEQ ID NO 5
<211> LENGTH: 4071
<212> TYPE: DNA
<213> ORGANISM: Arabidopsis thaliana

<400> SEQUENCE: 5

```
tgtgttagtg actttcctcc tgaagaattc aactcaagac atgagacaat agattcatga       60
caatatctac tacagtactt gcataacaca atgtaaact aactaacaat tgatagttta      120
gtacacaatc caaattgcaa agagagata ctgcaaatga tctaatcaaa actcatgcat      180
tctacagttc cataagacat ttcaaatcac taatctgaag aaatatgatg cattaataac      240
aaatatttga taactaaaca gacatttgga tcagaaatga agttaaatta agcatttaat      300
tgcttaataa tttaattgat tgattcaaag gcgtaataac acaaaattct tcggggggaat      360 ttgaagggat agagcaaatc gcttagggta aaatgaaaac agcgataagt aacgaattat      420
caaagtctga gttaagaatc aggaaattga gggattgaag aagaataaag ggacctggtt      480
caggaggaat tgagacgtga gtacgctgtg ttggagagga cgacgtcatt ttcgatcaaa      540
gcagcagatt cagcaacgga tggatgggtc tttactcttt gggctgaaga taaccgcaac      600
```

```
tagattcttc ctgagttttt ttttcttttt tgataaaacg agagcccta caggtaaaaa    660 cccaataaaa accacgatcc attttattt ggacatttaa tatttaatta ttttaaatta    720
gaaaataatt acacgaatta ctaaattgta taatatgata ttaaaaaatt aagtgttatt    780
gatgtgtttt cggtctgact gtctataaaa aaatcccca aacataagag ttgttgttgg    840
agtcattaaa ggatcaatg gtttgtggtg gtgtgaccat tggaggaggg tttgttgatg    900
ggtcgtgtgt ttcaccatta atattatcaa atggttctcg gttgattggt cattttgga    960 gtcatcaaat ggctcatatg ttacgctatg tatcacgaaa atatatattt ttctcttaaa   1020
accattcttc cttttccaat aatatggatt tataaattcc cgtgaagata aatatgtggt   1080
ttttactttt cgttttttc ctaggtgagg agggtgttat tggttgctaa tttaaaagga   1140
attttgatga ttttaataat atcataaaaa gtaaattaag attttaaact attgctaggg   1200 agtttttta tgatcttgtt aattagtttt tcacagtctt gtaaagtttt tcaaacaatc   1260
tctctatttt gatgatattt ttttacttta ttttgtgaac aaaagtgtag aaaattatta   1320
aacaataaca caatattta attcattaac aatcatagtt ttttttaaaa aaaaattgaa   1380
taacgccaaa cttttagtga ctttataatt ttttaatta taaggtaagt ctcctaagat   1440
atatgttttg ggttaaagta ttcacaatgt ccaccatgtt atgtgatata ttacccatgt   1500
atattcattt tgtcatttaa tcttaccttt ttgcatttt gtttggctta aaatctacaa   1560
tatcgtttta ctattaaaaa aacctgtaat attcatttac aaatcaatat tttattcttt   1620
ttagacatat cctattttaa tttctacatt cttttcaaaa tagttactaa aataatttt   1680 ttctaaaagc catgaatata aacacaacaa ctaatcaatc tccacaatat atattatata   1740
ttaacaaaaa gtgtattggt gataaaaagt acttgatgat acactaaaca aaaggataa   1800 atgggagaat ttttattt gaagatgaa acattttagg ttatatattt catgaccctt   1860
ataaataaaa ttcctggctc caccactgga tatctctaca tatttccaac atcaatatcc   1920
attgatattt gataatcttt accaaaaatt cgcaatctcc tttagagtga aagcgagtat   1980
aaccgtatga ccaaactatt ttgagtacca ttggtaattc cttaccttaa gcttccagag   2040
gtattagtgc tatatattca tagtgccacc gagtatttg aactccgaaa tgatttctca   2100
ctatccgacc actcccaatt atataacatg cttagaatta ttcgtaagat ggatcgtagt   2160
tgcattttac gacaccatac aggacaagtc catgatagtt tgagttggtg gattttggaa   2220
cccctgcaaa tttattttat acataacaaa ggccccaatc cattccttag catcacaact   2280
tgggacttct atcttttgaa ggatacattc acttgttggt tttggtaaat atgattgttt   2340
ctttacttcc gaataagcaa tatataaaag tatctaaaaa cggaagtaac ttttgatgat   2400
cctaaaggtt ttgtaattga tacatgtcca aaaacctctt aatattcttt ctcacaaact   2460
gttgatggag ttaacaaagg gagacaaggt aattgggaca atatcaacgt tagatacagg   2520
acaagtgaaa aatgtgggt tgatgtcttc agctgcagca tatcaccgtt ggtatatatt   2580
gtcaattatt agtcctatgg atttgaaacg tgttttagta aataagagtg tccaagtggg   2640
acatttccaa taacgtatca cagctcctag agcttttgct atgtttctct aggcctgggc   2700
cgcctagccc acattccaag caaggaaatg aatggagttg ggcatcaaaa ttttggaagc   2760
atttttaaga caaattatct tttaagtttc cttttttaaa cataaactat attttaggct   2820
tttttaagat aaatattatt tggattttct ttcactcata tttttggatt tcaacttaac   2880
aaaacatagg gcgtgtctat ttgactccac ctacccaccc tactggagtt cgatcccact   2940
```

-continued

```
aaatcgcgtt atcccgcata gtagggattg actatggatc ggactttgtc gatccaaaga    3000
tatctaagaa attcagaaaa gattgtataa aattcagaaa cgattttacg aaattcatga    3060
aaaatgagaa atacatgttt tttttaattt acgtcggcat taaaaacgtt ggaccggctc    3120
tgtgtttcac caaagaaatt gtttcagttt atgcatgatc ttcaacttcc atattcttgt    3180
tttcaattct ggaaatccct aacagatcgg agctctcctc attcagtgag ttggaagatt    3240
gcatgattat ataattactc ttcacatcca catatattac attatattcc cctataattt    3300
catacaaccc tagaaaagaa tcttcaagta atctaatcgt gtcgatgact ccactcattt    3360
gctagaaaag aaaaaacaaa cagacttcat ttagctgaaa acaatctttt attcaacatt    3420
acaaagcact gatcaaagaa cctctaacat ggtaatatat ctatgacatt ttacgtatcc    3480
taaaagaaaa caaaaagtga tgtattggat gatgtttttt tttttacttt tctagtttct    3540
tattacaacg acaaaaagag tccacgtcgt cacgcacttt tccggtggtg aaaaaaatgt    3600
ccaaatggat taaatctata atatctccag agagatcctc tccttctatc tttgggggct    3660 ccactttttcc tatctctttt tgccccttttc ctctctctgt tcacaagtca tcttcttcct    3720
tcctctgaat cttgttcctt tttgctctct ctacttgatt cacccactct gtttctcgat    3780
tagtacgttg aaaactcact ttggttttgt ttgattcctc tttagtctgt ttttcgattt    3840
cgttttctct gattggtttg gtggtgagat ctctatcgta gtttgtcctt tgggttaaga    3900
tatttcattt gattggtggg tttgttttat tgaagcttat tgttgtgaaa gttggagtct    3960
ttctcagttt ttaggttgaa ttattaagag aaagggaaga ttttttggtgt gaagttaggt    4020 tatttggggt ttgagaagtt tgcaagtgaa aaaggttgtg aattgtgagt g             4071
```

<210> SEQ ID NO 6
<211> LENGTH: 24
<212> TYPE: DNA
<213> ORGANISM: ARTIFICIAL SEQUENCE
<220> FEATURE:
<223> OTHER INFORMATION: synthetic oligonucleotide corresponding to a
      portion of the Arabidoposis ELF3 sequence

<400> SEQUENCE: 6
tgaaaactca ctttggtttt gttt                                             24

<210> SEQ ID NO 7
<211> LENGTH: 25
<212> TYPE: DNA
<213> ORGANISM: ARTIFICIAL SEQUENCE
<220> FEATURE:
<223> OTHER INFORMATION: synthetic oligonucleotide corresponding to a
      portion of the Arabidoposis ELF3 sequence

<400> SEQUENCE: 7
aagacaaatt aacacatata aatga                                            25

<210> SEQ ID NO 8
<211> LENGTH: 24
<212> TYPE: DNA
<213> ORGANISM: ARTIFICIAL SEQUENCE
<220> FEATURE:
<223> OTHER INFORMATION: synthetic oligonucleotide corresponding to a
      portion of the Arabidoposis ELF3 sequence

<400> SEQUENCE: 8
atgaatagag ggaaagatga ggag                                             24

<210> SEQ ID NO 9

```
<211> LENGTH: 25
<212> TYPE: DNA
<213> ORGANISM: ARTIFICIAL SEQUENCE
<220> FEATURE:
<223> OTHER INFORMATION: synthetic oligonucleotide corresponding to a
      portion of the Arabidoposis ELF3 sequence

<400> SEQUENCE: 9
ttaaggctta gaggagtcat agcgt                                             25

<210> SEQ ID NO 10
<211> LENGTH: 22
<212> TYPE: DNA
<213> ORGANISM: ARTIFICIAL SEQUENCE
<220> FEATURE:
<223> OTHER INFORMATION: synthetic oligonucleotide corresponding to a
      portion of the Arabidoposis ELF3 sequence

<400> SEQUENCE: 10
agtaagagag ggaaagatga gg                                                22

<210> SEQ ID NO 11
<211> LENGTH: 20
<212> TYPE: DNA
<213> ORGANISM: ARTIFICIAL SEQUENCE
<220> FEATURE:
<223> OTHER INFORMATION: synthetic oligonucleotide corresponding to a
      portion of the Arabidoposis ELF3 sequence

<400> SEQUENCE: 11
gccaccatct cggtataacc                                                   20

<210> SEQ ID NO 12
<211> LENGTH: 1960
<212> TYPE: DNA
<213> ORGANISM: Cardamine oligosperma
<220> FEATURE:
<221> NAME/KEY: CDS
<222> LOCATION: (1)..(1959)
<223> OTHER INFORMATION:

<400> SEQUENCE: 12 atg aag aga ggg aaa gat gat gag aag ata ctg gaa cct atg ttt cct         48
Met Lys Arg Gly Lys Asp Asp Glu Lys Ile Leu Glu Pro Met Phe Pro
1               5                   10                  15 aga ctt cat gtg aat gat gca gat aaa gga gga cct aga gct cct cct         96
Arg Leu His Val Asn Asp Ala Asp Lys Gly Gly Pro Arg Ala Pro Pro
            20                  25                  30 aga aac aag atg gct ctt tat gag cag ctt agt atc cct tct cag agg        144
Arg Asn Lys Met Ala Leu Tyr Glu Gln Leu Ser Ile Pro Ser Gln Arg
        35                  40                  45 ttt ggt gat cat gga aat ttg tct ctg agt tct cgt agt aac aac aca        192
Phe Gly Asp His Gly Asn Leu Ser Leu Ser Ser Arg Ser Asn Asn Thr
    50                  55                  60 agt act ttg gtt cac cct gga cca tct aat cag cag tct tgt ggt gtg        240
Ser Thr Leu Val His Pro Gly Pro Ser Asn Gln Gln Ser Cys Gly Val
65                  70                  75                  80 gaa cga aac tta tct gtc cag cat ctt gat tct tca gct gca gtc cat        288
Glu Arg Asn Leu Ser Val Gln His Leu Asp Ser Ser Ala Ala Val His
                85                  90                  95 gta act gag aat ttt gtc tcc caa atg ccc ttc atg gaa aat atg aga        336
Val Thr Glu Asn Phe Val Ser Gln Met Pro Phe Met Glu Asn Met Arg
            100                 105                 110 tct ttg gca aag cat gat cag agg aaa aca gta aga gag gaa gat gac        384
Ser Leu Ala Lys His Asp Gln Arg Lys Thr Val Arg Glu Glu Asp Asp
```

-continued

|  |  |  |  |  |  |  |  |  |  |  |  |  |  |  |  |
|---|---|---|---|---|---|---|---|---|---|---|---|---|---|---|---|
|  |  | 115 |  |  |  | 120 |  |  |  |  | 125 |  |  |  |  |

```
ttt gca gtt cca gtg ttt gtt aac tca aga aga ttc cag agt cat ggt      432
Phe Ala Val Pro Val Phe Val Asn Ser Arg Arg Phe Gln Ser His Gly
    130             135                 140 agt acc aag agt ggg att gtg att gaa aaa cac acg aca ttg gct act      480
Ser Thr Lys Ser Gly Ile Val Ile Glu Lys His Thr Thr Leu Ala Thr
145                 150                 155                 160 tgt tca aaa ctt gtt aga gat aag gtg aag atg aac gca aag tca ggt      528
Cys Ser Lys Leu Val Arg Asp Lys Val Lys Met Asn Ala Lys Ser Gly
                165                 170                 175 ggc ttt ata gat tta tca tca aca gag gaa gtg gat ctc gaa aaa tca      576
Gly Phe Ile Asp Leu Ser Ser Thr Glu Glu Val Asp Leu Glu Lys Ser
            180                 185                 190 gca tca agt tat gac aga gta aat gat tgt aat tct tcc ttg aga caa      624
Ala Ser Ser Tyr Asp Arg Val Asn Asp Cys Asn Ser Ser Leu Arg Gln
        195                 200                 205 gag tct aga aat aag tta tac cga gat ggt ggc gaa gct cat atg aag      672
Glu Ser Arg Asn Lys Leu Tyr Arg Asp Gly Gly Glu Ala His Met Lys
    210                 215                 220 gac act gct aat aga gtt gaa tct cac ttg gta acg gaa agt cat tct      720
Asp Thr Ala Asn Arg Val Glu Ser His Leu Val Thr Glu Ser His Ser
225                 230                 235                 240 gag gag ggt cat ggc agt cct gat gat gat gac aac ggt cat gaa tac      768
Glu Glu Gly His Gly Ser Pro Asp Asp Asp Asp Asn Gly His Glu Tyr
                245                 250                 255 tgc aga agc aga gga ggc gtc tct cta cag cag ata aat gaa gag gca      816
Cys Arg Ser Arg Gly Gly Val Ser Leu Gln Gln Ile Asn Glu Glu Ala
            260                 265                 270 agt gat gac gtt tct gat aat tcg atg gtg gat tct ata tcc agc ata      864
Ser Asp Asp Val Ser Asp Asn Ser Met Val Asp Ser Ile Ser Ser Ile
        275                 280                 285 gat gtt tct cct gat gat gtt gtg gga gca tta ggt caa aaa cgt ttc      912
Asp Val Ser Pro Asp Asp Val Val Gly Ala Leu Gly Gln Lys Arg Phe
    290                 295                 300 tgg agg gca agg aag gct att acc aat caa caa aga gta ttt gct gtt      960
Trp Arg Ala Arg Lys Ala Ile Thr Asn Gln Gln Arg Val Phe Ala Val
305                 310                 315                 320 caa cta ttt gag ttg cac aga ctg att aag gtt caa aga ctt att gct     1008
Gln Leu Phe Glu Leu His Arg Leu Ile Lys Val Gln Arg Leu Ile Ala
                325                 330                 335 gca tca ccg gat atc gtg ctc gac gaa atc aat tac ctt gga aaa gtt     1056
Ala Ser Pro Asp Ile Val Leu Asp Glu Ile Asn Tyr Leu Gly Lys Val
            340                 345                 350 tct gct aaa agc tat cca gtg aag aag ctc gtt cca tca gaa ttt atc     1104
Ser Ala Lys Ser Tyr Pro Val Lys Lys Leu Val Pro Ser Glu Phe Ile
        355                 360                 365 gta aag cct cct cta cca caa gtt gtc gtc aac aaa cag cac agg agc     1152
Val Lys Pro Pro Leu Pro Gln Val Val Val Asn Lys Gln His Arg Ser
    370                 375                 380 gac tcc gaa aag act gac caa cat aaa atg gaa tgc tca gct gag aat     1200
Asp Ser Glu Lys Thr Asp Gln His Lys Met Glu Cys Ser Ala Glu Asn
385                 390                 395                 400 gtt gtt ggt agg ttg tca aac caa gga cat cat cat aat cat caa cct     1248
Val Val Gly Arg Leu Ser Asn Gln Gly His His His Asn His Gln Pro
                405                 410                 415 tcc aac tac atg cct ttt cca agc aac cca ccc gct tca cca gct gta     1296
Ser Asn Tyr Met Pro Phe Pro Ser Asn Pro Pro Ala Ser Pro Ala Val
            420                 425                 430 aac gga tgt tgc tat cct cct cag cct cct cct tca gga aac cag caa     1344
```

```
                                                                            -continued Asn Gly Cys Cys Tyr Pro Pro Gln Pro Pro Ser Gly Asn Gln Gln
        435                 440                 445 tgg tta atc cct gtt atg tct cct tct gaa gga ctt ata tac aag cct         1392
Trp Leu Ile Pro Val Met Ser Pro Ser Glu Gly Leu Ile Tyr Lys Pro
    450                 455                 460 cat cct ggt atg gga cac acg ggg cac tac gga gga tat tat ggt cat         1440
His Pro Gly Met Gly His Thr Gly His Tyr Gly Gly Tyr Tyr Gly His
465                 470                 475                 480 ttt atg cct ccg ccg atg gta atg cct ccg ttt cat ccg ggc atg gga         1488
Phe Met Pro Pro Pro Met Val Met Pro Pro Phe His Pro Gly Met Gly
                485                 490                 495 ttc cca cct cct ggt aat ggc tac ttc cct cct tat ggt gta atc cca         1536
Phe Pro Pro Pro Gly Asn Gly Tyr Phe Pro Pro Tyr Gly Val Ile Pro
            500                 505                 510 gcc atg atg aac cct tat ggt cca ggc caa caa caa caa caa caa cca         1584
Ala Met Met Asn Pro Tyr Gly Pro Gly Gln Gln Gln Gln Gln Gln Pro
        515                 520                 525 caa gcc aat gaa caa acg aat cag ttt ggg tat tct ggg aat ctt cag         1632
Gln Ala Asn Glu Gln Thr Asn Gln Phe Gly Tyr Ser Gly Asn Leu Gln
    530                 535                 540 aac aac acc cat caa gaa agc tcc gtt aat gaa gct gct cct cca cag         1680
Asn Asn Thr His Gln Glu Ser Ser Val Asn Glu Ala Ala Pro Pro Gln
545                 550                 555                 560 gaa cca cta aca aag tct tat ccg cgg gct aga aag agc agg caa gtg         1728
Glu Pro Leu Thr Lys Ser Tyr Pro Arg Ala Arg Lys Ser Arg Gln Val
                565                 570                 575 agc aca gca agc agt gca agt ggg cga gag gga atc tcc ggt agc act         1776
Ser Thr Ala Ser Ser Ala Ser Gly Arg Glu Gly Ile Ser Gly Ser Thr
            580                 585                 590 tcc ttt cgt cca ttc tca gcc gtt gat gag gat aac aac gat aac aac         1824
Ser Phe Arg Pro Phe Ser Ala Val Asp Glu Asp Asn Asn Asp Asn Asn
        595                 600                 605 aac gac gca cct gat caa atg atg aca acc acc acg acc acg aca aga         1872
Asn Asp Ala Pro Asp Gln Met Met Thr Thr Thr Thr Thr Thr Thr Arg
    610                 615                 620 aca act gtt act cag aca aca aga gat gga gga gaa gtg acg aga gtg         1920
Thr Thr Val Thr Gln Thr Thr Arg Asp Gly Gly Glu Val Thr Arg Val
625                 630                 635                 640 ata aag ggg ttc ctc aca atg cga agc tcg cta gtg aga a                   1960
Ile Lys Gly Phe Leu Thr Met Arg Ser Ser Leu Val Arg
                645                 650

<210> SEQ ID NO 13
<211> LENGTH: 653
<212> TYPE: PRT
<213> ORGANISM: Cardamine oligosperma

<400> SEQUENCE: 13

Met Lys Arg Gly Lys Asp Asp Glu Lys Ile Leu Glu Pro Met Phe Pro
1               5                   10                  15

Arg Leu His Val Asn Asp Ala Asp Lys Gly Gly Pro Arg Ala Pro Pro
            20                  25                  30

Arg Asn Lys Met Ala Leu Tyr Glu Gln Leu Ser Ile Pro Ser Gln Arg
        35                  40                  45

Phe Gly Asp His Gly Asn Leu Ser Leu Ser Ser Arg Ser Asn Asn Thr
    50                  55                  60

Ser Thr Leu Val His Pro Gly Pro Ser Asn Gln Gln Ser Cys Gly Val
65                  70                  75                  80

Glu Arg Asn Leu Ser Val Gln His Leu Asp Ser Ser Ala Ala Val His
```

```
                    85                  90                  95
Val Thr Glu Asn Phe Val Ser Gln Met Pro Phe Met Glu Asn Met Arg
                100                 105                 110

Ser Leu Ala Lys His Asp Gln Arg Lys Thr Val Arg Glu Glu Asp Asp
            115                 120                 125

Phe Ala Val Pro Val Phe Val Asn Ser Arg Arg Phe Gln Ser His Gly
130                 135                 140

Ser Thr Lys Ser Gly Ile Val Ile Glu Lys His Thr Thr Leu Ala Thr
145                 150                 155                 160

Cys Ser Lys Leu Val Arg Asp Lys Val Lys Met Asn Ala Lys Ser Gly
                165                 170                 175

Gly Phe Ile Asp Leu Ser Ser Thr Glu Glu Val Asp Leu Glu Lys Ser
                180                 185                 190

Ala Ser Ser Tyr Asp Arg Val Asn Asp Cys Asn Ser Ser Leu Arg Gln
                195                 200                 205

Glu Ser Arg Asn Lys Leu Tyr Arg Asp Gly Gly Glu Ala His Met Lys
            210                 215                 220

Asp Thr Ala Asn Arg Val Glu Ser His Leu Val Thr Glu Ser His Ser
225                 230                 235                 240

Glu Glu Gly His Gly Ser Pro Asp Asp Asp Asn Gly His Glu Tyr
                245                 250                 255

Cys Arg Ser Arg Gly Val Ser Leu Gln Gln Ile Asn Glu Glu Ala
            260                 265                 270

Ser Asp Asp Val Ser Asp Asn Ser Met Val Asp Ser Ile Ser Ser Ile
            275                 280                 285

Asp Val Ser Pro Asp Asp Val Val Gly Ala Leu Gly Gln Lys Arg Phe
            290                 295                 300

Trp Arg Ala Arg Lys Ala Ile Thr Asn Gln Gln Arg Val Phe Ala Val
305                 310                 315                 320

Gln Leu Phe Glu Leu His Arg Leu Ile Lys Val Gln Arg Leu Ile Ala
                325                 330                 335

Ala Ser Pro Asp Ile Val Leu Asp Glu Ile Asn Tyr Leu Gly Lys Val
            340                 345                 350

Ser Ala Lys Ser Tyr Pro Val Lys Lys Leu Val Pro Ser Glu Phe Ile
            355                 360                 365

Val Lys Pro Pro Leu Pro Gln Val Val Asn Lys Gln His Arg Ser
370                 375                 380

Asp Ser Glu Lys Thr Asp Gln His Lys Met Glu Cys Ser Ala Glu Asn
385                 390                 395                 400

Val Val Gly Arg Leu Ser Asn Gln Gly His His Asn His Gln Pro
                405                 410                 415

Ser Asn Tyr Met Pro Phe Pro Ser Asn Pro Ala Ser Pro Ala Val
            420                 425                 430

Asn Gly Cys Cys Tyr Pro Pro Gln Pro Pro Ser Gly Asn Gln Gln
            435                 440                 445

Trp Leu Ile Pro Val Met Ser Pro Ser Glu Gly Leu Ile Tyr Lys Pro
450                 455                 460

His Pro Gly Met Gly His Thr Gly His Tyr Gly Gly Tyr Tyr Gly His
465                 470                 475                 480

Phe Met Pro Pro Pro Met Val Met Pro Pro Phe His Pro Gly Met Gly
                485                 490                 495

Phe Pro Pro Pro Gly Asn Gly Tyr Phe Pro Pro Tyr Gly Val Ile Pro
            500                 505                 510
```

```
Ala Met Met Asn Pro Tyr Gly Pro Gly Gln Gln Gln Gln Gln Pro
        515                 520                 525

Gln Ala Asn Glu Gln Thr Asn Gln Phe Gly Tyr Ser Gly Asn Leu Gln
        530                 535                 540

Asn Asn Thr His Gln Glu Ser Ser Val Asn Glu Ala Ala Pro Pro Gln
545                 550                 555                 560

Glu Pro Leu Thr Lys Ser Tyr Pro Arg Ala Arg Lys Ser Arg Gln Val
                565                 570                 575

Ser Thr Ala Ser Ser Ala Ser Gly Arg Glu Gly Ile Ser Gly Ser Thr
            580                 585                 590

Ser Phe Arg Pro Phe Ser Ala Val Asp Glu Asp Asn Asn Asp Asn Asn
        595                 600                 605

Asn Asp Ala Pro Asp Gln Met Met Thr Thr Thr Thr Thr Thr Thr Arg
610                 615                 620

Thr Thr Val Thr Gln Thr Thr Arg Asp Gly Gly Glu Val Thr Arg Val
625                 630                 635                 640

Ile Lys Gly Phe Leu Thr Met Arg Ser Ser Leu Val Arg
                645                 650
```

```
<210> SEQ ID NO 14
<211> LENGTH: 3617
<212> TYPE: DNA
<213> ORGANISM: Cardamine oligosperma
<220> FEATURE:
<221> NAME/KEY: 5'UTR
<222> LOCATION: (1)..(306)
<223> OTHER INFORMATION:
<221> NAME/KEY: exon
<222> LOCATION: (307)..(531)
<223> OTHER INFORMATION:
<221> NAME/KEY: exon
<222> LOCATION: (819)..(1531)
<223> OTHER INFORMATION:
<221> NAME/KEY: exon
<222> LOCATION: (2510)..(2561)
<223> OTHER INFORMATION:
<221> NAME/KEY: exon
<222> LOCATION: (2646)..(3615)
<223> OTHER INFORMATION: partial
<221> NAME/KEY: Intron
<222> LOCATION: (532)..(818)
<223> OTHER INFORMATION:
<221> NAME/KEY: Intron
<222> LOCATION: (1532)..(2509)
<223> OTHER INFORMATION:
<221> NAME/KEY: Intron
<222> LOCATION: (2562)..(2645)
<223> OTHER INFORMATION:
<221> NAME/KEY: unsure
<222> LOCATION: (1412)..(1412)
<223> OTHER INFORMATION: W = a or t/u
<221> NAME/KEY: Unsure
<222> LOCATION: (1409)..(1412)
<223> OTHER INFORMATION: encoded amino acid is unsure due to
      nucleotide uncertainty
<221> NAME/KEY: unsure
<222> LOCATION: (1406)..(1406)
<223> OTHER INFORMATION: K = g or t/u
<221> NAME/KEY: unsure
<222> LOCATION: (1404)..(1406)
<223> OTHER INFORMATION: encoded amino acid is unsure due to nucleotide
      uncertainty
<221> NAME/KEY: unsure
<222> LOCATION: (1419)..(1419)
<223> OTHER INFORMATION: R = a or c
<221> NAME/KEY: unsure
<222> LOCATION: (1419)..(1421)
<223> OTHER INFORMATION: encoded amino acid is unsure due to nucleotide
      uncertainty
```

<400> SEQUENCE: 14

```
tacttgattt accatctctc ttaatttatc agctcgtgga gctctcatat ccttcgtttg        60
atttcagttc actcggtttt aaaactttgt tttctctgat tggggagatc taccgtagtc       120
ggtggtcaat tagtgggttt tgttttgagt ttcatttgat ttgtgggttt agtttttga        180 agcttattgt tacgaaattt tgggtctttt tcaattttag gtcaaataat tggggaaaag       240
ttgagaaatc gtgtgaaatt aggttatttg ggttgagaaa ttttgaagca agtttgtga        300 gttgtg atg aag aga ggg aaa gat gat gag aag ata ctg gaa cct atg          348
       Met Lys Arg Gly Lys Asp Asp Glu Lys Ile Leu Glu Pro Met
         1               5                  10 ttt cct aga ctt cat gtg aat gat gca gat aaa gga gga cct aga gct         396
Phe Pro Arg Leu His Val Asn Asp Ala Asp Lys Gly Gly Pro Arg Ala
 15                  20                  25                  30 cct cct aga aac aag atg gct ctt tat gag cag ctt agt atc cct tct         444
Pro Pro Arg Asn Lys Met Ala Leu Tyr Glu Gln Leu Ser Ile Pro Ser
                 35                  40                  45 gag agg ttt ggt gat cat gga aat ttg tct ctg agt tct cgt agt aac         492
Glu Arg Phe Gly Asp His Gly Asn Leu Ser Leu Ser Ser Arg Ser Asn
             50                  55                  60 aac aca agt act ttg gtt cac cct gga cca tct aat cag gtatggagtt          541
Asn Thr Ser Thr Leu Val His Pro Gly Pro Ser Asn Gln
         65                  70                  75 gtggaaattg atgttatata gcttgcaaga gagtagtagg agttgattgt tcaatgtttt       601
cagttgtttt ttagctcatt ttagcttctt ttgttcatgg attgaactca cttgtagata       661
tcggaatata gtggatgtat atctattcta gtgtggaaga ttttttatgt ttgaaagttt       721
tatggatgct tcttgtgatt ggcctgaaca ttctggttac tgtattcaac ttgataagga       781
cattggaaat aatcgttttt ggtgctcttt cctgcag cag tct tgt ggt gtg gaa        836
                                          Gln Ser Cys Gly Val Glu
                                                              80 cga aac tta tct gtc cag cat ctt gat tct tca gct gca gtc cat gta        884
Arg Asn Leu Ser Val Gln His Leu Asp Ser Ser Ala Ala Val His Val
                 85                  90                  95 act gag aat ttt gtc tcc caa atg ccc ttc atg gaa aat atg aga tct        932
Thr Glu Asn Phe Val Ser Gln Met Pro Phe Met Glu Asn Met Arg Ser
            100                 105                 110 ttg gca aag cat gat cag agg aaa aca gta aga gag gaa gat gac ttt        980
Leu Ala Lys His Asp Gln Arg Lys Thr Val Arg Glu Glu Asp Asp Phe
        115                 120                 125 gca gtt cca gtg ttt gtt aac tca aga aga ttc cag agt cat ggt agt       1028
Ala Val Pro Val Phe Val Asn Ser Arg Arg Phe Gln Ser His Gly Ser
130                 135                 140                 145 acc aag agt ggg att gtg att gaa aaa cac acg aca ttg gct act tgt       1076
Thr Lys Ser Gly Ile Val Ile Glu Lys His Thr Thr Leu Ala Thr Cys
                150                 155                 160 tca aaa ctt gtt aga gat aag gtg aag atg aac gca aag tca ggt ggc       1124
Ser Lys Leu Val Arg Asp Lys Val Lys Met Asn Ala Lys Ser Gly Gly
            165                 170                 175 ttt ata gat tta tca tca aca gag gaa gtg gat ctc gaa aaa tca gca       1172
Phe Ile Asp Leu Ser Ser Thr Glu Glu Val Asp Leu Glu Lys Ser Ala
        180                 185                 190 tca agt tat gac aga gta aat gat tgt aat tct tcc ttg aga caa gag       1220
Ser Ser Tyr Asp Arg Val Asn Asp Cys Asn Ser Ser Leu Arg Gln Glu
    195                 200                 205 tct aga aat aag tta tac cga gat ggt ggc gaa gct cat atg aag gac       1268
Ser Arg Asn Lys Leu Tyr Arg Asp Gly Gly Glu Ala His Met Lys Asp
```

```
                                                                -continued
210                   215                    220                      225
act gct aat aga gtt gaa tct cac ttg gta acg gaa agt cat tct gag        1316
Thr Ala Asn Arg Val Glu Ser His Leu Val Thr Glu Ser His Ser Glu
                230                    235                    240 gag ggt cat ggc agt cct gat gat gat gac aac ggt cat gaa tac tgc        1364
Glu Gly His Gly Ser Pro Asp Asp Asp Asp Asn Gly His Glu Tyr Cys
                245                    250                    255 aga agc aga gga ggc gtc tct cta cag cag ata aat gaa gak gca agw        1412
Arg Ser Arg Gly Gly Val Ser Leu Gln Gln Ile Asn Glu Xaa Ala Xaa
                260                    265                    270 gat gac rtt tct gat aat tcg atg gtg gat tct ata tcc agc ata gat        1460
Asp Asp Xaa Ser Asp Asn Ser Met Val Asp Ser Ile Ser Ser Ile Asp
            275                    280                    285 gtt tct cct gat gat gtt gtg gga gca tta ggt caa aaa cgt ttc tgg        1508
Val Ser Pro Asp Asp Val Val Gly Ala Leu Gly Gln Lys Arg Phe Trp
290                    295                    300                    305 agg gca agg aag gct att acc aa  gtaagttcac tagttttttt ttacggttta       1561
Arg Ala Arg Lys Ala Ile Thr Asn
                310 gttaactttg ttatttattt tccgctcttt ctatccatct ctttctttga taccgacttt      1621 gctacttgca agaagttaat gctgaagcat agttacctaa ttagactgaa gctttcctct      1681 gctgttttt ggacactttc ttttagtttc tttgctttt catgcatact gatacaatgg        1741 atatataact cggtttatat tgtgtctcaa tttgggagaa acgatttcgg ttttttggct      1801 tgagacatga tggtactata gtggagaagc ccccccttga ttcctcgtaa aatggtcctg      1861 ttatatgtta gttgacgagc cctcggtagc atattaacgc gttggatcat gttatagcag      1921 ggagggacat tctctgttga cgtacattgt acaaggtgcc cgccgagaca gttcatggct      1981 ttatactctt gtcttctttg catctgcttg ttggaacatg tccctgtctc ggtttggtat      2041 tgcttttatt ctgcactttc gtcttgggca ttttcccttc ttgtcattca agggggttgaa     2101 ccaggtaggg gaacttgttt tcgaggaccc tgggatctaa attttagtta accgtacata      2161 gaacctagtt atgagtctta tgacagtgca gaattatagt tgcttttgtc tactgcttaa     2221 taggatcctt agagtggttg tgaactacgg ttttttctat ggattttaga ctctaggtgt    2281 tcttatcgct acgataaggt atcacgatac atgaccaact catataacaa gctttttcta    2341 gcttttcgtt gagggtaagc tagaaatcta ttaacccatc ctttgcttaa cccattcttg    2401 catttaattt cttttttgtgt tattgcttct gtttttcccctt cgtatttctt catttttacta 2461 ttcgattagc tggtcatatt ccttatgaaa ttccgtttct cattacag t caa caa        2516
                                                        Gln Gln
                                                            315 aga gta ttt gct gtt caa cta ttt gag ttg cac aga ctg att aag            2561
Arg Val Phe Ala Val Gln Leu Phe Glu Leu His Arg Leu Ile Lys
                320                    325                    330 gtaaagtaat tcagaaaact ctcctataa atattttgc tgaaacaaac gtcttcatct       2621
gtgctttgtt tctgtaatac tcag gtt caa aga ctt att gct gca tca ccg        2672
                         Val Gln Arg Leu Ile Ala Ala Ser Pro
                                                         335 gat atc gtg ctc gac gaa atc aat tac ctt gga aaa gtt tct gct aaa       2720
Asp Ile Val Leu Asp Glu Ile Asn Tyr Leu Gly Lys Val Ser Ala Lys
340                    345                    350                    355 agc tat cca gtg aag aag ctc gtt cca tca gaa ttt atc gta aag cct       2768
Ser Tyr Pro Val Lys Lys Leu Val Pro Ser Glu Phe Ile Val Lys Pro
                360                    365                    370 cct cta cca caa gtt gtc gtc aac aaa cag cac agg agc gac tcc gaa       2816
```

| | | |
|---|---|---|
| Pro Leu Pro Gln Val Val Asn Lys Gln His Arg Ser Asp Ser Glu<br>375               380              385 | | |
| aag act gac caa cat aaa atg gaa tgc tca gct gag aat gtt gtt ggt<br>Lys Thr Asp Gln His Lys Met Glu Cys Ser Ala Glu Asn Val Val Gly<br>      390                395                400 | 2864 | |
| agg ttg tca aac caa gga cat cat cat aat cat caa cct tcc aac tac<br>Arg Leu Ser Asn Gln Gly His His His Asn His Gln Pro Ser Asn Tyr<br>405                410                415 | 2912 | |
| atg cct ttt cca agc aac cca ccc gct tca cca gct gta aac gga tgt<br>Met Pro Phe Pro Ser Asn Pro Pro Ala Ser Pro Ala Val Asn Gly Cys<br>420                425                430              435 | 2960 | |
| tgc tat cct cct cag cct cct cct tca gga aac cag caa tgg tta atc<br>Cys Tyr Pro Pro Gln Pro Pro Pro Ser Gly Asn Gln Gln Trp Leu Ile<br>              440                445              450 | 3008 | |
| cct gtt atg tct cct tct gaa gga ctt ata tac aag cct cat cct ggt<br>Pro Val Met Ser Pro Ser Glu Gly Leu Ile Tyr Lys Pro His Pro Gly<br>455                460                465 | 3056 | |
| atg gga cac acg ggg cac tac gga gga tat tat ggt cat ttt atg cct<br>Met Gly His Thr Gly His Tyr Gly Gly Tyr Tyr Gly His Phe Met Pro<br>470                475                480 | 3104 | |
| ccg ccg atg gta atg cct ccg ttt cat ccg ggc atg gga ttc cca cct<br>Pro Pro Met Val Met Pro Pro Phe His Pro Gly Met Gly Phe Pro Pro<br>      485                490                495 | 3152 | |
| cct ggt aat ggc tac ttc cct cct tat ggt gta atc cca gcc atg atg<br>Pro Gly Asn Gly Tyr Phe Pro Pro Tyr Gly Val Ile Pro Ala Met Met<br>500                505                510              515 | 3200 | |
| aac cct tat ggt cca ggc caa caa caa caa caa caa cca caa gcc aat<br>Asn Pro Tyr Gly Pro Gly Gln Gln Gln Gln Gln Gln Pro Gln Ala Asn<br>              520                525              530 | 3248 | |
| gaa caa acg aat cag ttt ggg tat tct ggg aat ctt cag aac aac acc<br>Glu Gln Thr Asn Gln Phe Gly Tyr Ser Gly Asn Leu Gln Asn Asn Thr<br>535                540                545 | 3296 | |
| cat caa gaa agc tcc gtt aat gaa gct gct cct cca cag gaa cca cta<br>His Gln Glu Ser Ser Val Asn Glu Ala Ala Pro Pro Gln Glu Pro Leu<br>      550                555                560 | 3344 | |
| aca aag tct tat ccg cgg gct aga aag agc agg caa gtg agc aca gca<br>Thr Lys Ser Tyr Pro Arg Ala Arg Lys Ser Arg Gln Val Ser Thr Ala<br>565                570                575 | 3392 | |
| agc agt gca agt ggg cga gag gga atc tcc ggt agc act tcc ttt cgt<br>Ser Ser Ala Ser Gly Arg Glu Gly Ile Ser Gly Ser Thr Ser Phe Arg<br>580                585                590              595 | 3440 | |
| cca ttc tca gcc gtt gat gag gat aac aac gat aac aac aac gac gca<br>Pro Phe Ser Ala Val Asp Glu Asp Asn Asn Asp Asn Asn Asn Asp Ala<br>              600                605              610 | 3488 | |
| cct gat caa atg atg aca acc acc acg acc acg aca aga aca act gtt<br>Pro Asp Gln Met Met Thr Thr Thr Thr Thr Thr Arg Thr Thr Val<br>      615                620                625 | 3536 | |
| act cag aca aca aga gat gga gga gaa gtg acg aga gtg ata aag gtg<br>Thr Gln Thr Thr Arg Asp Gly Gly Glu Val Thr Arg Val Ile Lys Val<br>              630                635              640 | 3584 | |
| gtt cct cac aat gcg aag ctc gct agt gag a at<br>Val Pro His Asn Ala Lys Leu Ala Ser Glu<br>645                650 | 3617 | |

```
<210> SEQ ID NO 15
<211> LENGTH: 430
<212> TYPE: DNA
<213> ORGANISM: Pisum sativum
<220> FEATURE:
<221> NAME/KEY: exon
<222> LOCATION: (2)..(13)
```

```
<223> OTHER INFORMATION: partial
<221> NAME/KEY: exon
<222> LOCATION: (95)..(430)
<223> OTHER INFORMATION: partial
<221> NAME/KEY: Intron
<222> LOCATION: (14)..(94)
<223> OTHER INFORMATION: partial

<400> SEQUENCE: 15
```

```
t aga ctg ata aag gtaaattatc tttgacattg atcagtgctc tcacacaccc         53
  Arg Leu Ile Lys
  1 ttgagtctta ctgtaatgat taattctttt tacttaagca g gtc caa caa cta att    109
                                              Val Gln Gln Leu Ile
                                                              5 gcc gga tcg cca gat ctt ttg ttt gat gat ggt gct ttt ctg gga aag     157
Ala Gly Ser Pro Asp Leu Leu Phe Asp Asp Gly Ala Phe Leu Gly Lys
10              15                  20                  25 tct ctt cca gat gga tct act cct aaa aaa ctc tca ttg gaa tat gtt     205
Ser Leu Pro Asp Gly Ser Thr Pro Lys Lys Leu Ser Leu Glu Tyr Val
                30                  35                  40 gta aaa gct cgg cta caa aat ctt aag cgc aaa gtt gat tct gaa aag     253
Val Lys Ala Arg Leu Gln Asn Leu Lys Arg Lys Val Asp Ser Glu Lys
            45                  50                  55 ata aat caa aac atg gaa tgt tct gca gag aat gct gtt ggt aaa aca     301
Ile Asn Gln Asn Met Glu Cys Ser Ala Glu Asn Ala Val Gly Lys Thr
        60                  65                  70 tct att tcg tcc gtg aaa aat acg agc cac ctt tct agt tcc atg cct     349
Ser Ile Ser Ser Val Lys Asn Thr Ser His Leu Ser Ser Ser Met Pro
75                  80                  85 ttt gcc gga aat cca cac caa gga aat gtg gca gct gat aat ggg atg     397
Phe Ala Gly Asn Pro His Gln Gly Asn Val Ala Ala Asp Asn Gly Met
90                  95                 100                 105 ggt ccc tgg tgt ttc aat cag tca cct ggg cat                         430
Gly Pro Trp Cys Phe Asn Gln Ser Pro Gly His
                110                 115
```

```
<210> SEQ ID NO 16
<211> LENGTH: 116
<212> TYPE: PRT
<213> ORGANISM: Pisum sativum

<400> SEQUENCE: 16

Arg Leu Ile Lys Val Gln Gln Leu Ile Ala Gly Ser Pro Asp Leu Leu
1               5                   10                  15

Phe Asp Asp Gly Ala Phe Leu Gly Lys Ser Leu Pro Asp Gly Ser Thr
                20                  25                  30

Pro Lys Lys Leu Ser Leu Glu Tyr Val Val Lys Ala Arg Leu Gln Asn
            35                  40                  45

Leu Lys Arg Lys Val Asp Ser Glu Lys Ile Asn Gln Asn Met Glu Cys
        50                  55                  60

Ser Ala Glu Asn Ala Val Gly Lys Thr Ser Ile Ser Ser Val Lys Asn
65                  70                  75                  80

Thr Ser His Leu Ser Ser Ser Met Pro Phe Ala Gly Asn Pro His Gln
                85                  90                  95

Gly Asn Val Ala Ala Asp Asn Gly Met Gly Pro Trp Cys Phe Asn Gln
            100                 105                 110

Ser Pro Gly His
        115
```

```
<210> SEQ ID NO 17
<211> LENGTH: 74
<212> TYPE: PRT
<213> ORGANISM: Broccoli/Cauliflower

<400> SEQUENCE: 17

Arg Leu Ile Met Val Gln Lys Met Val Ala Lys Ser Pro Asn Leu Val
1               5                   10                  15

Leu Lys Asn Lys Ile Asn Gly Gly Ser Lys Phe Lys Lys Pro Asn Thr
            20                  25                  30

Glu Asn Gln Lys Pro Val Thr Glu Ala Tyr Pro Glu His Met Lys Pro
        35                  40                  45

Lys Ile Pro Leu Pro Phe Ile Ser Lys Glu Leu Met Thr Pro Ile Trp
    50                  55                  60

Gln Gln Gln Leu Leu Pro Pro Gln Glu Asn
65                  70

<210> SEQ ID NO 18
<211> LENGTH: 555
<212> TYPE: DNA
<213> ORGANISM: Glycine max

<400> SEQUENCE: 18
acgcgtccga gcacctctca gtgctacttt catgaatccc gcctatcaat tcccagcttc      60
tcatccagta gttggggttt caccgtttgt ccctccggcc agtcacacct acttcgctcc     120
ctttggcatg ccggtaatga atcaagcaac atcaggatca gccgttgaac aggtgaacca     180
gtttgctgca caaggttctc atggtcaaaa tggtcattca tctgtagagg gagccgattt     240
taacactcat cataaccaaa gctcatctaa cttgccagtt cagaagaatg gagctaggtt     300
acatgttaaa aaatctcagg ccctgaagga gagagggtta caaggagca caagaagcag      360 tcctagtgaa atggcacagg gaatcagagc acggaaaatt gctgacggaa gtgatgcacg     420
tctctttctc ttcacgctga tgaaaccaga cagcaaacac aagccatcaa agttgtaccc     480
cataaccgga aatccgcgac ggaatcagca gctagaattg ttcaatccat tcaagaagag     540
agaaaacagc atgat                                                     555

<210> SEQ ID NO 19
<211> LENGTH: 185
<212> TYPE: PRT
<213> ORGANISM: Glycine max

<400> SEQUENCE: 19

Arg Val Arg Ala Pro Leu Ser Ala Thr Phe Met Asn Pro Ala Tyr Gln
1               5                   10                  15

Phe Pro Ala Ser His Pro Val Val Gly Val Ser Pro Phe Val Pro Pro
            20                  25                  30

Ala Ser His Thr Tyr Phe Ala Pro Phe Gly Met Pro Val Met Asn Gln
        35                  40                  45

Ala Thr Ser Gly Ser Ala Val Glu Gln Val Asn Gln Phe Ala Ala Gln
    50                  55                  60

Gly Ser His Gly Gln Asn Gly His Ser Ser Val Glu Gly Ala Asp Phe
65                  70                  75                  80

Asn Thr His His Asn Gln Ser Ser Ser Asn Leu Pro Val Gln Lys Asn
                85                  90                  95

Gly Ala Arg Leu His Val Lys Lys Ser Gln Ala Leu Lys Glu Arg Gly
            100                 105                 110
```

```
Leu Gln Gly Ser Thr Arg Ser Ser Pro Ser Glu Met Ala Gln Gly Ile
        115                 120                 125

Arg Ala Arg Lys Ile Ala Asp Gly Ser Asp Ala Gln Ser Leu Ser Leu
    130                 135                 140

His Ala Asp Glu Thr Arg Gln Gln Thr Gln Ala Ile Lys Val Val Pro
145                 150                 155                 160

His Asn Arg Lys Ser Ala Thr Glu Ser Ala Ala Arg Ile Val Gln Ser
                165                 170                 175

Ile Gln Glu Glu Arg Lys Gln His Asp
            180                 185

<210> SEQ ID NO 20
<211> LENGTH: 577
<212> TYPE: DNA
<213> ORGANISM: Lycopersicon esculentum

<400> SEQUENCE: 20
```

| | |
|---|---|
| tccattttca cacagtcgtt tgatcttttg ccgactcttc ccttgttttt ttttctcaac | 60 |
| tgtaatctct ttcttcatat tattgtgctt accaacaagg cctgttacat gatcacagaa | 120 |
| aaatataata gtaattttgt gaaattatac atctttttg cttctgtgtg cttcagaaat | 180 |
| ctcttgattt ctatgtaaag attgtgtttt gggtatttgg gtcggtagaa ttcttgtttt | 240 |
| tttaggtggg gtttgcttgg ttttcttcaa ttttgattgg ttttgttgaa agttcagaa | 300 |
| atttgatgta attgtacgga tttctttgaa ttttggaagt tgaatgtatg gtaaagtttc | 360 |
| gttttttttgg tttaatttaa tgaatgttgg agattgggtg aacctgttga gaagctatta | 420 |
| aagggaagaa atgaagagag gaagggtga agagaagttg atgggaccta tgtttccaag | 480 |
| gcttcatgtt aatgatacag aaaagggagg tccaaaagca cctccaagaa acaaaatggc | 540 |
| tctttatgag cagctcagta ttccttctca gagattc | 577 |

```
<210> SEQ ID NO 21
<211> LENGTH: 582
<212> TYPE: DNA
<213> ORGANISM: Lycopersicon esculentum
<220> FEATURE:
<221> NAME/KEY: 5'UTR
<222> LOCATION: (1)..(43)
<223> OTHER INFORMATION:
<221> NAME/KEY: exon
<222> LOCATION: (44)..(582)
<223> OTHER INFORMATION:

<400> SEQUENCE: 21
```

| | |
|---|---|
| attattcgtg agttttggag gctaactact gaggtagagg aag atg aaa aga ggt<br>                                                                                                                                            Met Lys Arg Gly<br>                                                                                                                                            1 | 55 |
| aca ggt gaa gag aaa gtt atg ggg cct atg ttt cca agg ctt aat gtt<br>Thr Gly Glu Glu Lys Val Met Gly Pro Met Phe Pro Arg Leu Asn Val<br>5                              10                           15                          20 | 103 |
| aat gat aca gaa aaa gga ggt cca aga gca cct cca agg aac aag atg<br>Asn Asp Thr Glu Lys Gly Gly Pro Arg Ala Pro Pro Arg Asn Lys Met<br>                        25                           30                           35 | 151 |
| gct ctt tat gaa caa ctg agt atc cct tcc caa cga tac aac cct ggt<br>Ala Leu Tyr Glu Gln Leu Ser Ile Pro Ser Gln Arg Tyr Asn Pro Gly<br>                    40                           45                           50 | 199 |
| gat ttg cct cat aac agt agt aac agt gca aat ttg gtc ctt cct cac<br>Asp Leu Pro His Asn Ser Ser Asn Ser Ala Asn Leu Val Leu Pro His<br>               55                           60                           65 | 247 |
| cca agc cag gag aat gaa cac gaa aga ggt gta tta ttc tct aga caa | 295 |

```
Pro Ser Gln Glu Asn Glu His Glu Arg Gly Val Leu Phe Ser Arg Gln
         70                  75                  80 ctt cct gca tta aga cat cca gtt gaa aag cca tat gga cgt agt tct       343
Leu Pro Ala Leu Arg His Pro Val Glu Lys Pro Tyr Gly Arg Ser Ser
 85                  90                  95                 100 ggt tca aat act cca ttg cgg gaa gtt aag tct aaa agg cag aca gaa       391
Gly Ser Asn Thr Pro Leu Arg Glu Val Lys Ser Lys Arg Gln Thr Glu
                105                 110                 115 aag gaa gat ttt aga gtt ccc act ttt gat aac tcc aag gag cgt gca       439
Lys Glu Asp Phe Arg Val Pro Thr Phe Asp Asn Ser Lys Glu Arg Ala
            120                 125                 130 gta aac aca gag gac tat tct aaa ggt acc tca gat ata gat aag cga       487
Val Asn Thr Glu Asp Tyr Ser Lys Gly Thr Ser Asp Ile Asp Lys Arg
135                 140                 145 gac agt act ttg aag cgg act gat caa ctc tcc cat gtc aca ccg aga       535
Asp Ser Thr Leu Lys Arg Thr Asp Gln Leu Ser His Val Thr Pro Arg
        150                 155                 160 gag aat ctt gtt aat acc ttt ggt gaa tca cat aag acc aat ata gt        582
Glu Asn Leu Val Asn Thr Phe Gly Glu Ser His Lys Thr Asn Ile
165                 170                 175

<210> SEQ ID NO 22
<211> LENGTH: 1347
<212> TYPE: DNA
<213> ORGANISM: Lycopersicon esculentum
<220> FEATURE:
<221> NAME/KEY: exon
<222> LOCATION: (2)..(1171)
<223> OTHER INFORMATION:
<221> NAME/KEY: 3'UTR
<222> LOCATION: (1172)..(1347)
<223> OTHER INFORMATION:

<400> SEQUENCE: 22 t ttg gac cga ggt gac gac tta tct gag act tcc aga gtg gaa tct att    49
  Leu Asp Arg Gly Asp Asp Leu Ser Glu Thr Ser Arg Val Glu Ser Ile
   1               5                  10                  15 tct gga aca gac atc tct cct gat gac att gta gga ata att ggc tta     97
Ser Gly Thr Asp Ile Ser Pro Asp Asp Ile Val Gly Ile Ile Gly Leu
             20                  25                  30 aag cgt ttc tgg aaa gcc aga aga gca att gtc aac cag caa aga gtg     145
Lys Arg Phe Trp Lys Ala Arg Arg Ala Ile Val Asn Gln Gln Arg Val
         35                  40                  45 ttt gca atc caa gtg ttc gag ttg cat cga cta ata aag gta caa agg     193
Phe Ala Ile Gln Val Phe Glu Leu His Arg Leu Ile Lys Val Gln Arg
     50                  55                  60 ctc att gcc ggg tca cca aat agt tcg ctc gaa gat cct gct tat tta     241
Leu Ile Ala Gly Ser Pro Asn Ser Ser Leu Glu Asp Pro Ala Tyr Leu
 65                  70                  75                  80 ggc aaa cct tta aag agt tca tcg atc aaa aga ctt cca ttg gac tgt     289
Gly Lys Pro Leu Lys Ser Ser Ser Ile Lys Arg Leu Pro Leu Asp Cys
                 85                  90                  95 att gtt aga gaa tct caa agt gtt ctg aag cgc aag cat gat tct gag     337
Ile Val Arg Glu Ser Gln Ser Val Leu Lys Arg Lys His Asp Ser Glu
            100                 105                 110 aag cct cac ttc agg atg gaa cac act gcc gaa agc aat gtg gga aag     385
Lys Pro His Phe Arg Met Glu His Thr Ala Glu Ser Asn Val Gly Lys
        115                 120                 125 gca tct ctc tct act gtg caa aat ggt agt caa ctc tct agc cac aaa     433
Ala Ser Leu Ser Thr Val Gln Asn Gly Ser Gln Leu Ser Ser His Lys
    130                 135                 140 cca ttt tca gga act cca ctg cct aca cct gta aca aat gat tct aat     481
```

-continued

```
Pro Phe Ser Gly Thr Pro Leu Pro Thr Pro Val Thr Asn Asp Ser Asn
145                 150                 155                 160 gcg ggt cct tgg tgc ttc caa caa cct tcc ggg cac caa tgg ttg atc      529
Ala Gly Pro Trp Cys Phe Gln Gln Pro Ser Gly His Gln Trp Leu Ile
                165                 170                 175 cca gtg atg tct cct tct gag gga ctt gta tac aag cca ttt tct gga      577
Pro Val Met Ser Pro Ser Glu Gly Leu Val Tyr Lys Pro Phe Ser Gly
            180                 185                 190 cct gga ttc acg agt cct att tgt gga agt ggg cct tca gga tcg agt      625
Pro Gly Phe Thr Ser Pro Ile Cys Gly Ser Gly Pro Ser Gly Ser Ser
        195                 200                 205 cca aca atg ggg aac ttt ttt gct cca aca tat gga gtt cct gct cct      673
Pro Thr Met Gly Asn Phe Phe Ala Pro Thr Tyr Gly Val Pro Ala Pro
    210                 215                 220 aat cct cac tat caa ggt atg gga gtt cct ttt gca cct ccg act ggt      721
Asn Pro His Tyr Gln Gly Met Gly Val Pro Phe Ala Pro Pro Thr Gly
225                 230                 235                 240 cat ggt tac ttt cgg caa tat ggc atg cca gct atg aat cca cca att      769
His Gly Tyr Phe Arg Gln Tyr Gly Met Pro Ala Met Asn Pro Pro Ile
                245                 250                 255 tca tca act gct agt gaa gaa tcg aac cag tat acc atg cct ggt tta      817
Ser Ser Thr Ala Ser Glu Glu Ser Asn Gln Tyr Thr Met Pro Gly Leu
            260                 265                 270 caa cac cag ttt tct gga gta gtt gat gac gtt caa cat tca aca tca      865
Gln His Gln Phe Ser Gly Val Val Asp Asp Val Gln His Ser Thr Ser
        275                 280                 285 gga ctc agt aat gtt cta aat cag aag aaa gaa aat gtc ccg gat gtt      913
Gly Leu Ser Asn Val Leu Asn Gln Lys Lys Glu Asn Val Pro Asp Val
    290                 295                 300 gta agg tat caa tcc aca aaa gat aat gag gta caa gcc agc agt gca      961
Val Arg Tyr Gln Ser Thr Lys Asp Asn Glu Val Gln Ala Ser Ser Ala
305                 310                 315                 320 agt agt cct att gag aca gca gga aga aac atg ctc tct ctt ttt ccc     1009
Ser Ser Pro Ile Glu Thr Ala Gly Arg Asn Met Leu Ser Leu Phe Pro
                325                 330                 335 acg tct cca gtt act gac aac cgt gat ggt agc cct cag gct tgt gtg     1057
Thr Ser Pro Val Thr Asp Asn Arg Asp Gly Ser Pro Gln Ala Cys Val
            340                 345                 350 cct gat aat cca gcc aga gtt atc aag gtt gta cct cac aat gca agg     1105
Pro Asp Asn Pro Ala Arg Val Ile Lys Val Val Pro His Asn Ala Arg
        355                 360                 365 tct gct aca gaa tcc gta gct cgg ata ttt cag tct ata caa caa gag     1153
Ser Ala Thr Glu Ser Val Ala Arg Ile Phe Gln Ser Ile Gln Gln Glu
    370                 375                 380 aga aat aat atg act tag gtttaacaca tctataagta gcttaccttg            1201
Arg Asn Asn Met Thr
385 tgaatatgac catttgctca tcctggcaaa atgtagtagt ttcagtcaat ttgttgtatc   1261 tttcttttct acagaaagta tgtaatagct gtatttttaat ttggttgctg tagataagca  1321 tacctgcaaa aaaaaaaaaa aaaaac                                        1347
```

<210> SEQ ID NO 23
<211> LENGTH: 389
<212> TYPE: PRT
<213> ORGANISM: Lycopersicon esculentum

<400> SEQUENCE: 23

```
Leu Asp Arg Gly Asp Asp Leu Ser Glu Thr Ser Arg Val Glu Ser Ile
1               5                   10                  15
```

-continued

```
Ser Gly Thr Asp Ile Ser Pro Asp Ile Val Gly Ile Ile Gly Leu
            20                  25                  30

Lys Arg Phe Trp Lys Ala Arg Arg Ala Ile Val Asn Gln Gln Arg Val
            35                  40                  45

Phe Ala Ile Gln Val Phe Glu Leu His Arg Leu Ile Lys Val Gln Arg
            50                  55                  60

Leu Ile Ala Gly Ser Pro Asn Ser Ser Leu Glu Asp Pro Ala Tyr Leu
 65                  70                  75                  80

Gly Lys Pro Leu Lys Ser Ser Ser Ile Lys Arg Leu Pro Leu Asp Cys
                     85                  90                  95

Ile Val Arg Glu Ser Gln Ser Val Leu Lys Arg Lys His Asp Ser Glu
                    100                 105                 110

Lys Pro His Phe Arg Met Glu His Thr Ala Glu Ser Asn Val Gly Lys
                    115                 120                 125

Ala Ser Leu Ser Thr Val Gln Asn Gly Ser Gln Leu Ser Ser His Lys
            130                 135                 140

Pro Phe Ser Gly Thr Pro Leu Pro Thr Pro Val Thr Asn Asp Ser Asn
145                 150                 155                 160

Ala Gly Pro Trp Cys Phe Gln Gln Pro Ser Gly His Gln Trp Leu Ile
                    165                 170                 175

Pro Val Met Ser Pro Ser Glu Gly Leu Val Tyr Lys Pro Phe Ser Gly
                    180                 185                 190

Pro Gly Phe Thr Ser Pro Ile Cys Gly Ser Gly Pro Ser Gly Ser Ser
                    195                 200                 205

Pro Thr Met Gly Asn Phe Phe Ala Pro Thr Tyr Gly Val Pro Ala Pro
            210                 215                 220

Asn Pro His Tyr Gln Gly Met Gly Val Pro Phe Ala Pro Pro Thr Gly
225                 230                 235                 240

His Gly Tyr Phe Arg Gln Tyr Gly Met Pro Ala Met Asn Pro Pro Ile
                    245                 250                 255

Ser Ser Thr Ala Ser Glu Glu Ser Asn Gln Tyr Thr Met Pro Gly Leu
            260                 265                 270

Gln His Gln Phe Ser Gly Val Val Asp Asp Val Gln His Ser Thr Ser
            275                 280                 285

Gly Leu Ser Asn Val Leu Asn Gln Lys Lys Glu Asn Val Pro Asp Val
            290                 295                 300

Val Arg Tyr Gln Ser Thr Lys Asp Asn Glu Val Gln Ala Ser Ser Ala
305                 310                 315                 320

Ser Ser Pro Ile Glu Thr Ala Gly Arg Asn Met Leu Ser Leu Phe Pro
                    325                 330                 335

Thr Ser Pro Val Thr Asp Asn Arg Asp Gly Ser Pro Gln Ala Cys Val
            340                 345                 350

Pro Asp Asn Pro Ala Arg Val Ile Lys Val Val Pro His Asn Ala Arg
            355                 360                 365

Ser Ala Thr Glu Ser Val Ala Arg Ile Phe Gln Ser Ile Gln Gln Glu
            370                 375                 380

Arg Asn Asn Met Thr
385

<210> SEQ ID NO 24
<211> LENGTH: 179
<212> TYPE: PRT
<213> ORGANISM: Lycopersicon esculentum
```

-continued

```
<400> SEQUENCE: 24

Met Lys Arg Gly Thr Gly Glu Glu Lys Val Met Gly Pro Met Phe Pro
1               5                   10                  15

Arg Leu Asn Val Asn Asp Thr Glu Lys Gly Gly Pro Arg Ala Pro Pro
            20                  25                  30

Arg Asn Lys Met Ala Leu Tyr Glu Gln Leu Ser Ile Pro Ser Gln Arg
        35                  40                  45

Tyr Asn Pro Gly Asp Leu Pro His Asn Ser Ser Asn Ser Ala Asn Leu
50                  55                  60

Val Leu Pro His Pro Ser Gln Glu Asn Glu His Glu Arg Gly Val Leu
65                  70                  75                  80

Phe Ser Arg Gln Leu Pro Ala Leu Arg His Pro Val Glu Lys Pro Tyr
                85                  90                  95

Gly Arg Ser Ser Gly Ser Asn Thr Pro Leu Arg Glu Val Lys Ser Lys
            100                 105                 110

Arg Gln Thr Glu Lys Glu Asp Phe Arg Val Pro Thr Phe Asp Asn Ser
        115                 120                 125

Lys Glu Arg Ala Val Asn Thr Glu Asp Tyr Ser Lys Gly Thr Ser Asp
130                 135                 140

Ile Asp Lys Arg Asp Ser Thr Leu Lys Arg Thr Asp Gln Leu Ser His
145                 150                 155                 160

Val Thr Pro Arg Glu Asn Leu Val Asn Thr Phe Gly Glu Ser His Lys
                165                 170                 175

Thr Asn Ile

<210> SEQ ID NO 25
<211> LENGTH: 49
<212> TYPE: PRT
<213> ORGANISM: Lycopersicon esculentum

<400> SEQUENCE: 25

Met Lys Arg Gly Lys Gly Glu Glu Lys Leu Met Gly Pro Met Phe Pro
1               5                   10                  15

Arg Leu His Val Asn Asp Thr Glu Lys Gly Gly Pro Lys Ala Pro Pro
            20                  25                  30

Arg Asn Lys Met Ala Leu Tyr Glu Gln Leu Ser Ile Pro Ser Gln Arg
        35                  40                  45

Phe

<210> SEQ ID NO 26
<211> LENGTH: 4478
<212> TYPE: DNA
<213> ORGANISM: Oryza sativa
<220> FEATURE:
<221> NAME/KEY: exon
<222> LOCATION: (1)..(261)
<223> OTHER INFORMATION:
<221> NAME/KEY: exon
<222> LOCATION: (1660)..(2645)
<223> OTHER INFORMATION:
<221> NAME/KEY: exon
<222> LOCATION: (3330)..(3381)
<223> OTHER INFORMATION:
<221> NAME/KEY: exon
<222> LOCATION: (3495)..(4478)
<223> OTHER INFORMATION:
<221> NAME/KEY: Intron
<222> LOCATION: (262)..(1659)
<223> OTHER INFORMATION:
<221> NAME/KEY: Intron
<222> LOCATION: (2646)..(3329)
```

-continued

```
<223> OTHER INFORMATION:
<221> NAME/KEY: Intron
<222> LOCATION: (3382)..(3494)
<223> OTHER INFORMATION:

<400> SEQUENCE: 26 atg gcg acg agg gga gga ggc gga gga gga gga ggg aag gag gcg aag      48
Met Ala Thr Arg Gly Gly Gly Gly Gly Gly Gly Gly Lys Glu Ala Lys
1               5                   10                  15 ggg aag gtg atg ggc ccg ctg ttc ccg cgg ctc cac gtc aac gac gcg      96
Gly Lys Val Met Gly Pro Leu Phe Pro Arg Leu His Val Asn Asp Ala
            20                  25                  30 gcc aag ggc gga ggc ccg cgg gcg ccg ccc cgg aac aag atg gcg ctc     144
Ala Lys Gly Gly Gly Pro Arg Ala Pro Pro Arg Asn Lys Met Ala Leu
        35                  40                  45 tac gag cag ttc acc gtg ccc tcg cat cgc ttc agc ggc gga gga ggc     192
Tyr Glu Gln Phe Thr Val Pro Ser His Arg Phe Ser Gly Gly Gly Gly
    50                  55                  60 ggc ggc gga gta gga ggc agc ccc gcg cac tcg acg tcg gcg gcg agc     240
Gly Gly Gly Val Gly Gly Ser Pro Ala His Ser Thr Ser Ala Ala Ser
65                  70                  75                  80 cag agc cag agc cag agc cag gtgactcgac gtcctgcccg tatgatcgat        291
Gln Ser Gln Ser Gln Ser Gln
                85 tcgattgggg gtagtgtgtg cgactgctaa attggtacta gtaggcgaca attctgtgca   351 aatggagcta aacgccttgc aaatcgaatc gaattagaag cctaaattgg taggcaataa   411 ttctgtgcaa tggagctaaa cttccttgca aatcgaatag aactaaaagc tgggaagata   471 atttcgaggc acaaatggtg ccctcgacgt cgacgagcta ggtcagaggg ggcgtttcac   531 gccttaccct ttgtagttat ctcggttggg atagatgaat tgatgggcga atttagtgca   591 acggagctaa acacatggaa aaattggata agattaaggc cgagaagccc agtttgaggc   651 acaaatgcca tgttcctttt gtgctgatta atctatcatg ccgtcgacat gtgattcaat   711 tacttgcaaa tatagtcata caattgtggt aggagtaaca tgcttgcacg ttgtcatagt   771 gtcattattg atctttctcc gtgctgataa ctcacttgtg ttgaaggcga aagagcagaa   831 caaaccatt atatgcagtt tacatcagct cttccggtaa agttttggag acggggcata    891 agttccttgc aaacaatatc ggatattata gcttattgca aattgtatat ggccagatat   951 gctatgattg tgtttgctga ggtctggtgt ttgtaatata caaacaaaaa ggtccacatg  1011 tgaaactgca tgtagcgcag gtggcaaaga gtagccgtag tgctgctcaa cgtactgtgt  1071 tctattctcc ctgacgtgct caccttcctt aaatcattga cactaggttc ctccttagtg  1131 tcttgcattt ttgcctgccg aaaaaaaaag gtccacgtga aagggaatga taaaaatggt  1191 ggttgatatg ctttgattgt caggcacacg ttcaacctgt atgtgataaa tcaacggt    1251 tttctaatac tgttttcagc aaggatttag gagtggaaaa tattctttag aacaaatctg  1311 caatagcctc ccacaacaca tccaactacc ttttgataat gggatagtta tagacatgaa  1371 gtgcgaatgg caaaagtcca agtcatagat ttccaaatga agaaatgtga acaaaataag  1431 aaagaaagaa gtccatttgc agtattatgt ctcttttgcc cttctttggg tcgaaaataa  1491 aataaaaaat cgagatctta ccatgagata cttaatctcc caccactttt tctaattcaa  1551 catggaagtt cttggatagt ttaaatacgc ttcctaccaa ttagcgtgga atcctcgcaa  1611 tttttcacta aatctagtag tactgaaatg gattttattt tcttccag gtt tat gga  1668
                                                   Val Tyr Gly
                                                           90
```

-continued

```
cgt gac agt tct ctg ttc cag ccg ttc aat gtg cct tcc aat cga cct      1716
Arg Asp Ser Ser Leu Phe Gln Pro Phe Asn Val Pro Ser Asn Arg Pro
             95                 100                 105 ggc cat tct act gaa aag atc aat tca gat aag atc aac aag aag att      1764
Gly His Ser Thr Glu Lys Ile Asn Ser Asp Lys Ile Asn Lys Lys Ile
        110                 115                 120 agt ggt tca aga aaa gaa ctg ggg atg tta tcc tct cag act aag ggc      1812
Ser Gly Ser Arg Lys Glu Leu Gly Met Leu Ser Ser Gln Thr Lys Gly
125                 130                 135 atg gat att tat gct tca aga tca act gct gag gca cca caa aga aga      1860
Met Asp Ile Tyr Ala Ser Arg Ser Thr Ala Glu Ala Pro Gln Arg Arg
        140                 145                 150 gca gaa aat aca ata aag agt tct tcg gga aag aga ttg gcc gat gat      1908
Ala Glu Asn Thr Ile Lys Ser Ser Ser Gly Lys Arg Leu Ala Asp Asp
155                 160                 165                 170 gat gaa ttt atg gtt cct tct gtc ttc aat tcc aga ttt cct caa tat      1956
Asp Glu Phe Met Val Pro Ser Val Phe Asn Ser Arg Phe Pro Gln Tyr
            175                 180                 185 agt act caa gag aat gca ggg gtt caa gac caa tca aca ccc ctt gtt      2004
Ser Thr Gln Glu Asn Ala Gly Val Gln Asp Gln Ser Thr Pro Leu Val
        190                 195                 200 gct gca aat cca cac aaa agc cct tca aca gtg tcc aaa tca tcc aca      2052
Ala Ala Asn Pro His Lys Ser Pro Ser Thr Val Ser Lys Ser Ser Thr
205                 210                 215 aag tgt tat aac act gtt agc aag aaa ttg gag aga atc cat gtt tct      2100
Lys Cys Tyr Asn Thr Val Ser Lys Lys Leu Glu Arg Ile His Val Ser
            220                 225                 230 gat gtg aaa tca agg acc cct ttg aaa gac aag gag atg gaa gca gca      2148
Asp Val Lys Ser Arg Thr Pro Leu Lys Asp Lys Glu Met Glu Ala Ala
235                 240                 245                 250 cag aca tcc aaa aac gtg gaa gtt gaa aaa agt tca tcc ttt cat gct      2196
Gln Thr Ser Lys Asn Val Glu Val Glu Lys Ser Ser Ser Phe His Ala
            255                 260                 265 tcc aaa gat atg ttt gaa agc agg cat gct aaa gta tat cct aag atg      2244
Ser Lys Asp Met Phe Glu Ser Arg His Ala Lys Val Tyr Pro Lys Met
        270                 275                 280 gat aag acg ggc att ata aat gat tct gat gag cca cat ggt gga aat      2292
Asp Lys Thr Gly Ile Ile Asn Asp Ser Asp Glu Pro His Gly Gly Asn
        285                 290                 295 agt ggg cat caa gcg aca agc aga aat gga ggt tcc atg aaa ttt cag      2340
Ser Gly His Gln Ala Thr Ser Arg Asn Gly Gly Ser Met Lys Phe Gln
300                 305                 310 aac cct cca atg aga aga aat gaa att tcc tct aat cca tct tct gaa      2388
Asn Pro Pro Met Arg Arg Asn Glu Ile Ser Ser Asn Pro Ser Ser Glu
315                 320                 325                 330 aat act gat agg cat tat aat tta ccg caa gga ggc ata gag gaa aca      2436
Asn Thr Asp Arg His Tyr Asn Leu Pro Gln Gly Gly Ile Glu Glu Thr
            335                 340                 345 ggt aca aag aga aaa agg ttg cta gaa caa cac gat gca gag aaa agt      2484
Gly Thr Lys Arg Lys Arg Leu Leu Glu Gln His Asp Ala Glu Lys Ser
        350                 355                 360 gat gat gtg tca agg ttg cta gaa caa cac gat gca gag aac att gat      2532
Asp Asp Val Ser Arg Leu Leu Glu Gln His Asp Ala Glu Asn Ile Asp
        365                 370                 375 gat gtg tct gat tcc tcg gtg gag tgt ata act ggt tgg gag att tct      2580
Asp Val Ser Asp Ser Ser Val Glu Cys Ile Thr Gly Trp Glu Ile Ser
380                 385                 390 cca gat aaa att gtt gga gcc att ggt aca aag cat ttc tgg aaa gca      2628
Pro Asp Lys Ile Val Gly Ala Ile Gly Thr Lys His Phe Trp Lys Ala
395                 400                 405                 410
```

```
                                                          -continued aga cgt gct att atg aa  gtaagtaaaa ctatccttt gagcttagtt                    2675
Arg Arg Ala Ile Met Asn
                415 tggcccactc aaactagact tgtttgcagc tctaattacg tataggtagc tttgatgaat          2735 aaaatttgtt ttgtttccct tgctttactg ttatttgctc ttaatttgcg gttgatctta          2795 atcatcttag acagaaaaac atgatgacta tctcgtttgt ttttggttta tttcatattt          2855 gaatgccaat agatgtcagc tccagatgat atttcaaata cctcatgcat ggaaactgtg          2915 catacttatg ccaaattttg ggcttacaag tcagcatgtc tacaaatttc tttggcagaa          2975 ttaatatata tctagttcaa catttgctga tttgtaattg gattagttgt ctgcagaatg          3035 ccggcatgtt ttatttcct  ttcaactagg tcaatcagtt ttgttgttgt ctgttgttct          3095 tgtccaccta cacctgtact actgaaatgt tctcttttgg agatgtcaat gaaaatttta          3155 atctatagtg gtttcaattt tattttcatt ttagtcaaga agaatggcat aatctcattt          3215 aaaaagattg taaagtgtc  cctgttaaag tgatattgta ggtattgctt taccaagcta          3275 ctgtatgatt ccctttattg ttttacactc taatcttctt taaactctat gcag t caa         3333
                                                              Gln cag agg gtg ttt gct gtc cag gtt ttt gag ctg cat aag ttg gta aaa            3381
Gln Arg Val Phe Ala Val Gln Val Phe Glu Leu His Lys Leu Val Lys
    420                 425                 430 gtgagtctag caaatttctc ttccttctag ccactcttaa gcaggttaat tcgtggatag          3441
gattttgtcc ataatctgtt tataacccac acttgtattt gacttacaat cag gtg            3497
                                                              Val cag aag ttg att gca gca tcg cca cat gta ctt att gaa agt gat cct            3545
Gln Lys Leu Ile Ala Ala Ser Pro His Val Leu Ile Glu Ser Asp Pro
435                 440                 445                 450 tgc ctt ggc aat gcc ttg ttg ggt agc aag aac aag ctg gtg gaa gaa            3593
Cys Leu Gly Asn Ala Leu Leu Gly Ser Lys Asn Lys Leu Val Glu Glu
                455                 460                 465 aac ctg aaa gca caa cct ctt tta gtc gca acc atc gat gac gtg gag            3641
Asn Leu Lys Ala Gln Pro Leu Leu Val Ala Thr Ile Asp Asp Val Glu
            470                 475                 480 cca agt cta cag caa ccg gag gta tca aaa gaa aac act gaa gac agc            3689
Pro Ser Leu Gln Gln Pro Glu Val Ser Lys Glu Asn Thr Glu Asp Ser
        485                 490                 495 cca ccc tcc cct cat gat act ggg ctt ggc agt ggt caa cgt gat caa            3737
Pro Pro Ser Pro His Asp Thr Gly Leu Gly Ser Gly Gln Arg Asp Gln
    500                 505                 510 gct gca aca aat ggc gtc tct aaa agc aat cgt cga gct aca cct gtt            3785
Ala Ala Thr Asn Gly Val Ser Lys Ser Asn Arg Arg Ala Thr Pro Val
515                 520                 525                 530 gct tct gat aac aaa caa aat aac tgg ggc gtt caa ctt caa cca cct            3833
Ala Ser Asp Asn Lys Gln Asn Asn Trp Gly Val Gln Leu Gln Pro Pro
                535                 540                 545 caa aat caa tgg ctt gtc cct gtc atg tct cct ttg gaa ggc ctt gtc            3881
Gln Asn Gln Trp Leu Val Pro Val Met Ser Pro Leu Glu Gly Leu Val
            550                 555                 560 tat aag cct tat tct ggt ccg tgc cct cca gct ggt agc ata ttg gcc            3929
Tyr Lys Pro Tyr Ser Gly Pro Cys Pro Pro Ala Gly Ser Ile Leu Ala
        565                 570                 575 ccg ttt tat gcc aac tgt act cct ttg agt ctt cca tca aca gct gga            3977
Pro Phe Tyr Ala Asn Cys Thr Pro Leu Ser Leu Pro Ser Thr Ala Gly
    580                 585                 590 gat ttc atg aac tcg gca tac ggt gtt cct atg cct cat cag cca caa            4025
Asp Phe Met Asn Ser Ala Tyr Gly Val Pro Met Pro His Gln Pro Gln
```

-continued

```
                    595                 600                 605                 610
cat atg ggt gct cct ggc cct cct tcc atg cct atg aac tac ttc ccg              4073
His Met Gly Ala Pro Gly Pro Pro Ser Met Pro Met Asn Tyr Phe Pro
                615                 620                 625 cct ttc agc ata cca gtg atg aac cca act gca ccg gca cct gta gtc              4121
Pro Phe Ser Ile Pro Val Met Asn Pro Thr Ala Pro Ala Pro Val Val
            630                 635                 640 gaa caa ggg aga cat cct tcg atg cca cag cct tat ggg aac ttt gag              4169
Glu Gln Gly Arg His Pro Ser Met Pro Gln Pro Tyr Gly Asn Phe Glu
        645                 650                 655 cag cag tcg tgg atc tca tgt aac atg tca cat cca agt ggc att tgg              4217
Gln Gln Ser Trp Ile Ser Cys Asn Met Ser His Pro Ser Gly Ile Trp
    660                 665                 670 aga ttt cat gcc tca aga gat agc gag gca cag gcc agc agc gct agc              4265
Arg Phe His Ala Ser Arg Asp Ser Glu Ala Gln Ala Ser Ser Ala Ser
675                 680                 685                 690 agt cct ttt gac agg ttc caa tgc agt gga agt ggt cct gta tcc gcc              4313
Ser Pro Phe Asp Arg Phe Gln Cys Ser Gly Ser Gly Pro Val Ser Ala
                695                 700                 705 ttc ccc aca gta tca gct cag aac aac cag cct cag ccc tca tat agc              4361
Phe Pro Thr Val Ser Ala Gln Asn Asn Gln Pro Gln Pro Ser Tyr Ser
            710                 715                 720 agc cgg gac aac cag acc aat gtt atc aag gtt gtt cca cat aat tca              4409
Ser Arg Asp Asn Gln Thr Asn Val Ile Lys Val Val Pro His Asn Ser
        725                 730                 735 cga act gct tca gag tca gca gca cgg att ttc cgg tca ata caa atg              4457
Arg Thr Ala Ser Glu Ser Ala Ala Arg Ile Phe Arg Ser Ile Gln Met
    740                 745                 750 gaa cgg caa cga gat gat tga                                                  4478
Glu Arg Gln Arg Asp Asp
755                 760

<210> SEQ ID NO 27
<211> LENGTH: 760
<212> TYPE: PRT
<213> ORGANISM: Oryza sativa

<400> SEQUENCE: 27

Met Ala Thr Arg Gly Gly Gly Gly Gly Gly Lys Glu Ala Lys
1               5                   10                  15

Gly Lys Val Met Gly Pro Leu Phe Pro Arg Leu His Val Asn Asp Ala
                20                  25                  30

Ala Lys Gly Gly Gly Pro Arg Ala Pro Pro Arg Asn Lys Met Ala Leu
            35                  40                  45

Tyr Glu Gln Phe Thr Val Pro Ser His Arg Phe Ser Gly Gly Gly Gly
        50                  55                  60

Gly Gly Gly Val Gly Gly Ser Pro Ala His Ser Thr Ser Ala Ala Ser
65                  70                  75                  80

Gln Ser Gln Ser Gln Ser Gln Val Tyr Gly Arg Asp Ser Ser Leu Phe
                85                  90                  95

Gln Pro Phe Asn Val Pro Ser Asn Arg Pro Gly His Ser Thr Glu Lys
            100                 105                 110

Ile Asn Ser Asp Lys Ile Asn Lys Lys Ile Ser Gly Ser Arg Lys Glu
        115                 120                 125

Leu Gly Met Leu Ser Ser Gln Thr Lys Gly Met Asp Ile Tyr Ala Ser
    130                 135                 140

Arg Ser Thr Ala Glu Ala Pro Gln Arg Arg Ala Glu Asn Thr Ile Lys
145                 150                 155                 160
```

```
Ser Ser Ser Gly Lys Arg Leu Ala Asp Asp Glu Phe Met Val Pro
            165                 170                 175

Ser Val Phe Asn Ser Arg Phe Pro Gln Tyr Ser Thr Gln Glu Asn Ala
            180                 185                 190

Gly Val Gln Asp Gln Ser Thr Pro Leu Val Ala Ala Asn Pro His Lys
            195                 200                 205

Ser Pro Ser Thr Val Ser Lys Ser Ser Thr Lys Cys Tyr Asn Thr Val
    210                 215                 220

Ser Lys Lys Leu Glu Arg Ile His Val Ser Asp Val Lys Ser Arg Thr
225                 230                 235                 240

Pro Leu Lys Asp Lys Glu Met Glu Ala Ala Gln Thr Ser Lys Asn Val
            245                 250                 255

Glu Val Glu Lys Ser Ser Ser Phe His Ala Ser Lys Asp Met Phe Glu
            260                 265                 270

Ser Arg His Ala Lys Val Tyr Pro Lys Met Asp Lys Thr Gly Ile Ile
            275                 280                 285

Asn Asp Ser Asp Glu Pro His Gly Gly Asn Ser Gly His Gln Ala Thr
    290                 295                 300

Ser Arg Asn Gly Gly Ser Met Lys Phe Gln Asn Pro Pro Met Arg Arg
305                 310                 315                 320

Asn Glu Ile Ser Ser Asn Pro Ser Ser Glu Asn Thr Asp Arg His Tyr
            325                 330                 335

Asn Leu Pro Gln Gly Gly Ile Glu Glu Thr Gly Thr Lys Arg Lys Arg
            340                 345                 350

Leu Leu Glu Gln His Asp Ala Glu Lys Ser Asp Asp Val Ser Arg Leu
            355                 360                 365

Leu Glu Gln His Asp Ala Glu Asn Ile Asp Asp Val Ser Asp Ser Ser
            370                 375                 380

Val Glu Cys Ile Thr Gly Trp Glu Ile Ser Pro Asp Lys Ile Val Gly
385                 390                 395                 400

Ala Ile Gly Thr Lys His Phe Trp Lys Ala Arg Arg Ala Ile Met Asn
            405                 410                 415

Gln Gln Arg Val Phe Ala Val Gln Val Phe Glu Leu His Lys Leu Val
            420                 425                 430

Lys Val Gln Lys Leu Ile Ala Ala Ser Pro His Val Leu Ile Glu Ser
            435                 440                 445

Asp Pro Cys Leu Gly Asn Ala Leu Leu Gly Ser Lys Asn Lys Leu Val
    450                 455                 460

Glu Glu Asn Leu Lys Ala Gln Pro Leu Leu Val Ala Thr Ile Asp Asp
465                 470                 475                 480

Val Glu Pro Ser Leu Gln Gln Pro Glu Val Ser Lys Glu Asn Thr Glu
            485                 490                 495

Asp Ser Pro Pro Ser Pro His Asp Thr Gly Leu Gly Ser Gly Gln Arg
            500                 505                 510

Asp Gln Ala Ala Thr Asn Gly Val Ser Lys Ser Asn Arg Arg Ala Thr
            515                 520                 525

Pro Val Ala Ser Asp Asn Lys Gln Asn Asn Trp Gly Val Gln Leu Gln
    530                 535                 540

Pro Pro Gln Asn Gln Trp Leu Val Pro Val Met Ser Pro Leu Glu Gly
545                 550                 555                 560

Leu Val Tyr Lys Pro Tyr Ser Gly Pro Cys Pro Pro Ala Gly Ser Ile
            565                 570                 575
```

-continued

```
Leu Ala Pro Phe Tyr Ala Asn Cys Thr Pro Leu Ser Leu Pro Ser Thr
            580                 585                 590

Ala Gly Asp Phe Met Asn Ser Ala Tyr Gly Val Pro Met Pro His Gln
            595                 600                 605

Pro Gln His Met Gly Ala Pro Gly Pro Pro Ser Met Pro Met Asn Tyr
            610                 615                 620

Phe Pro Pro Phe Ser Ile Pro Val Met Asn Pro Thr Ala Pro Ala Pro
625                 630                 635                 640

Val Val Glu Gln Gly Arg His Pro Ser Met Pro Gln Pro Tyr Gly Asn
                    645                 650                 655

Phe Glu Gln Gln Ser Trp Ile Ser Cys Asn Met Ser His Pro Ser Gly
            660                 665                 670

Ile Trp Arg Phe His Ala Ser Arg Asp Ser Glu Ala Gln Ala Ser Ser
            675                 680                 685

Ala Ser Ser Pro Phe Asp Arg Phe Gln Cys Ser Gly Ser Gly Pro Val
            690                 695                 700

Ser Ala Phe Pro Thr Val Ser Ala Gln Asn Asn Gln Pro Gln Pro Ser
705                 710                 715                 720

Tyr Ser Ser Arg Asp Asn Gln Thr Asn Val Ile Lys Val Val Pro His
                    725                 730                 735

Asn Ser Arg Thr Ala Ser Glu Ser Ala Ala Arg Ile Phe Arg Ser Ile
            740                 745                 750

Gln Met Glu Arg Gln Arg Asp Asp
            755                 760

<210> SEQ ID NO 28
<211> LENGTH: 938
<212> TYPE: DNA
<213> ORGANISM: Zea mays

<400> SEQUENCE: 28
gacgtggagc aaaacgatga tctgtctgat tcctctgttg aatctttgcc tggaatggag     60
atttctccag atgatgttgt cagtgctatt ggtcccaagc attttttggaa agcgagaaga   120
gctattgtca atcagcagag ggtatttgct gttcaagtat tcgagctgca taggttgatc   180
aaagtgcaga agttgatcgc tgcatctcca catgtactta ttgaggggga tccttgcctt   240
ggcaaatcct tggcggtgag cmagaaaagg ctgaagtcag tggctgattc ccgtwatgtc   300
cccgtttgaa ggacttgtct acaagcctta tcccgggsca ytgccctccg gtggaagtct   360
tttggcgccc ccatttttg ccagctaccc cacctcttcc tcctccacag ctggggggga   420
tttcatgagt tcggcatgtg gagccaggct gatgagtgcc cctgtgtact tcccgtcttt   480
cagcatgcct gcagtgtcag ggtctgcagt tgagcaagtg agccatgttg cagcgtcgca   540
gcataaacgg aactcgtgta gtgaagcggt gttggcatca agggacagcg aggtgcaagg   600
cagtagtgct agcagtccgg catcttctga acagcagct caacccaggg tcattagggt    660
tgttccccac acggcacgca cggcttcaga gtcggcagca aggattttcc gctcaataca   720
gatggagagg aaacaaaacg acccgtgact ggcagataaa aatgaaagaa cggagggagt   780
agactaattt tttgaccgat aattataatg atcgccgtaa attggctggc ccgcccgcct   840
tatgttttt gttcagtgta aatatgctgt gtctgtcaga atgatatggc atctgtagct   900
attttggttc tgtcagaatc atgttgattg gaattaaa                           938

<210> SEQ ID NO 29
<211> LENGTH: 248
```

```
<212> TYPE: PRT
<213> ORGANISM: Zea mays
<220> FEATURE:
<221> NAME/KEY: UNSURE
<222> LOCATION: (88)..(88)
<223> OTHER INFORMATION:
<221> NAME/KEY: unsure
<222> LOCATION: (98)..(98)
<223> OTHER INFORMATION: amino acid not confirmed, based on nucleic
      acid sequence
<221> NAME/KEY: unsure
<222> LOCATION: (113)..(113)
<223> OTHER INFORMATION: amino acid not confirmed, based on nucleic
      acid sequence
<221> NAME/KEY: unsure
<222> LOCATION: (114)..(114)
<223> OTHER INFORMATION: amino acid not confirmed, based on nucleic
      acid sequence
```

<400> SEQUENCE: 29

Asp Val Glu Gln Asn Asp Asp Leu Ser Asp Ser Val Glu Ser Leu
1               5                   10                  15

Pro Gly Met Glu Ile Ser Pro Asp Val Val Ser Ala Ile Gly Pro
            20                  25                  30

Lys His Phe Trp Lys Ala Arg Ala Ile Val Asn Gln Gln Arg Val
        35                  40                  45

Phe Ala Val Gln Val Phe Glu Leu His Arg Leu Ile Lys Val Gln Lys
    50                  55                  60

Leu Ile Ala Ala Ser Pro His Val Leu Ile Glu Gly Asp Pro Cys Leu
65                  70                  75                  80

Gly Lys Ser Leu Ala Val Ser Xaa Lys Arg Leu Ser Gln Trp Leu Ile
                85                  90                  95

Pro Xaa Met Ser Pro Phe Glu Gly Leu Val Tyr Lys Pro Tyr Pro Gly
            100                 105                 110

Xaa Xaa Pro Ser Gly Gly Ser Leu Leu Ala Pro Pro Phe Phe Ala Ser
        115                 120                 125

Tyr Pro Thr Ser Ser Ser Ser Thr Ala Gly Gly Asp Phe Met Ser Ser
    130                 135                 140

Ala Cys Gly Ala Arg Leu Met Ser Ala Pro Val Tyr Phe Pro Ser Phe
145                 150                 155                 160

Ser Met Pro Ala Val Ser Gly Ser Ala Val Glu Gln Val Ser His Val
                165                 170                 175

Ala Ala Ser Gln His Lys Arg Asn Ser Cys Ser Glu Ala Val Leu Ala
            180                 185                 190

Ser Arg Asp Ser Glu Val Gln Gly Ser Ser Ala Ser Ser Pro Ala Ser
        195                 200                 205

Ser Glu Thr Ala Ala Gln Pro Arg Val Ile Arg Val Val Pro His Thr
    210                 215                 220

Ala Arg Thr Ala Ser Glu Ser Ala Ala Arg Ile Phe Arg Ser Ile Gln
225                 230                 235                 240

Met Glu Arg Lys Gln Asn Asp Pro
                245

```
<210> SEQ ID NO 30
<211> LENGTH: 625
<212> TYPE: DNA
<213> ORGANISM: Zea mays
<220> FEATURE:
<221> NAME/KEY: exon
<222> LOCATION: (1)..(570)
<223> OTHER INFORMATION:
<221> NAME/KEY: 3'UTR
```

```
<222> LOCATION: (571)..(625)
<223> OTHER INFORMATION:

<400> SEQUENCE: 30 gca cga ggg cac atg gtc cct cct ggc gcc cct gcc atg cat atg aac      48
Ala Arg Gly His Met Val Pro Pro Gly Ala Pro Ala Met His Met Asn
1               5                   10                  15 tac ttc ccg cct ttc agt atg cca gtg atg aat cca gga aca cca gca      96
Tyr Phe Pro Pro Phe Ser Met Pro Val Met Asn Pro Gly Thr Pro Ala
            20                  25                  30 tct gca gtg gag caa ggg agc cat gct gct gcg cca cag cct cat ggg     144
Ser Ala Val Glu Gln Gly Ser His Ala Ala Ala Pro Gln Pro His Gly
        35                  40                  45 cac atg gac cag cag tcg ctg atc tca tgt aac atg tca cac ccg agt     192
His Met Asp Gln Gln Ser Leu Ile Ser Cys Asn Met Ser His Pro Ser
    50                  55                  60 ggc gtt tgg agg ttt ctt gca tca agg gac agc gag cca cag gcc agc     240
Gly Val Trp Arg Phe Leu Ala Ser Arg Asp Ser Glu Pro Gln Ala Ser
65                  70                  75                  80 agc gcc acc agc cct ttc gac agg ctc caa gtc caa ggt gat gga agt     288
Ser Ala Thr Ser Pro Phe Asp Arg Leu Gln Val Gln Gly Asp Gly Ser
                85                  90                  95 gct ccg ttg tca ttc ttt ccc acg gct tca gct ccg aat gtc cag cct     336
Ala Pro Leu Ser Phe Phe Pro Thr Ala Ser Ala Pro Asn Val Gln Pro
            100                 105                 110 ccg ccc tca tct gga ggc cgg gac cgg gac cag cag aac cat gta atc     384
Pro Pro Ser Ser Gly Gly Arg Asp Arg Asp Gln Gln Asn His Val Ile
        115                 120                 125 agg gtt gtt ccg cgt aac gca cag act gct tca gtc ccg aaa gcc caa     432
Arg Val Val Pro Arg Asn Ala Gln Thr Ala Ser Val Pro Lys Ala Gln
    130                 135                 140 cct cag ccg tca tcc gga ggc cgg gac caa aag aac cat gta atc agg     480
Pro Gln Pro Ser Ser Gly Gly Arg Asp Gln Lys Asn His Val Ile Arg
145                 150                 155                 160 gtt gtt ccg cat aac gcg cag act gct tcg gag tca gca gcg tgg atc     528
Val Val Pro His Asn Ala Gln Thr Ala Ser Glu Ser Ala Ala Trp Ile
                165                 170                 175 ttc cgg tca ata caa atg gag agg aac caa aat gat tcg tag             570
Phe Arg Ser Ile Gln Met Glu Arg Asn Gln Asn Asp Ser
            180                 185 ctggttacca tatactttcg tgtcatccga tggcagctta gtgcagcatt gcagt        625

<210> SEQ ID NO 31
<211> LENGTH: 189
<212> TYPE: PRT
<213> ORGANISM: Zea mays

<400> SEQUENCE: 31

Ala Arg Gly His Met Val Pro Pro Gly Ala Pro Ala Met His Met Asn
1               5                   10                  15

Tyr Phe Pro Pro Phe Ser Met Pro Val Met Asn Pro Gly Thr Pro Ala
            20                  25                  30

Ser Ala Val Glu Gln Gly Ser His Ala Ala Ala Pro Gln Pro His Gly
        35                  40                  45

His Met Asp Gln Gln Ser Leu Ile Ser Cys Asn Met Ser His Pro Ser
    50                  55                  60

Gly Val Trp Arg Phe Leu Ala Ser Arg Asp Ser Glu Pro Gln Ala Ser
65                  70                  75                  80

Ser Ala Thr Ser Pro Phe Asp Arg Leu Gln Val Gln Gly Asp Gly Ser
```

-continued

```
                          85                  90                  95
        Ala Pro Leu Ser Phe Phe Pro Thr Ala Ser Ala Pro Asn Val Gln Pro
                    100                 105                 110

Pro Pro Ser Ser Gly Gly Arg Asp Arg Asp Gln Gln Asn His Val Ile
                    115                 120                 125

Arg Val Val Pro Arg Asn Ala Gln Thr Ala Ser Val Pro Lys Ala Gln
                130                 135                 140

Pro Gln Pro Ser Ser Gly Gly Arg Asp Gln Lys Asn His Val Ile Arg
        145                 150                 155                 160

Val Val Pro His Asn Ala Gln Thr Ala Ser Glu Ser Ala Ala Trp Ile
                        165                 170                 175

Phe Arg Ser Ile Gln Met Glu Arg Asn Gln Asn Asp Ser
                    180                 185
```

```
<210> SEQ ID NO 32
<211> LENGTH: 2794
<212> TYPE: DNA
<213> ORGANISM: Arabidopsis thaliana
<220> FEATURE:
<221> NAME/KEY: 5'UTR
<222> LOCATION: (1)..(476)
<223> OTHER INFORMATION:
<221> NAME/KEY: exon
<222> LOCATION: (479)..(706)
<223> OTHER INFORMATION:
<221> NAME/KEY: Intron
<222> LOCATION: (707)..(833)
<223> OTHER INFORMATION:
<221> NAME/KEY: exon
<222> LOCATION: (834)..(1384)
<223> OTHER INFORMATION:
<221> NAME/KEY: Intron
<222> LOCATION: (1385)..(1471)
<223> OTHER INFORMATION:
<221> NAME/KEY: exon
<222> LOCATION: (1472)..(1523)
<223> OTHER INFORMATION:
<221> NAME/KEY: Intron
<222> LOCATION: (1524)..(1591)
<223> OTHER INFORMATION:
<221> NAME/KEY: exon
<222> LOCATION: (1592)..(2383)
<223> OTHER INFORMATION:
<221> NAME/KEY: 3'UTR
<222> LOCATION: (2384)..(2794)
<223> OTHER INFORMATION:
```

```
<400> SEQUENCE: 32
taaaagaccg agtcacccga acatctccac cttcacgcca ttctcctacc actcggacct      60
aaccaaccaa taccttccac gtcatgtaca atccgagttc ccgtgagata gggatcttta    120
cttgaagcaa ccagacatga ccgcagagtc acacacacac acaccctaa gcttttttgtc    180 gtccctcgt atggaatcca ttgtgggacg acacaaaaat atcttctttt gcttctctgc    240
tttcttcttc ttcttcttaa aatttgtttc tttcaggtgg atttgatctc catctacgta    300
aaacaaaaac aaagtttata atcttttttgg attttgggat tgatctaaag tgagatttcg    360
atcttggcac taggttttgc aaggttacct aacaatttct ggttctgatt tcatttcttt    420
aggttacgtg taagggaagg aattgttaat agggtttgtt tgtgagcgta gggaaaag    478
```

```
atg gga gga atg aaa gat gaa gca aag agg ata aca att cct cca ttg    526
Met Gly Gly Met Lys Asp Glu Ala Lys Arg Ile Thr Ile Pro Pro Leu
 1               5                  10                  15 ttt cca agg gtt cat gtc aat gat act gga aga gga ggc ctg tct caa    574
Phe Pro Arg Val His Val Asn Asp Thr Gly Arg Gly Gly Leu Ser Gln
            20                  25                  30
```

```
caa ttt gat ggc aaa aca atg tct ctc gtc tct tct aaa cgt ccc aat      622
Gln Phe Asp Gly Lys Thr Met Ser Leu Val Ser Ser Lys Arg Pro Asn
         35                  40                  45 ctt cct tct ccg acc aac aac ata tct gat tct ctt tcc act ttc tct      670
Leu Pro Ser Pro Thr Asn Asn Ile Ser Asp Ser Leu Ser Thr Phe Ser
         50                  55                  60 ttg tct ctt cct cca cca cca aac aat gcc cgt ctc gtgagtcctt           716
Leu Ser Leu Pro Pro Pro Pro Asn Asn Ala Arg Leu
65                  70                  75 ttaattcact cattcaactt tcttggtttt gtgtgtctgc agatttatat acaagaatgg    776
tgacaatgca tatttagatt atcactttat gacttgttga atactttttt gtaacag      833 att gat gga cct gaa aag aat cag ttt tca cca atc tac aac aca aag      881
Ile Asp Gly Pro Glu Lys Asn Gln Phe Ser Pro Ile Tyr Asn Thr Lys
             80                  85                  90 ttt gag ggg aag ctg aat aaa aaa ggc ata aat tat aca agt cct aaa      929
Phe Glu Gly Lys Leu Asn Lys Lys Gly Ile Asn Tyr Thr Ser Pro Lys
         95                 100                 105 gga tca tca gtt act aat act aag cct agt tca ata aaa caa aat gag      977
Gly Ser Ser Val Thr Asn Thr Lys Pro Ser Ser Ile Lys Gln Asn Glu
         110                 115                 120 tac ctc aag aac ctt acc agc ttg gat tct att aag tct cct att gtt     1025
Tyr Leu Lys Asn Leu Thr Ser Leu Asp Ser Ile Lys Ser Pro Ile Val
125                 130                 135                 140 ata cac tca gaa ata gat cca caa gca aac aca gat ttg tca ctc caa     1073
Ile His Ser Glu Ile Asp Pro Gln Ala Asn Thr Asp Leu Ser Leu Gln
                145                 150                 155 ttt tgt act agc ggt agc agt aaa ccc gga gga gag gct gtt gtt ggt     1121
Phe Cys Thr Ser Gly Ser Ser Lys Pro Gly Gly Glu Ala Val Val Gly
         160                 165                 170 tct aag atc ctt ttg tca gaa cgt ttg gaa gat gaa aac cag aat ggg     1169
Ser Lys Ile Leu Leu Ser Glu Arg Leu Glu Asp Glu Asn Gln Asn Gly
         175                 180                 185 tct ccc aat gtg atg aaa act caa tca tat aga aga aac ttt gct gag     1217
Ser Pro Asn Val Met Lys Thr Gln Ser Tyr Arg Arg Asn Phe Ala Glu
         190                 195                 200 ttt aac aat gaa act caa aag aag ccc aaa act ctg cct cgg cgt gaa     1265
Phe Asn Asn Glu Thr Gln Lys Lys Pro Lys Thr Leu Pro Arg Arg Glu
205                 210                 215                 220 caa gtt gct tca aac tgc tct gca ata gag tct ttg tct ggt ata agt     1313
Gln Val Ala Ser Asn Cys Ser Ala Ile Glu Ser Leu Ser Gly Ile Ser
                225                 230                 235 gca tct tct tat gat att gcc aga gtg att ggt gaa aag agg ttt tgg     1361
Ala Ser Ser Tyr Asp Ile Ala Arg Val Ile Gly Glu Lys Arg Phe Trp
         240                 245                 250 aag atg aga aca tat atg atc aa  gtttgtatcc tcctctcact tttcttatga    1414
Lys Met Arg Thr Tyr Met Ile Asn
         255 tcccaacttc ataactttgc cgtatttctt actattttt attgttgata ttttcag t     1472 cag caa aag atc ttt gcc ggg caa gta ttt gag ctc cat aga ctg ata     1520
Gln Gln Lys Ile Phe Ala Gly Gln Val Phe Glu Leu His Arg Leu Ile
                265                 270                 275 atg gtaagctttt aataaccttta ttgtttctgg tttgctttct atgcttcaga         1573
Met ttacttaata tgatgcag gtt caa aag atg gtt gcg aag tcg cca aac ttg     1624
                    Val Gln Lys Met Val Ala Lys Ser Pro Asn Leu
                                280                 285 ttt ctt gaa agt aag ctt aat ggt gtc aaa cat ggt aca atg agg tca     1672
```

```
                                              -continued

Phe Leu Glu Ser Lys Leu Asn Gly Val Lys His Gly Thr Met Arg Ser
    290                 295                 300 tca cat cag ctt gca atg gcg gct tca aag gtt aga aag cca aac act      1720
Ser His Gln Leu Ala Met Ala Ala Ser Lys Val Arg Lys Pro Asn Thr
305                 310                 315                 320 gag aat cac aaa cct gta cct gaa gaa tat cca gag cat atg aaa cca      1768
Glu Asn His Lys Pro Val Pro Glu Glu Tyr Pro Glu His Met Lys Pro
                325                 330                 335 aag ctt cct cta cct tcc ata agc aaa gaa ctc gtg act cct att tgg      1816
Lys Leu Pro Leu Pro Ser Ile Ser Lys Glu Leu Val Thr Pro Ile Trp
            340                 345                 350 cca caa cag cta ctt cct cct cct gga aac caa tgg tta gtt cct gta      1864
Pro Gln Gln Leu Leu Pro Pro Pro Gly Asn Gln Trp Leu Val Pro Val
        355                 360                 365 ata act gat tca gac ggt ctg gtc tat aaa cca ttt cca gga cca tgt      1912
Ile Thr Asp Ser Asp Gly Leu Val Tyr Lys Pro Phe Pro Gly Pro Cys
    370                 375                 380 cct cct tct tct tca gcc ttc atg gtt cca gtt tat ggc caa gat tca      1960
Pro Pro Ser Ser Ser Ala Phe Met Val Pro Val Tyr Gly Gln Asp Ser
385                 390                 395                 400 ctc gag aca cca ttc agg ttc cct gtt tct tct cca ttc agc cac agc      2008
Leu Glu Thr Pro Phe Arg Phe Pro Val Ser Ser Pro Phe Ser His Ser
                405                 410                 415 tac ttc cca cct cct aac gcg agg aca aca gtt gac caa aca aac ccg      2056
Tyr Phe Pro Pro Pro Asn Ala Arg Thr Thr Val Asp Gln Thr Asn Pro
            420                 425                 430 ttt ggt cag ttt caa aga tgg tct aac aca tca agc cac atg aca caa      2104
Phe Gly Gln Phe Gln Arg Trp Ser Asn Thr Ser Ser His Met Thr Gln
        435                 440                 445 gcc att cca ttt tct tta aag aag tct cag gaa tct aat gac agt gac      2152
Ala Ile Pro Phe Ser Leu Lys Lys Ser Gln Glu Ser Asn Asp Ser Asp
    450                 455                 460 ata cat gga agc aca gct tca agt cca cca gag aag cat aaa ctt gaa      2200
Ile His Gly Ser Thr Ala Ser Ser Pro Pro Glu Lys His Lys Leu Glu
465                 470                 475                 480 gtg ctt cct ctg ttt cct aca gag cct acc cat caa act gat gag tac      2248
Val Leu Pro Leu Phe Pro Thr Glu Pro Thr His Gln Thr Asp Glu Tyr
                485                 490                 495 aag cag aaa cag caa ccg atg ctt cgc gcc att aaa gcc gtt cct cat      2296
Lys Gln Lys Gln Gln Pro Met Leu Arg Ala Ile Lys Ala Val Pro His
            500                 505                 510 aat tca aca tct gcc tct gaa tct gct gca agg atc ttc cgt ttc att      2344
Asn Ser Thr Ser Ala Ser Glu Ser Ala Ala Arg Ile Phe Arg Phe Ile
        515                 520                 525 cag gaa gaa agg agg gac tca gat cat atg att agt tag ttctttata       2393
Gln Glu Glu Arg Arg Asp Ser Asp His Met Ile Ser
530                 535                 540 tttgaaaccc ttccacattc ttttgctctc attgcttctt catctagctt agattttcag    2453
tatattctat ttactcttct tatgaagatg taaatcaaat actatcacta tacattaaac    2513
atacacacac ttatacacac atcttacatt gttcttgtat tgacaaacag ctaataaaag    2573
atagactttt gtgcttctat tccagttttg aggagtttaa acattggaac aagaagagtt    2633
ctttagccat tgaagtatct atattatcaa tgtggaagga gacaataagg atcagagttg    2693
tgtccatgct atacgaagct acactcaagt tcaagaacat ttcagaacaa aaaccaagaa    2753
caaaaagaag acaagagatc cattaattag aacccaagaa c                       2794

<210> SEQ ID NO 33
```

-continued

```
<211> LENGTH: 540
<212> TYPE: PRT
<213> ORGANISM: Arabidopsis thaliana

<400> SEQUENCE: 33

Met Gly Gly Met Lys Asp Glu Ala Lys Arg Ile Thr Ile Pro Pro Leu
1               5                   10                  15

Phe Pro Arg Val His Val Asn Asp Thr Gly Arg Gly Gly Leu Ser Gln
            20                  25                  30

Gln Phe Asp Gly Lys Thr Met Ser Leu Val Ser Ser Lys Arg Pro Asn
        35                  40                  45

Leu Pro Ser Pro Thr Asn Asn Ile Ser Asp Ser Leu Ser Thr Phe Ser
    50                  55                  60

Leu Ser Leu Pro Pro Pro Asn Asn Ala Arg Leu Ile Asp Gly Pro
65                  70                  75                  80

Glu Lys Asn Gln Phe Ser Pro Ile Tyr Asn Thr Lys Phe Glu Gly Lys
                85                  90                  95

Leu Asn Lys Lys Gly Ile Asn Tyr Thr Ser Pro Lys Gly Ser Ser Val
            100                 105                 110

Thr Asn Thr Lys Pro Ser Ser Ile Lys Gln Asn Glu Tyr Leu Lys Asn
        115                 120                 125

Leu Thr Ser Leu Asp Ser Ile Lys Ser Pro Ile Val Ile His Ser Glu
    130                 135                 140

Ile Asp Pro Gln Ala Asn Thr Asp Leu Ser Leu Gln Phe Cys Thr Ser
145                 150                 155                 160

Gly Ser Ser Lys Pro Gly Gly Glu Ala Val Val Gly Ser Lys Ile Leu
                165                 170                 175

Leu Ser Glu Arg Leu Glu Asp Glu Asn Gln Asn Gly Ser Pro Asn Val
            180                 185                 190

Met Lys Thr Gln Ser Tyr Arg Arg Asn Phe Ala Glu Phe Asn Asn Glu
        195                 200                 205

Thr Gln Lys Lys Pro Lys Thr Leu Pro Arg Arg Glu Gln Val Ala Ser
    210                 215                 220

Asn Cys Ser Ala Ile Glu Ser Leu Ser Gly Ile Ser Ala Ser Ser Tyr
225                 230                 235                 240

Asp Ile Ala Arg Val Ile Gly Glu Lys Arg Phe Trp Lys Met Arg Thr
                245                 250                 255

Tyr Met Ile Asn Gln Gln Lys Ile Phe Ala Gly Gln Val Phe Glu Leu
            260                 265                 270

His Arg Leu Ile Met Val Gln Lys Met Val Ala Lys Ser Pro Asn Leu
        275                 280                 285

Phe Leu Glu Ser Lys Leu Asn Gly Val Lys His Gly Thr Met Arg Ser
    290                 295                 300

Ser His Gln Leu Ala Met Ala Ala Ser Lys Val Arg Lys Pro Asn Thr
305                 310                 315                 320

Glu Asn His Lys Pro Val Pro Glu Glu Tyr Pro Glu His Met Lys Pro
                325                 330                 335

Lys Leu Pro Leu Pro Ser Ile Ser Lys Glu Leu Val Thr Pro Ile Trp
            340                 345                 350

Pro Gln Gln Leu Leu Pro Pro Gly Asn Gln Trp Leu Val Pro Val
        355                 360                 365

Ile Thr Asp Ser Asp Gly Leu Val Tyr Lys Pro Phe Pro Gly Pro Cys
    370                 375                 380

Pro Pro Ser Ser Ser Ala Phe Met Val Pro Val Tyr Gly Gln Asp Ser
```

```
385                390                395                400
Leu Glu Thr Pro Phe Arg Phe Pro Val Ser Ser Pro Phe Ser His Ser
                405                410                415

Tyr Phe Pro Pro Asn Ala Arg Thr Thr Val Asp Gln Thr Asn Pro
            420                425                430

Phe Gly Gln Phe Gln Arg Trp Ser Asn Thr Ser His Met Thr Gln
        435                440                445

Ala Ile Pro Phe Ser Leu Lys Lys Ser Gln Glu Ser Asn Asp Ser Asp
    450                455                460

Ile His Gly Ser Thr Ala Ser Ser Pro Pro Glu Lys His Lys Leu Glu
465                470                475                480

Val Leu Pro Leu Phe Pro Thr Glu Pro Thr His Gln Thr Asp Glu Tyr
                485                490                495

Lys Gln Lys Gln Gln Pro Met Leu Arg Ala Ile Lys Ala Val Pro His
            500                505                510

Asn Ser Thr Ser Ala Ser Glu Ser Ala Ala Arg Ile Phe Arg Phe Ile
            515                520                525

Gln Glu Glu Arg Arg Asp Ser Asp His Met Ile Ser
        530                535                540
```

<210> SEQ ID NO 34
<211> LENGTH: 4221
<212> TYPE: DNA
<213> ORGANISM: Arabidopsis thaliana
<220> FEATURE:
<221> NAME/KEY: 5'UTR
<222> LOCATION: (1)..(425)
<223> OTHER INFORMATION:
<221> NAME/KEY: exon
<222> LOCATION: (426)..(644)
<223> OTHER INFORMATION:
<221> NAME/KEY: Intron
<222> LOCATION: (645)..(1006)
<223> OTHER INFORMATION:
<221> NAME/KEY: exon
<222> LOCATION: (1007)..(1803)
<223> OTHER INFORMATION:
<221> NAME/KEY: Intron
<222> LOCATION: (1804)..(2983)
<223> OTHER INFORMATION:
<221> NAME/KEY: exon
<222> LOCATION: (2984)..(3035)
<223> OTHER INFORMATION:
<221> NAME/KEY: Intron
<222> LOCATION: (3036)..(3125)
<223> OTHER INFORMATION:
<221> NAME/KEY: exon
<222> LOCATION: (3126)..(4145)
<223> OTHER INFORMATION:
<221> NAME/KEY: 3'UTR
<222> LOCATION: (4146)..(4221)
<223> OTHER INFORMATION:

<400> SEQUENCE: 34

```
tatctttggg ggctccactt ttcctatctc tttttgcccc tttcctctct ctgttcacaa      60
gtcatcttct tccttcctct gaatcttgtt ccttttgct ctctctactt gattcaccca     120
ctctgtttct cgattagtac gttgaaaact cacttkggtt ttgtttgatt cctctttagt    180 ctgttttcg atttcgtttt ctctgattgg tttggtggtg agatctctat cgtagtttgt     240
cctttgggtt aagatatttc atttgattgg tgggtttgtt ttattgaagc ttattgttgt    300
gaaagttgga gtcttttctca gtttttaggt tgaattatta agagaaaggg aagatttttg    360
gtgtgaagtt aggttatttg gggtttgaga agtttgcaag tgaaaaaggt tgtgaattgt    420
```

-continued

```
gagtg atg aag aga ggg aaa gat gag gag aag ata ttg gaa cct atg ttt    470
      Met Lys Arg Gly Lys Asp Glu Glu Lys Ile Leu Glu Pro Met Phe
       1               5                  10                  15 cct cgg ctt cat gtg aat gat gca gat aaa gga ggg cct aga gct cct      518
Pro Arg Leu His Val Asn Asp Ala Asp Lys Gly Gly Pro Arg Ala Pro
                 20                  25                  30 cct aga aac aag atg gct ctt tat gag cag ctt agt att cct tct cag      566
Pro Arg Asn Lys Met Ala Leu Tyr Glu Gln Leu Ser Ile Pro Ser Gln
             35                  40                  45 agg ttt ggt gat cat gga acg atg aat tct cgt agt aac aac aca agc      614
Arg Phe Gly Asp His Gly Thr Met Asn Ser Arg Ser Asn Asn Thr Ser
         50                  55                  60 act ttg gtt cat cct gga cca tct agt cag gtattgtttt gattttgatc        664
Thr Leu Val His Pro Gly Pro Ser Ser Gln
     65                  70 attgtatagg ctcttgatgt tattagttgt atgagtttgg atgttatata gcctgaaaga    724
gaaagtagga cattggttga tctatgtttc aattgttatc agatcatagt atcttctttt    784
tgcttatgga ttgagctttt aggattgaat tctcctgtat atatgagagt cttgtagaca    844
caagtttatc taagtgtggt ttatttctta aaactaacat tcttgttgtg cctgattctt    904
tttatgttct gaagttcgat gaagttttct tgtgattgcc ctgagcattc agactattgc    964
aaggacatga gaaataatcc ttttttaccc tcttcaatga ag cct tgt ggt gtg      1018
                                                Pro Cys Gly Val
                                                            75 gaa aga aac tta tct gtc cag cat ctt gat tct tca gcc gca aac caa     1066
Glu Arg Asn Leu Ser Val Gln His Leu Asp Ser Ser Ala Ala Asn Gln
             80                  85                  90 gca act gag aag ttt gtc tcc caa atg tcc ttc atg gaa aat gtg aga     1114
Ala Thr Glu Lys Phe Val Ser Gln Met Ser Phe Met Glu Asn Val Arg
         95                 100                 105 tct tcg gca cag cat gat cag agg aaa atg gtg aga gag gaa gaa gat    1162
Ser Ser Ala Gln His Asp Gln Arg Lys Met Val Arg Glu Glu Glu Asp
110                 115                 120                 125 ttt gca gtt cca gta tat att aac tca aga aga tct cag tct cat ggc    1210
Phe Ala Val Pro Val Tyr Ile Asn Ser Arg Arg Ser Gln Ser His Gly
                130                 135                 140 aga acc aag agt ggt att gag aag gaa aaa cac acc cca atg gtg gca    1258
Arg Thr Lys Ser Gly Ile Glu Lys Glu Lys His Thr Pro Met Val Ala
            145                 150                 155 cct agc tct cat cac tcc att cga ttt caa gaa gtg aat cag aca ggc    1306
Pro Ser Ser His His Ser Ile Arg Phe Gln Glu Val Asn Gln Thr Gly
        160                 165                 170 tca aag caa aac gta tgt ttg gct act tgt tca aaa cct gaa gtt agg    1354
Ser Lys Gln Asn Val Cys Leu Ala Thr Cys Ser Lys Pro Glu Val Arg
    175                 180                 185 gat cag gtc aag gcg aat gca agg tca ggt ggc ttt gta atc tct tta    1402
Asp Gln Val Lys Ala Asn Ala Arg Ser Gly Gly Phe Val Ile Ser Leu
190                 195                 200                 205 gat gta tca gtc aca gag gag att gat ctc gaa aaa tca gca tca agt    1450
Asp Val Ser Val Thr Glu Glu Ile Asp Leu Glu Lys Ser Ala Ser Ser
                210                 215                 220 cat gat aga gta aat gat tat aat gct tcc ttg aga caa gag tct aga    1498
His Asp Arg Val Asn Asp Tyr Asn Ala Ser Leu Arg Gln Glu Ser Arg
            225                 230                 235 aat cgg tta tac cga gat ggt ggc aaa act cgt ctg aag gac act gat    1546
Asn Arg Leu Tyr Arg Asp Gly Gly Lys Thr Arg Leu Lys Asp Thr Asp
        240                 245                 250 aat gga gct gaa tct cac ttg gca acg gaa aat cat tca caa gag ggt    1594
```

```
                                                                       -continued Asn Gly Ala Glu Ser His Leu Ala Thr Glu Asn His Ser Gln Glu Gly
    255                 260                 265 cat ggc agt cct gaa gac att gat aat gat cgt gaa tac agc aaa agc        1642
His Gly Ser Pro Glu Asp Ile Asp Asn Asp Arg Glu Tyr Ser Lys Ser
270                 275                 280                 285 aga gca tgc gcc tct ctg cag cag ata aat gaa gag gca agt gat gac        1690
Arg Ala Cys Ala Ser Leu Gln Gln Ile Asn Glu Glu Ala Ser Asp Asp
                290                 295                 300 gtt tct gat gat tcg atg gtg gat tct ata tcc agc ata gat gtc tct        1738
Val Ser Asp Asp Ser Met Val Asp Ser Ile Ser Ser Ile Asp Val Ser
                305                 310                 315 ccc gat gat gtt gtg ggt ata tta ggt caa aaa cgt ttc tgg aga gca        1786
Pro Asp Asp Val Val Gly Ile Leu Gly Gln Lys Arg Phe Trp Arg Ala
            320                 325                 330 agg aaa gcc att gcc aa  gtaagttcac tagaaattta cagtttggtt              1833
Arg Lys Ala Ile Ala Asn
        335 atttattctc cgctctttct atttatctcc ttctttgata ccaacatttt ttgcttgaaa      1893 gaagttaata tttaagcatt gttccgtagt cttactgaag cttttttcctc tgttgttttt    1953 tgctattttc attgaggact gtggtagggc atatttcact atcaccaaat ttcaaatttc      2013 tagaacactc tccttcatat tttttttcat gattaatgct gcaattgatt gctgatatac      2073 atatatgact ataactcagt ttcatattct gtctcatttt gggagaaaga gatttcaggt      2133 ttatgcttga gaagtgatgg ttctatagtt gagaggcccc tgattcatct aaaatggtcc      2193 tattatgtgt ttagttgtag agtcctcggt agaatattaa cgcgtttaac acgttggatc      2253 atgttatagc agggagggac attctctgtt gacctatatt gtgcaaggtg cccgccgatg      2313 gctttattac tataccttct ttgcatctgg ttgttggaac atgtccctgt ctcggtttgg      2373 tattgctttt attctgcact gtcgtcttgg gcatttttccc tacttgtcat tcaaggggtt    2433 gaaccaggta gggaaatgtt tttccgagga ccccaggatc taaattttag ttaaccatac      2493 gtaaagttag ttttgagtct tatgacgatg cagaattata gtttcttctt actactgctt      2553 aagaggatcc ttagtgtggt tgtgaactac agagttttta tgattgtagg cttcatgact      2613 taacttttaa ggttcaatgt actctaatcc atatggtaag gtatcggatt cacgaccaat      2673 gcaaataata agatttttat ttcttgcttc ttgttaaata tctgacatct cattttgcag      2733 aggataagct gcgctgtaag ctagatttca ataagcccgt cctttgcatt gttatctatg      2793 ctttaatatg tcattggacc cattgatttg gttttcttct atcttttttg attggctatg      2853 tattcttgtt tctttttttcc tatctcattt cgatcgtatt gttccattag ctgttcaacc    2913 taaactatgt ctctctttgt tgaacttttg atggataatc ttcttaatgt gactctgttt      2973 ctcattacag t caa caa aga gta ttt gct gtt caa cta ttt gag ttg cac      3023
            Gln Gln Arg Val Phe Ala Val Gln Leu Phe Glu Leu His
                340                 345                 350 aga ctg att aag gtaaagtcat tcagaaactt ctcatatgtt tccatgagta            3075
Arg Leu Ile Lys
        355 tttgtttctt ctcgagctga aacaaacctc ttcaactgtg taataatcag gtt caa         3131
                                                           Val Gln aaa ctt att gct gca tca ccg gat ctc ttg ctc gat gag atc agt ttt        3179
Lys Leu Ile Ala Ala Ser Pro Asp Leu Leu Leu Asp Glu Ile Ser Phe
        360                 365                 370 ctt gga aaa gtt tct gct aaa agc tat cca gtg aag aag ctc ctt cca        3227
Leu Gly Lys Val Ser Ala Lys Ser Tyr Pro Val Lys Lys Leu Leu Pro
375                 380                 385                 390
```

```
tca gaa ttt ctg gta aag cct cct cta cca cat gtt gtc gtc aaa caa    3275
Ser Glu Phe Leu Val Lys Pro Pro Leu Pro His Val Val Val Lys Gln
                395                 400                 405 agg ggt gac tcg gag aag act gac caa cat aaa atg gaa agc tca gct    3323
Arg Gly Asp Ser Glu Lys Thr Asp Gln His Lys Met Glu Ser Ser Ala
            410                 415                 420 gag aac gta gtt ggg agg ttg tca aat caa ggt cat cat caa caa tcc    3371
Glu Asn Val Val Gly Arg Leu Ser Asn Gln Gly His His Gln Gln Ser
        425                 430                 435 aac tac atg cct ttt gca aac aac cca ccg gct tca ccg gct cca aat    3419
Asn Tyr Met Pro Phe Ala Asn Asn Pro Pro Ala Ser Pro Ala Pro Asn
    440                 445                 450 gga tat tgc ttt cct cct cag cct cct cct tca gga aat cat cag caa    3467
Gly Tyr Cys Phe Pro Pro Gln Pro Pro Pro Ser Gly Asn His Gln Gln
455                 460                 465                 470 tgg ttg atc cct gta atg tct ccc tcg gaa gga ctg ata tac aag cct    3515
Trp Leu Ile Pro Val Met Ser Pro Ser Glu Gly Leu Ile Tyr Lys Pro
                475                 480                 485 cac cca ggt atg gca cac acg ggg cat tat gga gga tat tat ggt cat    3563
His Pro Gly Met Ala His Thr Gly His Tyr Gly Gly Tyr Tyr Gly His
            490                 495                 500 tat atg cct aca cca atg gta atg cct caa tat cac ccc ggc atg gga    3611
Tyr Met Pro Thr Pro Met Val Met Pro Gln Tyr His Pro Gly Met Gly
        505                 510                 515 ttc cca cct cct ggt aat ggc tac ttc cct cca tat gga atg atg ccc    3659
Phe Pro Pro Pro Gly Asn Gly Tyr Phe Pro Pro Tyr Gly Met Met Pro
    520                 525                 530 acc ata atg aac cca tat tgt tca agc caa caa caa caa caa caa caa    3707
Thr Ile Met Asn Pro Tyr Cys Ser Ser Gln Gln Gln Gln Gln Gln Gln
535                 540                 545                 550 ccc aat gag caa atg aac cag ttt gga cat cct gga aat ctt cag aac    3755
Pro Asn Glu Gln Met Asn Gln Phe Gly His Pro Gly Asn Leu Gln Asn
                555                 560                 565 acc caa caa caa caa cag aga tct gat aat gaa cct gct cca cag caa    3803
Thr Gln Gln Gln Gln Gln Arg Ser Asp Asn Glu Pro Ala Pro Gln Gln
            570                 575                 580 cag caa cag cca aca aag tct tat ccg cga gca aga aag agc agg caa    3851
Gln Gln Gln Pro Thr Lys Ser Tyr Pro Arg Ala Arg Lys Ser Arg Gln
        585                 590                 595 ggg agc aca gga agc agt cca agt ggg cca cag gga atc tct ggt agc    3899
Gly Ser Thr Gly Ser Ser Pro Ser Gly Pro Gln Gly Ile Ser Gly Ser
    600                 605                 610 aag tcc ttt cgg cca ttc gca gcc gtt gat gag gac agc aac atc aac    3947
Lys Ser Phe Arg Pro Phe Ala Ala Val Asp Glu Asp Ser Asn Ile Asn
615                 620                 625                 630 aat gca cct gag caa acg atg aca aca acc aca acg aca aga aca         3995
Asn Ala Pro Glu Gln Thr Met Thr Thr Thr Thr Thr Thr Arg Thr
                635                 640                 645 act gtt act cag aca aca aga gat ggg gga gga gtg acg aga gtg ata    4043
Thr Val Thr Gln Thr Thr Arg Asp Gly Gly Gly Val Thr Arg Val Ile
            650                 655                 660 aag gtg gta cct cac aac gca aag ctc gcg agt gag aat gct gcc aga    4091
Lys Val Val Pro His Asn Ala Lys Leu Ala Ser Glu Asn Ala Ala Arg
        665                 670                 675 att ttc cag tca ata caa gaa gaa cgt aaa cgc tat gac tcc tct aag    4139
Ile Phe Gln Ser Ile Gln Glu Glu Arg Lys Arg Tyr Asp Ser Ser Lys
    680                 685                 690 cct taa tcctctctat gcgtattgta cttgatatgt attttacaaa attagaaaaa     4195
Pro
```

```
                                          695 ttgtgataga tgttatcctc aatata                                              4221

<210> SEQ ID NO 35
<211> LENGTH: 695
<212> TYPE: PRT
<213> ORGANISM: Arabidopsis thaliana

<400> SEQUENCE: 35

Met Lys Arg Gly Lys Asp Glu Glu Lys Ile Leu Glu Pro Met Phe Pro
1               5                   10                  15

Arg Leu His Val Asn Asp Ala Asp Lys Gly Gly Pro Arg Ala Pro Pro
            20                  25                  30

Arg Asn Lys Met Ala Leu Tyr Glu Gln Leu Ser Ile Pro Ser Gln Arg
        35                  40                  45

Phe Gly Asp His Gly Thr Met Asn Ser Arg Ser Asn Asn Thr Ser Thr
    50                  55                  60

Leu Val His Pro Gly Pro Ser Ser Gln Pro Cys Gly Val Glu Arg Asn
65                  70                  75                  80

Leu Ser Val Gln His Leu Asp Ser Ser Ala Ala Asn Gln Ala Thr Glu
                85                  90                  95

Lys Phe Val Ser Gln Met Ser Phe Met Glu Asn Val Arg Ser Ser Ala
            100                 105                 110

Gln His Asp Gln Arg Lys Met Val Arg Glu Glu Asp Phe Ala Val
        115                 120                 125

Pro Val Tyr Ile Asn Ser Arg Arg Ser Gln Ser His Gly Arg Thr Lys
    130                 135                 140

Ser Gly Ile Glu Lys Glu Lys His Thr Pro Met Val Ala Pro Ser Ser
145                 150                 155                 160

His His Ser Ile Arg Phe Gln Glu Val Asn Gln Thr Gly Ser Lys Gln
                165                 170                 175

Asn Val Cys Leu Ala Thr Cys Ser Lys Pro Glu Val Arg Asp Gln Val
            180                 185                 190

Lys Ala Asn Ala Arg Ser Gly Gly Phe Val Ile Ser Leu Asp Val Ser
        195                 200                 205

Val Thr Glu Glu Ile Asp Leu Glu Lys Ser Ala Ser His Asp Arg
    210                 215                 220

Val Asn Asp Tyr Asn Ala Ser Leu Arg Gln Ser Arg Asn Arg Leu
225                 230                 235                 240

Tyr Arg Asp Gly Gly Lys Thr Arg Leu Lys Asp Thr Asp Asn Gly Ala
                245                 250                 255

Glu Ser His Leu Ala Thr Glu Asn His Ser Gln Glu Gly His Gly Ser
            260                 265                 270

Pro Glu Asp Ile Asp Asn Asp Arg Glu Tyr Ser Lys Ser Arg Ala Cys
        275                 280                 285

Ala Ser Leu Gln Gln Ile Asn Glu Glu Ala Ser Asp Val Ser Asp
    290                 295                 300

Asp Ser Met Val Asp Ser Ile Ser Ile Asp Val Ser Pro Asp Asp
305                 310                 315                 320

Val Val Gly Ile Leu Gly Gln Lys Arg Phe Trp Arg Ala Arg Lys Ala
                325                 330                 335
```

-continued

```
Ile Ala Asn Gln Gln Arg Val Phe Ala Val Gln Leu Phe Glu Leu His
            340                 345                 350
Arg Leu Ile Lys Val Gln Lys Leu Ile Ala Ala Ser Pro Asp Leu Leu
            355                 360                 365
Leu Asp Glu Ile Ser Phe Leu Gly Lys Val Ser Ala Lys Ser Tyr Pro
            370                 375                 380
Val Lys Lys Leu Leu Pro Ser Glu Phe Leu Val Lys Pro Pro Leu Pro
385                 390                 395                 400
His Val Val Val Lys Gln Arg Gly Asp Ser Glu Lys Thr Asp Gln His
                405                 410                 415
Lys Met Glu Ser Ser Ala Glu Asn Val Val Gly Arg Leu Ser Asn Gln
            420                 425                 430
Gly His His Gln Gln Ser Asn Tyr Met Pro Phe Ala Asn Asn Pro Pro
            435                 440                 445
Ala Ser Pro Ala Pro Asn Gly Tyr Cys Phe Pro Pro Gln Pro Pro Pro
        450                 455                 460
Ser Gly Asn His Gln Gln Trp Leu Ile Pro Val Met Ser Pro Ser Glu
465                 470                 475                 480
Gly Leu Ile Tyr Lys Pro His Pro Gly Met Ala His Thr Gly His Tyr
            485                 490                 495
Gly Gly Tyr Tyr Gly His Tyr Met Pro Thr Pro Met Val Met Pro Gln
            500                 505                 510
Tyr His Pro Gly Met Gly Phe Pro Pro Pro Gly Asn Gly Tyr Phe Pro
        515                 520                 525
Pro Tyr Gly Met Met Pro Thr Ile Met Asn Pro Tyr Cys Ser Ser Gln
        530                 535                 540
Gln Gln Gln Gln Gln Pro Asn Glu Gln Met Asn Gln Phe Gly His
545                 550                 555                 560
Pro Gly Asn Leu Gln Asn Thr Gln Gln Gln Gln Arg Ser Asp Asn
            565                 570                 575
Glu Pro Ala Pro Gln Gln Gln Gln Pro Thr Lys Ser Tyr Pro Arg
        580                 585                 590
Ala Arg Lys Ser Arg Gln Gly Ser Thr Gly Ser Ser Pro Ser Gly Pro
        595                 600                 605
Gln Gly Ile Ser Gly Ser Lys Ser Phe Arg Pro Phe Ala Ala Val Asp
    610                 615                 620
Glu Asp Ser Asn Ile Asn Asn Ala Pro Glu Gln Thr Met Thr Thr Thr
625                 630                 635                 640
Thr Thr Thr Thr Arg Thr Thr Val Thr Gln Thr Thr Arg Asp Gly Gly
            645                 650                 655
Gly Val Thr Arg Val Ile Lys Val Val Pro His Asn Ala Lys Leu Ala
            660                 665                 670
Ser Glu Asn Ala Ala Arg Ile Phe Gln Ser Ile Gln Glu Glu Arg Lys
            675                 680                 685
Arg Tyr Asp Ser Ser Lys Pro
            690                 695
```